(12) United States Patent
Kolb et al.

(10) Patent No.: US 8,455,601 B2
(45) Date of Patent: Jun. 4, 2013

(54) POLYOLEFIN FILM

(75) Inventors: Rainer Kolb, Kingwood, TX (US); Francis C. Rix, League City, TX (US); R. Eric Pequeno, Baytown, TX (US)

(73) Assignee: Univation Technologies, LLC, Houston, TX (US)

(*) Notice: Subject to any disclaimer, the term of this patent is extended or adjusted under 35 U.S.C. 154(b) by 364 days.

(21) Appl. No.: 12/466,264

(22) Filed: May 14, 2009

(65) Prior Publication Data

US 2009/0306323 A1 Dec. 10, 2009

Related U.S. Application Data

(63) Continuation-in-part of application No. PCT/US2008/012823, filed on Nov. 14, 2008.

(60) Provisional application No. 61/003,181, filed on Nov. 15, 2007.

(51) Int. Cl.
*C08F 210/02* (2006.01)
*C08F 210/16* (2006.01)

(52) U.S. Cl.
USPC .................. 526/348; 526/352; 528/396

(58) Field of Classification Search
USPC .... 526/352, 348, 172, 351; 528/397; 525/240
See application file for complete search history.

(56) References Cited

U.S. PATENT DOCUMENTS

| | | | | |
|---|---|---|---|---|
| 4,243,619 A * | 1/1981 | Fraser et al. | 264/40.6 |
| 4,354,004 A * | 10/1982 | Hughes et al. | 525/240 |
| 4,530,914 A | 7/1985 | Ewen et al. | 502/113 |
| 4,659,685 A | 4/1987 | Coleman, III et al. | 502/113 |
| 4,937,299 A | 6/1990 | Ewen et al. | 526/119 |
| 5,470,811 A | 11/1995 | Jejelowo et al. | 502/117 |
| 5,516,848 A | 5/1996 | Canich et al. | 525/240 |
| 5,536,796 A * | 7/1996 | Jejelowo et al. | 526/116 |
| 5,665,818 A | 9/1997 | Tilston et al. | 525/53 |
| 5,696,045 A | 12/1997 | Winter et al. | 502/113 |
| 5,749,202 A * | 5/1998 | Eichbauer | 53/399 |
| 6,143,854 A * | 11/2000 | Bamberger et al. | 526/348.1 |
| 6,232,410 B1 | 5/2001 | Rowland et al. | 525/387 |
| 6,248,845 B1 * | 6/2001 | Loveday et al. | 526/113 |
| 6,268,448 B1 | 7/2001 | Collins et al. | 526/161 |
| 6,492,472 B2 | 12/2002 | Lue et al. | 526/114 |
| 6,800,692 B2 * | 10/2004 | Farley et al. | 525/191 |
| 6,932,592 B2 * | 8/2005 | Farley et al. | 425/523 |
| 6,936,675 B2 * | 8/2005 | Szul et al. | 526/348.2 |
| 6,956,088 B2 * | 10/2005 | Farley et al. | 526/113 |
| 7,122,601 B2 * | 10/2006 | Musgrave et al. | 525/191 |
| 7,141,632 B2 * | 11/2006 | Vaughan et al. | 526/114 |
| 7,163,906 B2 | 1/2007 | McDaniel et al. | 502/117 |
| 7,172,987 B2 | 2/2007 | Kao et al. | 502/117 |
| 7,241,715 B2 | 7/2007 | Boussie et al. | |
| 7,312,295 B2 * | 12/2007 | Hagen et al. | 526/348.1 |
| 2004/0010103 A1 | 1/2004 | Boussie et al. | 526/127 |
| 2005/0148744 A1 | 7/2005 | Kao | |
| 2010/0234547 A1 | 9/2010 | Kolb et al. | |
| 2010/0261861 A1 | 10/2010 | Kolb et al. | |
| 2010/0310892 A1 * | 12/2010 | German et al. | 428/523 |

FOREIGN PATENT DOCUMENTS

| | | |
|---|---|---|
| EP | 0310734 B1 | 11/1994 |
| EP | 0516018 B1 | 3/1996 |
| EP | 0743327 A2 | 11/1996 |
| EP | 0527221 B1 | 9/1997 |
| EP | 1368388 B1 | 3/2009 |
| WO | WO 01/40330 | 6/2001 |
| WO | WO 01/62808 | 8/2001 |
| WO | WO 02/060963 | 8/2002 |
| WO | WO 2006/086104 | 8/2006 |
| WO | WO 2007/035485 | 3/2007 |

* cited by examiner

*Primary Examiner* — Rip A. Lee
(74) *Attorney, Agent, or Firm* — Kristina Leavitt; Jennifer A. Schmidt; Leandro Arechederra, III

(57) ABSTRACT

A film of an ethylene polymer.

9 Claims, 4 Drawing Sheets

US 8,455,601 B2

POLYOLEFIN FILM

CROSS REFERENCE TO RELATED APPLICATIONS

This application is a continuation-in-part of Application No. PCT/US2008/12823, filed Nov. 14, 2008, which claims the benefit of Ser. No. 61/003,181, filed Nov. 15, 2007, the disclosures of which are incorporated by reference in their entireties.

FIELD OF THE INVENTION

The present disclosure relates generally to a polyolefin film, methods of making said film, and the polymers from which the film is produced.

BACKGROUND

The use of metallocene compounds in polymerization catalysts, and the use of metallocene catalysts for polymerization are known. However, there remains an ongoing effort to develop metallocene catalysts, polymerization processes using such catalysts, and polyolefin resins and products made therewith, each having advantageous properties and performance.

There are numerous references discussing metallocene catalyst systems comprising at least two catalyst components, wherein at least one component is a metallocene catalyst. For example, U.S. Pat. No. 4,530,914 discusses a catalyst system for producing polyethylene having a broad molecular weight distribution using two different metallocene-type catalyst compounds having different propagation and termination rate constants for ethylene polymerization. U.S. Pat. No. 4,937,299 is directed to a homogeneous catalyst system of at least two metallocene-type catalyst compounds each having different reactivity ratios for use in a single reactor to produce a polymer blend. U.S. Pat. No. 5,470,811 discusses producing polymers having improved product properties using an isomeric mixture of two or more substituted metallocene-type catalyst compounds. EP-A2-0 743 327 discuss the use of meso and racemic bridged mixed metallocene-type catalysts compounds to produce ethylene polymers having improved processability. U.S. Pat. No. 5,516,848 relates to a process for producing polypropylene using a bridged mono-cyclopentadienyl heteroatom containing compound and an unbridged, bis-cyclopentadienyl containing compound. EP-B1-0 310 734 discusses the use of a mixed bridged hafnium and zirconium metallocene-type catalyst compounds to produce a polymer having broad molecular weight distribution. U.S. Pat. No. 5,696,045 describes using at least two different bridged zirconium metallocene-type catalyst compounds to produce propylene polymers having a broad molecular weight distribution where one of the stereorigid zirconocenes has an indenyl ligand having a substituent on the six-member ring. EP-B1-516 018 describes using two different bridged zirconium metallocene-type catalyst compounds to produce a broad molecular weight distribution polypropylene polymer where one of the bridged metallocenes has indenyl ligands that are substituted in at least the two position. U.S. Pat. No. 6,492,472 discusses a catalyst system comprising at least two different metallocene compounds, the system comprising a bridged metallocene catalyst compound and a bridged, asymmetrically substituted, metallocene catalyst compound useful for producing polymers generally having a narrow molecular weight distribution. U.S. Pat. No. 7,141,632 discusses a mixed metallocene catalyst system including a poor comonomer incorporating metallocene catalyst compound and a good comonomer incorporating metallocene catalyst compound useful in producing a more broadly separated bimodal polymer composition. U.S. Pat. No. 7,163,906 discusses a catalyst composition comprising the contact product of at least one metallocene compound and at least one organochromium compound. U.S. Pat. No. 7,172,987 discusses a bimetallic catalyst system comprising a modified Ziegler-Natta catalyst component and a metallocene catalyst component useful for producing bimodal polymers, specifically polyethylene, having a polydispersity of from 12 to 50.

Additionally, there are also references directed to polymerization processes in which two or more polymerization reactors are joined in series, where one catalyst is used in a first reactor to produce a first polymer that is then fed into a second reactor with the same or different catalyst, typically under different reactor conditions. In this way, the resulting polymer from a series polymerization process is a combination or blend of two different polymers. These polymer blends, typically, contain a high molecular weight and a low molecular weight component. For example, U.S. Pat. No. 5,665,818 discusses using two fluidized gas phase reactors in series using a transition metal based catalyst to form an in situ polymer blend having improved extrudability. EP-B 1-0 527 221 discusses a series reactor process using metallocene-type catalyst systems for producing bimodal molecular weight distribution polymer products. However, series or multistage reactor processes are expensive and more difficult to operate.

In addition, a polymer produced in a single reactor having a plurality of desirable properties and/or characteristics remains elusive. This is especially true in the area of films. Films are often a tradeoff of properties. A film having a combination of good optical properties, e.g., clarity, haze, and the like; in combination with a film having improved dart impact strength and/or high melt strength would be of particular interest for use in various end-use applications. However, such a film, which may be produced on a commercial scale, remains elusive in the art.

Accordingly, there remains a need for catalyst systems with good reactor operability which is capable of producing a polymeric film having improved optical properties in combination with improved dart impact strength and/or high melt strength as compared to films known in the art. There is also a need for olefin polymers and polyolefin products having these enhanced properties. These and other limitations may be overcome with the catalysts, methods, polymers, and products of the present disclosure.

SUMMARY

The following presents a general summary of some of the many possible embodiments of this disclosure in order to provide a basic understanding of this disclosure. This summary is not an extensive overview of all embodiments of the disclosure. This summary is not intended to identify key or critical elements of the disclosure or to delineate or otherwise limit the scope of the claims. The following summary merely presents some concepts of the disclosure in a general form as a prelude to the more detailed description that follows.

According to a class of embodiments, there is provided a film of an ethylene polymer.

The film may comprise an ethylene polymer produced in a gas phase process comprising a catalyst system comprising a first catalyst compound and a second catalyst compound disposed on a support, wherein the first catalyst compound is a metallocene catalyst compound; and wherein the second catalyst compound has the following formula I:

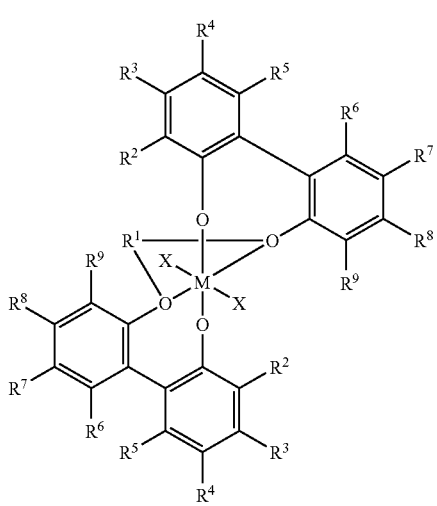

formula I wherein M is selected from the group consisting of Ti, Zr, and Hf, each $R^1$ through $R^9$ may be independently selected from the group consisting of hydride, hydrocarbyl, lower hydrocarbyl, substituted hydrocarbyl, heterohydrocarbyl, alkyl, lower alkyl, substituted alkyl, heteroalkyl, alkenyl, lower alkenyl, substituted alkenyl, heteroalkenyl, alkynyl, lower alkynyl, substituted alkynyl, heteroalkynyl, alkoxy, lower alkoxy, aryloxy, hydroxyl, alkylthio, lower alkyl thio, arylthio, thioxy, aryl, substituted aryl, heteroaryl, aralkyl, aralkylene, alkaryl, alkarylene, halide, haloalkyl, haloalkenyl, haloalkynyl, heteroalkyl, heterocycle, heteroaryl, heteroatom-containing group, silyl, boryl, phosphino, phosphine, amino, and amine; wherein X is least one leaving group; and optionally, a cocatalyst;

wherein the film of the ethylene polymer has improved gloss as determined by ASTM D2457-08, a reduced haze as determined by ASTM D2103-08, an improved dart drop impact strength as determined by ASTM D1709, and improved Elmendorf Tear in the machine direction as determined by ASTM 1922, an improved Elmendorf Tear in the Transverse direction as determined by ASTM 1922, or a combination thereof, when compared to a comparative film produced in essentially the same way from a comparative resin, the comparative resin produced in essentially the same way using essentially the same components except that the comparative resin is produced in the absence of the second catalyst compound.

BRIEF DESCRIPTION OF THE DRAWINGS

The following drawings illustrate some of the many possible embodiments of this disclosure in order to provide a basic understanding of the present disclosure. These drawings do not provide an extensive overview of all embodiments of this disclosure. These drawings are not intended to identify key or critical elements of the disclosure or to delineate or otherwise limit the scope of the claims. The following drawings merely present some concepts of the disclosure in a general form. Thus, for a detailed understanding of this disclosure, reference should be made to the following detailed description, taken in conjunction with the accompanying drawings, in which like elements have been given like numerals.

DETAILED DESCRIPTION

Figure 1:
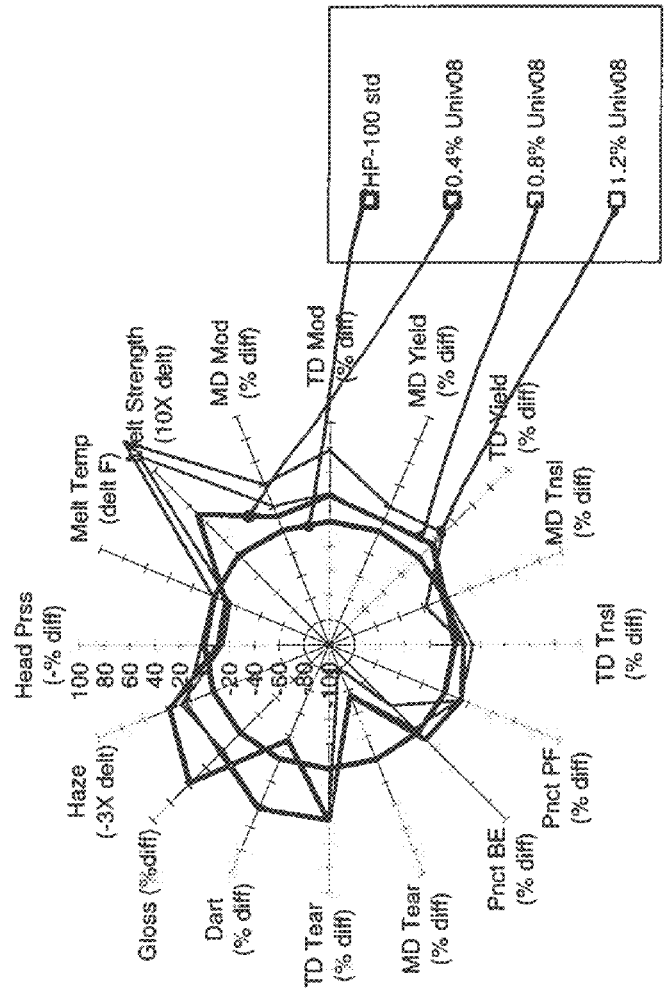
FIG. 1 provides a comparison of various properties of inventive 1.0 mil films of the instant disclosure produced with a Blow Up Ratio of 2, compared to a comparative film produced in the absence of the second catalyst of the instant disclosure.

Before the present compounds, components, compositions, and/or methods are disclosed and described, it is to be understood that unless otherwise indicated this invention is not limited to specific compounds, components, compositions, reactants, reaction conditions, ligands, metallocene structures, or the like, as such may vary, unless otherwise specified. It is also to be understood that the terminology used herein is for the purpose of describing particular embodiments only and is not intended to be limiting.

It must also be noted that, as used in the specification and the appended claims, the singular forms "a," "an," and "the" include plural referents unless otherwise specified. Thus, for example, reference to "a leaving group" as in a moiety "substituted with a leaving group" includes more than one leaving group, such that the moiety may be substituted with two or more such groups. Similarly, reference to "a halogen atom" as in a moiety "substituted with a halogen atom" includes more than one halogen atom, such that the moiety may be substituted with two or more halogen atoms, reference to "a substituent" includes one or more substituents, reference to "a ligand" includes one or more ligands, and the like.

The present disclosure provides catalyst systems for olefin polymerization, methods of making and method of using said catalyst systems, and polymer and products made therewith. The catalyst systems of the disclosure comprise at least two catalyst components—a first catalyst compound and a second catalyst compound. The catalyst systems may further comprise one or more additional catalyst compounds. Any two or more catalyst systems of the disclosure may be combined to produce a catalyst system of the disclosure. The terms "mixed catalyst system" and "mixed catalyst" may be used interchangeably herein with "catalyst system."

The catalyst systems of the present disclosure comprise a first catalyst component that produces generally low molecular weight polyolefin, and a second catalyst component that produces generally high molecular weight polyolefin. As known by one of skill in the art, although the precise molecular weight of a polyolefin produced by a polymerization catalyst in a polymerization reaction is dependent upon reaction conditions including, but not limited to, reaction temperature, hydrogen concentration, and comonomer concentration, catalysts can be described by the general molecular weight of the polyolefin they produce under standard reactor conditions, or a range of standard reactor conditions. The first catalyst component that produces low molecular weight polyolefin may be referred to herein as a "low molecular weight catalyst". The second catalyst component that produces generally high molecular weight polyolefin may be referred to herein as a "high molecular weight catalyst". It should be understood that the molecular weight is in reference to the polymer produced by the catalyst and not the molecular weight of the catalyst itself.

As used herein, "low molecular weight" is defined to be a weight average molecular weight (Mw) in the range of from about 40,000 to about 200,000 g/mol, preferably from about 50,000 to about 180,000 g/mol, more preferably from about 60,000 to about 175,000 g/mol, and even more preferably from about 70,000 to about 150,000 g/mol. In one non-limiting embodiment, low molecular weight is about 100,000 g/mol. As used herein, "high molecular weight" is defined as a weight average molecular weight (Mw) greater than about 1 million g/mol, preferably greater than about 1.5 million g/mol, even more preferably greater than about 2 million g/mol, and still more preferably greater than about 3 million g/mol. In one non-limiting embodiment, high molecular weight is about 5 million g/mol.

In one non-limiting embodiment of the disclosure, the low molecular weight catalyst component is a metallocene compound, and the high molecular weight catalyst is a non-metallocene compound, preferably a bridged phenoxide transition metal composition.

As used herein, the phrase "characterized by the formula" is not intended to be limiting and is used in the same way that "comprising" is commonly used. The term "independently selected" is used herein to indicate that the R groups, e.g., $R^1$, $R^2$, $R^3$, $R^4$, and $R^5$ can be identical or different (e.g. $R^1$, $R^2$, $R^3$, $R^4$, and $R^5$ may all be substituted alkyls or $R^1$ and $R^2$ may be a substituted alkyl and $R^3$ may be an aryl, etc.). Use of the singular includes use of the plural and vice versa (e.g., a hexane solvent, includes hexanes). A named R group will generally have the structure that is recognized in the art as corresponding to R groups having that name.

The terms "compound" and "complex" are generally used interchangeably in this specification, but those of skill in the art may recognize certain compounds as complexes and vice versa.

The terms "precatalyst", "catalyst", "precatalyst metal compound", "catalyst metal compound", "catalyst component" are generally used interchangeably in this specification, but those of skill in the art may recognize certain precatalysts as catalysts and vice versa.

The terms "monomer" and "comonomer" are generally used interchangeably in this specification, but those of skill in the art may recognize certain monomers as comonomers and vice versa.

For the purposes of illustration, representative certain groups are defined herein. These definitions are intended to supplement and illustrate, not preclude, the definitions known to those of skill in the art. "Optional" or "optionally" means that the subsequently described event or circumstance may or may not occur, and that the description includes instances where said event or circumstance occurs and instances where it does not. For example, the phrase "optionally substituted hydrocarbyl" means that a hydrocarbyl moiety may or may not be substituted and that the description includes both unsubstituted hydrocarbyl and hydrocarbyl where there is substitution.

The term "alkyl" as used herein refers to a branched or unbranched saturated hydrocarbon group typically although not necessarily containing 1 to about 50 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein may contain 1 to about 12 carbon atoms. The term "lower alkyl" intends an alkyl group of one to six carbon atoms, specifically one to four carbon atoms. The term alkyl also refers to divalent alkyls such as —$CR_2$— which may be referred to as alkylenes or hydrocarbylenes and may be substituted with one or more substituent groups or heteroatom containing groups. "Substituted alkyl" refers to alkyl substituted with one or more substituent groups (e.g., benzyl or chloromethyl), and the terms "heteroatom-containing alkyl" and "heteroalkyl" refer to alkyl in which at least one carbon atom is replaced with a heteroatom (e.g., —$CH_2OCH_3$ is an example of a heteroalkyl).

The term "alkenyl" as used herein refers to a branched or unbranched hydrocarbon group typically although not necessarily containing 2 to about 50 carbon atoms and at least one double bond, such as ethenyl, n-propenyl, isopropenyl, n-butenyl, isobutenyl, octenyl, decenyl, and the like. Generally, although again not necessarily, alkenyl groups herein contain 2 to about 12 carbon atoms. The term "lower alkenyl" intends an alkenyl group of two to six carbon atoms, specifically two to four carbon atoms. "Substituted alkenyl" refers to alkenyl substituted with one or more substituent groups, and the terms "heteroatom-containing alkenyl" and "heteroalkenyl" refer to alkenyl in which at least one carbon atom is replaced with a heteroatom.

The term "alkynyl" as used herein refers to a branched or unbranched hydrocarbon group typically although not necessarily containing 2 to about 50 carbon atoms and at least one triple bond, such as ethynyl, n-propynyl, isopropynyl, n-butynyl, isobutynyl, octynyl, decynyl, and the like. Generally, although again not necessarily, alkynyl groups herein may have 2 to about 12 carbon atoms. The term "lower alkynyl" intends an alkynyl group of two to six carbon atoms, specifically three or four carbon atoms. "Substituted alkynyl" refers to alkynyl substituted with one or more substituent groups, and the terms "heteroatom-containing alkynyl" and "heteroalkynyl" refer to alkynyl in which at least one carbon atom is replaced with a heteroatom.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group having one to six, more specifically one to four, carbon atoms. The term "aryloxy" is used in a similar fashion, with aryl as defined below. The term "hydroxy" refers to —OH.

Similarly, the term "alkylthio" as used herein intends an alkyl group bound through a single, terminal thioether linkage; that is, an "alkylthio" group may be represented as —S-alkyl where alkyl is as defined above. A "lower alkyl thio" group intends an alkyl thio group having one to six, more specifically one to four, carbon atoms. The term "arylthio" is used similarly, with aryl as defined below. The term "thioxy" refers to —SH.

The term "aryl" as used herein, and unless otherwise specified, refers to an aromatic substituent containing a single aromatic ring or multiple aromatic rings that are fused together, linked covalently, or linked to a common group such as a methylene or ethylene moiety. More specific aryl groups contain one aromatic ring or two or three fused or linked aromatic rings, e.g., phenyl, naphthyl, biphenyl, anthracenyl, phenanthrenyl, and the like. In particular embodiments, aryl substituents have 1 to about 200 carbon atoms, typically 1 to about 50 carbon atoms, and specifically 1 to about 20 carbon atoms. "Substituted aryl" refers to an aryl moiety substituted with one or more substituent groups, (e.g., tolyl, mesityl and perfluorophenyl) and the terms "heteroatom-containing aryl" and "heteroaryl" refer to aryl in which at least one carbon atom is replaced with a heteroatom (e.g., rings such as thiophene, pyridine, isoxazole, pyrazole, pyrrole, furan, etc. or benzo-fused analogues of these rings are included in the term "heteroaryl"). In some embodiments herein, multi-ring moieties are substituents and in such an embodiment the multi-ring moiety can be attached at an appropriate atom. For example, "naphthyl" can be 1-naphthyl or 2-naphthyl; "anthracenyl" can be 1-anthracenyl, 2-anthracenyl or 9-anthracenyl; and "phenanthrenyl" can be 1-phenanthrenyl, 2-phenanthrenyl, 3-phenanthrenyl, 4-phenanthrenyl or 9-phenanthrenyl.

The term "aralkyl" refers to an alkyl group with an aryl substituent, and the term "aralkylene" refers to an alkylene group with an aryl substituent; the term "alkaryl" refers to an aryl group that has an alkyl substituent, and the term "alkarylene" refers to an arylene group with an alkyl substituent.

The terms "halo" and "halogen" and "halide" are used in the conventional sense to refer to a chloro, bromo, fluoro or iodo substituent. The terms "haloalkyl," "haloalkenyl" or "haloalkynyl" (or "halogenated alkyl," "halogenated alkenyl," or "halogenated alkynyl") refers to an alkyl, alkenyl or alkynyl group, respectively, in which at least one of the hydrogen atoms in the group has been replaced with a halogen atom.

The term "heteroatom-containing" as in a "heteroatom-containing hydrocarbyl group" refers to a molecule or molecular fragment in which one or more carbon atoms is replaced with an atom other than carbon, e.g., nitrogen, oxygen, sulfur, phosphorus, boron or silicon. Similarly, the term "heteroalkyl" refers to an alkyl substituent that is heteroatom-containing, the term "heterocyclic" refers to a cyclic substituent that is heteroatom-containing, the term "heteroaryl" refers to an aryl substituent that is heteroatom-containing, and the like. When the term "heteroatom-containing" appears prior to a list of possible heteroatom-containing groups, it is intended that the term apply to every member of that group. That is, the phrase "heteroatom-containing alkyl, alkenyl and alkynyl" is to be interpreted as "heteroatom-containing alkyl, heteroatom-containing alkenyl and heteroatom-containing alkynyl."

"Hydrocarbyl" refers to hydrocarbyl radicals containing 1 to about 50 carbon atoms, specifically 1 to about 24 carbon atoms, most specifically 1 to about 16 carbon atoms, including branched or unbranched, saturated or unsaturated species, such as alkyl groups, alkenyl groups, aryl groups, and the like. The term "lower hydrocarbyl" intends a hydrocarbyl group of one to six carbon atoms, specifically one to four carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom.

By "substituted" as in "substituted hydrocarbyl," "substituted aryl," "substituted alkyl," "substituted alkenyl" and the like, as alluded to in some of the aforementioned definitions, is meant that in the hydrocarbyl, hydrocarbylene, alkyl, alkenyl, aryl or other moiety, at least one hydrogen atom bound to a carbon atom is replaced with one or more substituents that are functional groups such as hydroxyl, alkoxy, alkylthio, phosphino, amino, halo, silyl, and the like. When the term "substituted" appears prior to a list of possible substituted groups, it is intended that the term apply to every member of that group. That is, the phrase "substituted alkyl, alkenyl and alkynyl" is to be interpreted as "substituted alkyl, substituted alkenyl and substituted alkynyl." Similarly, "optionally substituted alkyl, alkenyl and alkynyl" is to be interpreted as "optionally substituted alkyl, optionally substituted alkenyl and optionally substituted alkynyl."

By "divalent" as in "divalent hydrocarbyl", "divalent alkyl", "divalent aryl" and the like, is meant that the hydrocarbyl, alkyl, aryl or other moiety is bonded at two points to atoms, molecules or moieties with the two bonding points being covalent bonds. The term "aromatic" is used in its usual sense, including unsaturation that is essentially delocalized across multiple bonds, such as around a ring.

As used herein the term "silyl" refers to the —$SiZ^1Z^2Z^3$ radical, where each of $SiZ^1Z^2Z^3$ is independently selected from the group consisting of hydride and optionally substituted alkyl, alkenyl, alkynyl, heteroatom-containing alkyl, heteroatom-containing alkenyl, heteroatom-containing alkynyl, aryl, heteroaryl, alkoxy, aryloxy, amino, silyl and combinations thereof.

As used herein the term "boryl" refers to the —$BZ^1Z^2$ group, where each of $Z^1$ and $Z^2$ is as defined above. As used herein, the term "phosphino" refers to the group —$PZ^1Z^2$, where each of $Z^1$ and $Z^2$ is as defined above. As used herein, the term "phosphine" refers to the group: $PZ^1Z^2Z^3$, where each of $Z^1$, $Z^2$, $Z^3$ as defined above. The term "amino" is used herein to refer to the group —$NZ^1Z^2$, where each of $Z^1$ and $Z^2$ is as defined above. The term "amine" is used herein to refer to the group: $NZ^1Z^2Z^3$, where each of $Z^1$, $Z^2$, $Z^3$ is as defined above.

The term "saturated" refers to lack of double and triple bonds between atoms of a radical group such as ethyl, cyclohexyl, pyrrolidinyl, and the like. The term "unsaturated" refers to the presence of one or more double and triple bonds between atoms of a radical group such as vinyl, acetylide, oxazolinyl, cyclohexenyl, acetyl and the like.

Metallocene Catalysts

The catalyst system may include at least one metallocene catalyst component. The metallocene catalyst component may include "half sandwich" and "full sandwich" compounds having one or more Cp ligands (cyclopentadienyl and ligands isolobal to cyclopentadienyl) bound to at least one Group 3 to Group 12 metal atom, and one or more leaving group(s) bound to the at least one metal atom. Hereinafter, these compounds will be referred to as "metallocenes" or "metallocene catalyst components".

In one aspect, the one or more metallocene catalyst components are represented by the formula (I):

$$Cp^A Cp^B MX_n \qquad (I)$$

The metal atom "M" of the metallocene catalyst compound, as described throughout the specification and claims, may be selected from the group consisting of Groups 3 through 12 atoms and lanthanide Group atoms in one embodiment; and selected from the group consisting of Groups 3 through 10 atoms in a more particular embodiment, and selected from the group consisting of Sc, Ti, Zr, Hf, V, Nb, Ta, Mn, Re, Fe, Ru, Os, Co, Rh, Ir, and Ni in yet a more particular embodiment; and selected from the group consisting of Groups 4, 5 and 6 atoms in yet a more particular embodiment, and a Ti, Zr, Hf atoms in yet a more particular embodiment, and Zr in yet a more particular embodiment. The oxidation state of the metal atom "M" may range from 0 to +7 in one embodiment; and in a more particular embodiment, is +1, +2, +3, +4 or +5; and in yet a more particular embodiment is +2, +3 or +4. The groups bound the metal atom "M" is such that the compounds described below in the formulas and structures are neutral, unless otherwise indicated. The Cp ligand(s)

form at least one chemical bond with the metal atom M to form the "metallocene catalyst compound". The Cp ligands are distinct from the leaving groups bound to the catalyst compound in that they are not highly susceptible to substitution/abstraction reactions.

M is as described above; each X is chemically bonded to M; each Cp group is chemically bonded to M; and n is 0 or an integer from 1 to 4, and either 1 or 2 in a particular embodiment.

The ligands represented by $Cp^A$ and $Cp^B$ in formula (I) may be the same or different cyclopentadienyl ligands or ligands isolobal to cyclopentadienyl, either or both of which may contain heteroatoms and either or both of which may be substituted by a group R. In one embodiment, $Cp^A$ and $Cp^B$ are independently selected from the group consisting of cyclopentadienyl, indenyl, tetrahydroindenyl, fluorenyl, and substituted derivatives of each.

Independently, each $Cp^A$ and $Cp^B$ of formula (I) may be unsubstituted or substituted with any one or combination of substituent groups R. Non-limiting examples of substituent groups R as used in structure (I) include hydrogen radicals, hydrocarbyls, lower hydrocarbyls, substituted hydrocarbyls, heterohydrocarbyls, alkyls, lower alkyls, substituted alkyls, heteroalkyls, alkenyls, lower alkenyls, substituted alkenyls, heteroalkenyls, alkynyls, lower alkynyls, substituted alkynyls, heteroalkynyls, alkoxys, lower alkoxys, aryloxys, hydroxyls, alkylthios, lower alkyls thios, arylthios, thioxys, aryls, substituted aryls, heteroaryls, aralkyls, aralkylenes, alkaryls, alkarylenes, halides, haloalkyls, haloalkenyls, haloalkynyls, heteroalkyls, heterocycles, heteroaryls, heteroatom-containing groups, silyls, boryls, phosphinos, phosphines, aminos, amines, cycloalkyls, acyls, aroyls, alkylthiols, dialkylamines, alkylamidos, alkoxycarbonyls, aryloxycarbonyls, carbomoyls, alkyl- and dialkyl-carbamoyls, acyloxys, acylaminos, aroylaminos, and combinations thereof.

More particular non-limiting examples of alkyl substituents R associated with formula (I) includes methyl, ethyl, propyl, butyl, pentyl, hexyl, cyclopentyl, cyclohexyl, benzyl, phenyl, methylphenyl, and tert-butylphenyl groups and the like, including all their isomers, for example tertiary-butyl, isopropyl, and the like. Other possible radicals include substituted alkyls and aryls such as, for example, fluoromethyl, fluoroethyl, difluoroethyl, iodopropyl, bromohexyl, chlorobenzyl and hydrocarbyl substituted organometalloid radicals including trimethylsilyl, trimethylgermyl, methyldiethylsilyl and the like; and halocarbyl-substituted organometalloid radicals including tris(trifluoromethyl)silyl, methylbis(difluoromethyl)silyl, bromomethyldimethylgermyl and the like; and disubstituted boron radicals including dimethylboron for example; and disubstituted Group 15 radicals including dimethylamine, dimethylphosphine, diphenylamine, methylphenylphosphine, Group 16 radicals including methoxy, ethoxy, propoxy, phenoxy, methylsulfide and ethylsulfide. Other substituents R include olefins such as but not limited to olefinically unsaturated substituents including vinyl-terminated ligands, for example 3-butenyl, 2-propenyl, 5-hexenyl and the like. In one embodiment, at least two R groups, two adjacent R groups in one embodiment, are joined to form a ring structure having from 3 to 30 atoms selected from the group consisting of carbon, nitrogen, oxygen, phosphorous, silicon, germanium, aluminum, boron and combinations thereof. Also, a substituent group R group such as 1-butanyl may form a bonding association to the element M.

Each X in formula (I) is independently selected from the group consisting of: any leaving group in one embodiment; halogen ions, hydrides, hydrocarbyls, lower hydrocarbyls, substituted hydrocarbyls, heterohydrocarbyls, alkyls, lower alkyls, substituted alkyls, heteroalkyls, alkenyls, lower alkenyls, substituted alkenyls, heteroalkenyls, alkynyls, lower alkynyls, substituted alkynyls, heteroalkynyls, alkoxys, lower alkoxys, aryloxys, hydroxyls, alkylthios, lower alkyls thios, arylthios, thioxys, aryls, substituted aryls, heteroaryls, aralkyls, aralkylenes, alkaryls, alkarylenes, halides, haloalkyls, haloalkenyls, haloalkynyls, heteroalkyls, heterocycles, heteroaryls, heteroatom-containing groups, silyls, boryls, phosphinos, phosphines, aminos, amines, cycloalkyls, acyls, aroyls, alkylthiols, dialkylamines, alkylamidos, alkoxycarbonyls, aryloxycarbonyls, carbomoyls, alkyl- and dialkyl-carbamoyls, acyloxys, acylaminos, aroylaminos, and combinations thereof. In another embodiment, X is $C_1$ to $C_{12}$ alkyls, $C_2$ to $C_{12}$ alkenyls, $C_6$ to $C_{12}$ aryls, $C_7$ to $C_{20}$ alkylaryls, $C_1$ to $C_{12}$ alkoxys, $C_6$ to $C_{16}$ aryloxys, $C_7$ to $C_{18}$ alkylaryloxys, $C_1$ to $C_{12}$ fluoroalkyls, $C_6$ to $C_{12}$ fluoroaryls, and $C_1$ to $C_{12}$ heteroatom-containing hydrocarbons and substituted derivatives thereof in a more particular embodiment; hydride, halogen ions, $C_1$ to $C_6$ alkyls, $C_2$ to $C_6$ alkenyls, $C_7$ to $C_{18}$ alkylaryls, $C_1$ to $C_6$ alkoxys, $C_6$ to $C_{14}$ aryloxys, $C_7$ to $C_{16}$ alkylaryloxys, $C_1$ to $C_6$ alkylcarboxylates, $C_1$ to $C_6$ fluorinated alkylcarboxylates, $C_6$ to $C_{12}$ arylcarboxylates, $C_7$ to $C_{18}$ alkylarylcarboxylates, $C_1$ to $C_6$ fluoroalkyls, $C_2$ to $C_6$ fluoroalkenyls, and $C_7$ to $C_{18}$ fluoroalkylaryls in yet a more particular embodiment; hydride, chloride, fluoride, methyl, phenyl, phenoxy, benzoxy, tosyl, fluoromethyls and fluorophenyls in yet a more particular embodiment; $C_1$ to $C_{12}$ alkyls, $C_2$ to $C_{12}$ alkenyls, $C_6$ to $C_{12}$ aryls, $C_7$ to $C_{20}$ alkylaryls, substituted $C_1$ to $C_{12}$ alkyls, substituted $C_6$ to $C_{12}$ aryls, substituted $C_7$ to $C_{20}$ alkylaryls and $C_1$ to $C_{12}$ heteroatom-containing alkyls, $C_1$ to $C_{12}$ heteroatom-containing aryls and $C_1$ to $C_{12}$ heteroatom-containing alkylaryls in yet a more particular embodiment; chloride, fluoride, $C_1$ to $C_6$ alkyls, $C_2$ to $C_6$ alkenyls, $C_7$ to $C_{18}$ alkylaryls, halogenated $C_1$ to $C_6$ alkyls, halogenated $C_2$ to $C_6$ alkenyls, and halogenated $C_7$ to $C_{18}$ alkylaryls in yet a more particular embodiment; fluoride, methyl, ethyl, propyl, phenyl, methylphenyl, dimethylphenyl, trimethylphenyl, fluoromethyls (mono-, di- and trifluoromethyls) and fluorophenyls (mono-, di-, tri-, tetra- and pentafluorophenyls) in yet a more particular embodiment.

Other non-limiting examples of X groups in formula (I) include amines, phosphines, ethers, carboxylates, dienes, hydrocarbon radicals having from 1 to 20 carbon atoms, fluorinated hydrocarbon radicals (e.g., —$C_6F_5$ (pentafluorophenyl)), fluorinated alkylcarboxylates (e.g. $CF_3C(O)O—$), hydrides and halogen ions and combinations thereof. Other examples of X ligands include alkyl groups such as cyclobutyl, cyclohexyl, methyl, heptyl, tolyl, trifluoromethyl, tetramethylene, pentamethylene, methylidene, methyoxy, ethyoxy, propoxy, phenoxy, bis(N-methylanilide), dimethylamide, dimethylphosphide radicals and the like. In one embodiment, two or more X's form a part of a fused ring or ring system.

In another aspect, the metallocene catalyst component includes those of formula (I) where $Cp^A$ and $Cp^B$ are bridged to each other by at least one bridging group, (A), such that the structure is represented by formula (II):

$$Cp^A(A)Cp^BMX_n \qquad (II)$$

These bridged compounds represented by formula (II) are known as "bridged metallocenes". $Cp^A$, $Cp^B$, M, X and n are as defined above for formula (I); and wherein each Cp ligand is chemically bonded to M, and (A) is chemically bonded to each Cp. Non-limiting examples of bridging group (A) include divalent alkyls, divalent lower alkyls, divalent substituted alkyls, divalent heteroalkyls, divalent alkenyls, divalent lower alkenyls, divalent substituted alkenyls, divalent heteroalkenyls, divalent alkynyls, divalent lower alkynyls, divalent substituted alkynyls, divalent heteroalkynyls, divalent alkoxys, divalent lower alkoxys, divalent aryloxys, divalent alkylthios, divalent lower alkyl thios, divalent arylthios, divalent aryls, divalent substituted aryls, divalent heteroaryls, divalent aralkyls, divalent aralkylenes, divalent alkaryls, divalent alkarylenes, divalent haloalkyls, divalent haloalkenyls, divalent haloalkynyls, divalent heteroalkyls, divalent heterocycles, divalent heteroaryls, divalent heteroatom-containing groups, divalent hydrocarbyls, divalent lower hydrocarbyls, divalent substituted hydrocarbyls, divalent heterohydrocarbyls, divalent silyls, divalent boryls, divalent phosphinos, divalent phosphines, divalent aminos, divalent amines, divalent ethers, divalent thioethers. Additional non-limiting examples of bridging group A include divalent hydrocarbon groups containing at least one Group 13 to 16 atom, such as but not limited to at least one of a carbon, oxygen, nitrogen, silicon, aluminum, boron, germanium and tin atom and combinations thereof, wherein the heteroatom may also be $C_1$ to $C_{12}$ alkyl or aryl substituted to satisfy neutral valency. The bridging group (A) may also contain substituent groups R as defined above for formula (I) including halogen radicals and iron. More particular non-limiting examples of bridging group (A) are represented by $C_1$ to $C_6$ alkylenes, substituted $C_1$ to $C_6$ alkylenes, oxygen, sulfur, $R'_2C=$, $R'_2Si=$, $-Si(R')_2Si(R'_2$, $R'_2Ge=$, $R'P=$ (wherein "=" represents two chemical bonds), where R' is independently selected from the group consisting of hydride, hydrocarbyl, substituted hydrocarbyl, halocarbyl, substituted halocarbyl, hydrocarbyl-substituted organometalloid, halocarbyl-substituted organometalloid, disubstituted boron, disubstituted Group 15 atoms, substituted Group 16 atoms, and halogen radical; and wherein two or more R' may be joined to form a ring or ring system. In one embodiment, the bridged metallocene catalyst component of formula (II) has two or more bridging groups (A).

Other non-limiting examples of bridging group (A) include methylene, ethylene, ethylidene, propylidene, isopropylidene, diphenylmethylene, 1,2-dimethylethylene, 1,2-diphenylethylene, 1,1,2,2-tetramethylethylene, dimethylsilyl, diethylsilyl, methyl-ethylsilyl, trifluoromethylbutylsilyl, bis(trifluoromethyl)silyl, di(n-butyl)silyl, di(n-propyl)silyl, di(i-propyl)silyl, di(n-hexyl)silyl, dicyclohexylsilyl, diphenylsilyl, cyclohexylphenylsilyl, t-butylcyclohexylsilyl, di(t-butylphenyl)silyl, di(p-tolyl)silyl and the corresponding moieties wherein the Si atom is replaced by a Ge or a C atom; dimethylsilyl, diethylsilyl, dimethylgermyl and diethylgermyl.

In another embodiment, bridging group (A) may also be cyclic, comprising, for example 4 to 10, 5 to 7 ring members in a more particular embodiment. The ring members may be selected from the elements mentioned above, from one or more of B, C, Si, Ge, N and O in a particular embodiment. Non-limiting examples of ring structures which may be present as or part of the bridging moiety are cyclobutylidene, cyclopentylidene, cyclohexylidene, cycloheptylidene, cyclooctylidene and the corresponding rings where one or two carbon atoms are replaced by at least one of Si, Ge, N and O, in particular, Si and Ge. The bonding arrangement between the ring and the Cp groups may be either cis-, trans-, or a combination.

The cyclic bridging groups (A) may be saturated or unsaturated and/or carry one or more substituents and/or be fused to one or more other ring structures. If present, the one or more substituents are selected from the group consisting of hydrocarbyl (e.g., alkyl such as methyl) and halogen (e.g., F, Cl) in one embodiment. The one or more Cp groups which the above cyclic bridging moieties may optionally be fused to may be saturated or unsaturated and are selected from the group consisting of those having 4 to 10, more particularly 5, 6 or 7 ring members (selected from the group consisting of C, N, O and S in a particular embodiment) such as, for example, cyclopentyl, cyclohexyl and phenyl. Moreover, these ring structures may themselves be fused such as, for example, in the case of a naphthyl group. Moreover, these (optionally fused) ring structures may carry one or more substituents. Illustrative, non-limiting examples of these substituents are hydrocarbyl (particularly alkyl) groups and halogen atoms.

The ligands $Cp^A$ and $Cp^B$ of formula (I) and (II) are different from each other in one embodiment, and the same in another embodiment.

In yet another aspect, the metallocene catalyst components include mono-ligand metallocene compounds (e.g., mono cyclopentadienyl catalyst components) such as described in WO 93/08221 for example. In this embodiment, the at least one metallocene catalyst component is a bridged "half-sandwich" metallocene represented by the formula (III):

$$Cp^A(A)QMX_n \qquad (III)$$

wherein $Cp^A$ is defined above and is bound to M; (A) is defined above and is a bridging group bonded to Q and $Cp^A$; and wherein an atom from the Q group is bonded to M; and n is 0 or an integer from 1 to 3; 1 or 2 in a particular embodiment. In formula (III), $Cp^A$, (A) and Q may form a fused ring system. The X groups and n of formula (III) are as defined above in formula (I) and (II). In one embodiment, $Cp^A$ is selected from the group consisting of cyclopentadienyl, indenyl, tetrahydroindenyl, fluorenyl, substituted versions thereof, and combinations thereof.

In formula (III), Q is a heteroatom-containing ligand in which the bonding atom (the atom that is bonded with the metal M) is selected from the group consisting of Group 15 atoms and Group 16 atoms in one embodiment, and selected from the group consisting of nitrogen, phosphorus, oxygen or sulfur atom in a more particular embodiment, and nitrogen and oxygen in yet a more particular embodiment. Non-limiting examples of Q groups include ethers, amines, phosphines, thioethers, alkylamines, arylamines, mercapto compounds, ethoxy compounds, carboxylates (e.g., pivalate), carbamates, azenyl, azulene, pentalene, phosphoyl, phosphinimine, pyrrolyl, pyrozolyl, carbazolyl, borabenzene other compounds comprising Group 15 and Group 16 atoms capable of bonding with M.

In yet another aspect, the at least one metallocene catalyst component is an unbridged "half sandwich" metallocene represented by the formula (IV):

$$Cp^A MQ_qX_n \qquad (IV)$$

wherein $Cp^A$ is defined as for the Cp groups in (I) and is a ligand that is bonded to M; each Q is independently bonded to M; Q is also bound to $Cp^A$ in one embodiment; X is a leaving group as described above in (I); n ranges from 0 to 3, and is 1 or 2 in one embodiment; q ranges from 0 to 3, and is 1 or 2 in one embodiment. In one embodiment, $Cp^A$ is selected from the group consisting of cyclopentadienyl, indenyl, tetrahydroindenyl, fluorenyl, substituted version thereof, and combinations thereof.

In formula (iV), Q is selected from the group consisting of $ROO^-$, $RO-$, $R(O)-$, $-NR-$, $-CR_2-$, $-S-$, $-NR_2$, $-CR_3$, $-SR$, $-SiR_3$, $-PR_2$, $-H$, and substituted and unsubstituted aryl groups, wherein R is selected from the group consisting of hydrocarbyls, lower hydrocarbyls, substituted hydrocarbyls, heterohydrocarbyls, alkyls, lower alkyls, substituted alkyls, heteroalkyls, alkenyls, lower alkenyls, substituted alkenyls, heteroalkenyls, alkynyls, lower alkynyls, substituted alkynyls, heteroalkynyls, alkoxys, lower alkoxys, aryloxys, hydroxyls, alkylthios, lower alkyls thios, arylthios, thioxys, aryls, substituted aryls, heteroaryls, aralkyls, aralkylenes, alkaryls, alkarylenes, halides, haloalkyls, haloalkenyls, haloalkynyls, heteroalkyls, heterocycles, heteroaryls, heteroatom-containing groups, silyls, boryls, phosphinos, phosphines, aminos, amines, cycloalkyls, acyls, aroyls, alkylthiols, dialkylamines, alkylamidos, alkoxycarbonyls, aryloxycarbonyls, carbomoyls, alkyl- and dialkyl-carbamoyls, acyloxys, acylaminos, aroylaminos, and combinations thereof. In another embodiment, R is selected from $C_1$ to $C_6$ alkyls, $C_6$ to $C_{12}$ aryls, $C_1$ to $C_6$ alkylamines, $C_6$ to $C_{12}$ alkylarylamines, $C_1$ to $C_6$ alkoxys, $C_6$ to $C_{12}$ aryloxys, and the like. Non-limiting examples of Q include $C_1$ to $C_{12}$ carbamates, $C_1$ to $C_{12}$ carboxylates (e.g., pivalate), $C_2$ to $C_{20}$ alkyls, and $C_2$ to $C_{20}$ heteroalkyl moieties.

Described another way, the "half sandwich" metallocenes above can be described as in formula (II), such as described in, for example, U.S. Pat. No. 6,069,213:

$$Cp^4M(Q_2GZ)X_n \text{ or } T(Cp^4 M(Q_2GZ)X_n)_m \qquad (V)$$

wherein M, $Cp^4$, X and n are as defined above;

$Q_2GZ$ forms a polydentate ligand unit (e.g., pivalate), wherein at least one of the Q groups form a bond with M, and is defined such that each Q is independently selected from the group consisting of —O—, —NR—, —$CR_2$— and —S—;

G is either carbon or silicon; and Z is selected from the group consisting of R, —OR, —$NR_2$, —$CR_3$, —SR, —$SiR_3$, —$PR_2$, and hydride, providing that when Q is —NR—, then Z is selected from the group consisting of —OR, —$NR_2$, —SR, —$SiR_3$, —$PR_2$; and provided that neutral valency for Q is satisfied by Z; and wherein each R is independently selected from the group consisting of hydrocarbyls, lower hydrocarbyls, substituted hydrocarbyls, heterohydrocarbyls, alkyls, lower alkyls, substituted alkyls, heteroalkyls, alkenyls, lower alkenyls, substituted alkenyls, heteroalkenyls, alkynyls, lower alkynyls, substituted alkynyls, heteroalkynyls, alkoxys, lower alkoxys, aryloxys, hydroxyls, alkylthios, lower alkyls thios, arylthios, thioxys, aryls, substituted aryls, heteroaryls, aralkyls, aralkylenes, alkaryls, alkarylenes, halides, haloalkyls, haloalkenyls, haloalkynyls, heteroalkyls, heterocycles, heteroaryls, heteroatom-containing groups, silyls, boryls, phosphinos, phosphines, aminos, amines, cycloalkyls, acyls, aroyls, alkylthiols, dialkylamines, alkylamidos, alkoxycarbonyls, aryloxycarbonyls, carbomoyls, alkyl- and dialkyl-carbamoyls, acyloxys, acylaminos, aroylaminos, and combinations thereof. In another embodiment, R is selected from the group consisting of $C_1$ to $C_{10}$ heteroatom containing groups, $C_1$ to $C_{10}$ alkyls, $C_6$ to $C_{12}$ aryls, $C_6$ to $C_{12}$ alkylaryls, $C_1$ to $C_{10}$ alkoxys, and $C_6$ to $C_{12}$ aryloxys;

n is 1 or 2 in a particular embodiment; and

T is a bridging group selected from the group consisting of $C_1$ to $C_{10}$ alkylenes, $C_6$ to $C_{12}$ arylenes and $C_1$ to $C_{10}$ heteroatom containing groups, and $C_6$ to $C_{12}$ heterocyclic groups; wherein each T group bridges adjacent "$Cp^4M(Q_2GZ)X_n$" groups, and is chemically bonded to the $Cp^4$ groups.

m is an integer from 1 to 7; m is an integer from 2 to 6 in a more particular embodiment.

In another aspect, the at least one metallocene catalyst component can be described more particularly in structures (VIa), (VIb), (VIc), (VId), (VIe), and (VIf):

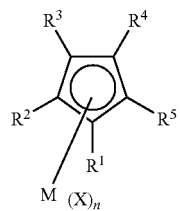

(VIa-i)

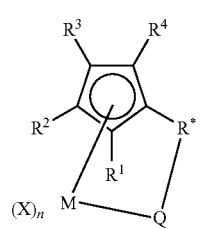

(VIa-ii)

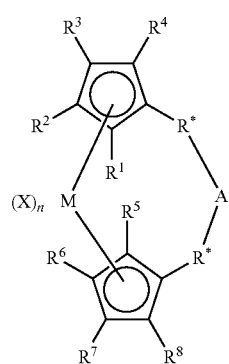

(VIb)

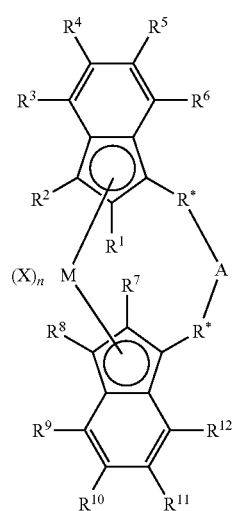

(VIc)

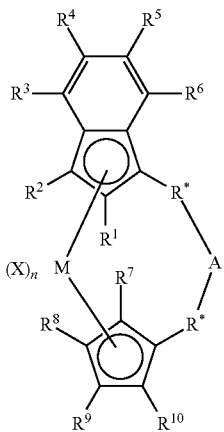

(VId)

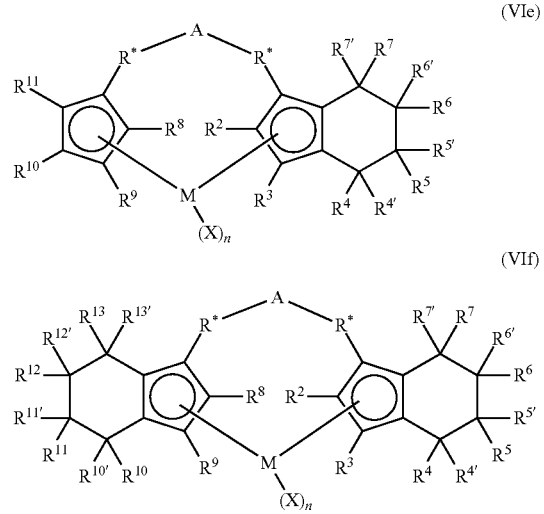

(VIe)

(VIf)

wherein in structures (VIa) to (VIf), M is selected from the group consisting of Group 3 to Group 12 atoms, and selected from the group consisting of Group 3 to Group 10 atoms in a more particular embodiment, and selected from the group consisting of Group 3 to Group 6 atoms in yet a more particular embodiment, and selected from the group consisting of Group 4 atoms in yet a more particular embodiment, and selected from the group consisting of Zr and Hf in yet a more particular embodiment; and is Zr in yet a more particular embodiment;

wherein Q in (VIa) to (VIf) is selected from the group consisting of hydrocarbyls, lower hydrocarbyls, substituted hydrocarbyls, heterohydrocarbyls, alkyls, lower alkyls, substituted alkyls, heteroalkyls, alkenyls, lower alkenyls, substituted alkenyls, heteroalkenyls, alkynyls, lower alkynyls, substituted alkynyls, heteroalkynyls, alkoxys, lower alkoxys, aryloxys, hydroxyls, alkylthios, lower alkyls thios, arylthios, thioxys, aryls, substituted aryls, heteroaryls, aralkyls, aralkylenes, alkaryls, alkarylenes, halides, haloalkyls, haloalkenyls, haloalkynyls, heteroalkyls, heterocycles, heteroaryls, heteroatom-containing groups, silyls, boryls, phosphinos, phosphines, aminos, amines, cycloalkyls, acyls, aroyls, alkylthiols, dialkylamines, alkylamidos, alkoxycarbonyls, aryloxycarbonyls, carbomoyls, alkyl- and dialkyl-carbamoyls, acyloxys, acylaminos, aroylaminos, alkylenes, aryls, arylenes, alkoxys, aryloxys, amines, arylamines (e.g., pyridyl) alkylamines, phosphines, alkylphosphines, substituted alkyls, substituted aryls, substituted alkoxys, substituted aryloxys, substituted amines, substituted alkylamines, substituted phosphines, substituted alkylphosphines, carbamates, heteroallyls, carboxylates (non-limiting examples of suitable carbamates and carboxylates include trimethylacetate, trimethylacetate, methylacetate, p-toluate, benzoate, diethylcarbamate, and dimethylcarbamate), fluorinated alkyls, fluorinated aryls, and fluorinated alkylcarboxylates; wherein the saturated groups defining Q comprise from 1 to 20 carbon atoms in one embodiment; and wherein the aromatic groups comprise from 5 to 20 carbon atoms in one embodiment; wherein R* may be selected from divalent alkyls, divalent lower alkyls, divalent substituted alkyls, divalent heteroalkyls, divalent alkenyls, divalent lower alkenyls, divalent substituted alkenyls, divalent heteroalkenyls, divalent alkynyls, divalent lower alkynyls, divalent substituted alkynyls, divalent heteroalkynyls, divalent alkoxys, divalent lower alkoxys, divalent aryloxys, divalent alkylthios, divalent lower alkyl thios, divalent arylthios, divalent aryls, divalent substituted aryls, divalent heteroaryls, divalent aralkyls, divalent aralkylenes, divalent alkaryls, divalent alkarylenes, divalent haloalkyls, divalent haloalkenyls, divalent haloalkynyls, divalent heteroalkyls, divalent heterocycles, divalent heteroaryls, divalent heteroatom-containing groups, divalent hydrocarbyls, divalent lower hydrocarbyls, divalent substituted hydrocarbyls, divalent heterohydrocarbyls, divalent silyls, divalent boryls, divalent phosphinos, divalent phosphines, divalent aminos, divalent amines, divalent ethers, divalent thioethers. Additionally, R* may be from the group of divalent hydrocarbylenes and heteroatom-containing hydrocarbylenes in one embodiment; and selected from the group consisting of alkylenes, substituted alkylenes and heteroatom-containing hydrocarbylenes in another embodiment; and selected from the group consisting of $C_1$ to $C_{12}$ alkylenes, $C_1$ to $C_{12}$ substituted alkylenes, and $C_1$ to $C_{12}$ heteroatom-containing hydrocarbylenes in a more particular embodiment; and selected from the group consisting of $C_1$ to $C_4$ alkylenes in yet a more particular embodiment; and wherein both R* groups are identical in another embodiment in structures (VIf);

A is as described above for (A) in structure (II), and more particularly, selected from the group consisting of a chemical bond, —O—, —S—, —SO$_2$—, —NR—, =SiR$_2$, =GeR$_2$, =SnR$_2$, —R$_2$SiSiR$_2$—, RP=, $C_1$ to $C_{12}$ alkylenes, substituted $C_1$ to $C_{12}$ alkylenes, divalent $C_4$ to $C_{12}$ cyclic hydrocarbons and substituted and unsubstituted aryl groups in one embodiment; and selected from the group consisting of $C_5$ to $C_8$ cyclic hydrocarbons, —CH$_2$CH$_2$—, =CR$_2$ and =SiR$_2$ in a more particular embodiment; wherein and R is selected from the group consisting of alkyls, cycloalkyls, aryls, alkoxys, fluoroalkyls and heteroatom-containing hydrocarbons in one embodiment; and R is selected from the group consisting of $C_1$ to $C_6$ alkyls, substituted phenyls, phenyl, and $C_1$ to $C_6$ alkoxys in a more particular embodiment; and R is selected from the group consisting of methoxy, methyl, phenoxy, and phenyl in yet a more particular embodiment; wherein A may be absent in yet another embodiment, in which case each R* is defined as for $R^1$-$R^{13}$; each X is as described above in (I); n is an integer from 0 to 4, and from 1 to 3 in another embodiment, and 1 or 2 in yet another embodiment; and $R^1$ through $R^{13}$ are independently: selected from the group consisting of hydrogen radicals, hydrocarbyls, lower hydrocarbyls, substituted hydrocarbyls, heterohydrocarbyls, alkyls, lower alkyls, substituted alkyls, heteroalkyls, alkenyls, lower alkenyls, substituted alkenyls, heteroalkenyls, alkynyls, lower alkynyls, substituted alkynyls, heteroalkynyls, alkoxys, lower alkoxys, aryloxys, hydroxyls, alkylthios, lower alkyls thios, arylthios, thioxys, aryls, substituted aryls, heteroaryls, aralkyls, aralkylenes, alkaryls, alkarylenes, halides, haloalkyls, haloalkenyls, haloalkynyls, heteroalkyls, heterocycles, heteroaryls, heteroatom-containing groups, silyls, boryls, phosphinos, phosphines, aminos, amines, cycloalkyls, acyls, aroyls, alkylthiols, dialkylamines, alkylamidos, alkoxycarbonyls, aryloxycarbonyls, carbomoyls, alkyl- and dialkyl-carbamoyls, acyloxys, acylaminos, aroylaminos. through $R^{13}$ may also be selected independently from $C_1$ to $C_{12}$ alkyls, $C_2$ to $C_{12}$ alkenyls, $C_6$ to $C_{12}$ aryls, $C_7$ to $C_{20}$ alkylaryls, $C_1$ to $C_{12}$ alkoxys, $C_1$ to $C_{12}$ fluoroalkyls, $C_6$ to $C_{12}$ fluoroaryls, and $C_1$ to $C_{12}$ heteroatom-containing hydrocarbons and substituted derivatives thereof in one embodiment; selected from the group consisting of hydrogen radical, fluorine radical, chlorine radical, bromine radical, $C_1$ to $C_6$ alkyls, $C_2$ to $C_6$ alkenyls, $C_7$ to $C_{18}$ alkylaryls, $C_1$ to $C_6$ fluoroalkyls, $C_2$ to $C_6$ fluoroalkenyls, $C_7$ to $C_{18}$ fluoroalkylaryls in a more particular embodiment; and hydrogen radical, fluorine radical, chlorine radical, methyl, ethyl, propyl, isopropyl, butyl, isobutyl, tertiary butyl, hexyl, phenyl, 2,6-dimethylpheyl, and 4-tertiarybutylpheyl groups in yet a more particular embodiment; wherein adjacent R groups may form a ring, either saturated, partially saturated, or completely saturated.

The structure of the metallocene catalyst component represented by (XIa) may take on many forms such as disclosed in, for example, U.S. Pat. Nos. 5,026,798, 5,703,187, and 5,747,406, including a dimmer or oligomeric structure, such as disclosed in, for example, U.S. Pat. Nos. 5,026,798 and 6,069,213.

In a particular embodiment of the metallocene represented in (VId), $R^1$ and $R^2$ form a conjugated 6-membered carbon ring system that may or may not be substituted.

Non-limiting examples of metallocene catalyst components consistent with the description herein include:
cyclopentadienylzirconium $X_n$,
indenylzirconium $X_n$,
(1-methylindenyl)zirconium $X_n$,
(2-methylindenyl)zirconium $X_n$,
(1-propylindenyl)zirconium $X_n$,
(2-propylindenyl)zirconium $X_n$,
(1-butylindenyl)zirconium $X_n$,
(2-butylindenyl)zirconium $X_n$,
(methylcyclopentadienyl)zirconium $X_n$,
tetrahydroindenylzirconium $X_n$,
(pentamethylcyclopentadienyl)zirconium $X_n$,
cyclopentadienylzirconium $X_n$,
pentamethylcyclopentadienyltitanium $X_n$,
tetramethylcyclopentyltitanium $X_n$,
1,2,4-trimethylcyclopentadienylzirconium $X_n$,
dimethylsilyl(1,2,3,4-tetramethylcyclopentadienyl)(cyclopentadienyl)zirconium $X_n$,
dimethylsilyl(1,2,3,4-tetramethylcyclopentadienyl)(1,2,3-trimethylcyclopentadienyl)zirconium $X_n$,
dimethylsilyl(1,2,3,4-tetramethylcyclopentadienyl)(1,2-dimethylcyclopentadienyl)zirconium $X_n$,
dimethylsilyl(1,2,3,4-tetramethyl-cyclopentadienyl)(2-methylcyclopentadienyl)zirconium $X_n$,
dimethylsilyl(cyclopentadienyl)(indenyl)zirconium $X_n$,
dimethylsilyl(2-methylindenyl)(fluorenyl)zirconium $X_n$,
diphenylsilyl(1,2,3,4-tetramethyl-cyclopentadienyl)(3-propylcyclopentadienyl)zirconium $X_n$,
dimethylsilyl(1,2,3,4-tetramethylcyclopentadienyl)(3-t-butylcyclopentadienyl)zirconium $X_n$,
dimethylgermyl(1,2-dimethylcyclopentadienyl)(3-isopropylcyclopentadienyl)zirconium $X_n$,
dimethylsilyl(1,2,3,4-tetramethyl-cyclopentadienyl)(3-methylcyclopentadienyl)zirconium $X_n$,
diphenylmethylidene(cyclopentadienyl)(9-fluorenyl)zirconium $X_n$,
diphenylmethylidene(cyclopentadienyl)(indenyl)zirconium $X_n$,
iso-propylidenebis(cyclopentadienyl)zirconium $X_n$,
iso-propylidene(cyclopentadienyl)(9-fluorenyl)zirconium $X_n$,
iso-propylidene(3-methylcyclopentadienyl)(9-fluorenyl)zirconium $X_n$,
ethylenebis(9-fluorenyl)zirconium $X_n$,
meso-ethylenebis(1-indenyl)zirconium $X_n$,
ethylenebis(1-indenyl)zirconium $X_n$,
ethylenebis(2-methyl-1-indenyl)zirconium $X_n$,
ethylenebis(2-methyl-4,5,6,7-tetrahydro-1-indenyl)zirconium $X_n$,
ethylenebis(2-propyl-4,5,6,7-tetrahydro-1-indenyl)zirconium $X_n$,
ethylenebis(2-isopropyl-4,5,6,7-tetrahydro-1-indenyl)zirconium $X_n$,
ethylenebis(2-butyl-4,5,6,7-tetrahydro-1-indenyl)zirconium $X_n$,
ethylenebis(2-isobutyl-4,5,6,7-tetrahydro-1-indenyl)zirconium $X_n$,
dimethylsilyl(4,5,6,7-tetrahydro-1-indenyl)zirconium $X_n$,
diphenyl(4,5,6,7-tetrahydro-1-indenyl)zirconium $X_n$,
ethylenebis(4,5,6,7-tetrahydro-1-indenyl)zirconium $X_n$,
dimethylsilylbis(cyclopentadienyl)zirconium $X_n$,
dimethylsilylbis(9-fluorenyl)zirconium $X_n$,
dimethylsilylbis(1-indenyl)zirconium $X_n$,
dimethylsilylbis(2-methylindenyl)zirconium $X_n$,
dimethylsilylbis(2-propylindenyl)zirconium $X_n$,
dimethylsilylbis(2-butylindenyl)zirconium $X_n$,
diphenylsilylbis(2-methylindenyl)zirconium $X_n$,
diphenylsilylbis(2-propylindenyl)zirconium $X_n$,
diphenylsilylbis(2-butylindenyl)zirconium $X_n$,
dimethylgermylbis(2-methylindenyl)zirconium $X_n$,
dimethylsilylbis(tetrahydroindenyl)zirconium $X_n$,
dimethylsilylbis(tetramethylcyclopentadienyl)zirconium $X_n$,
dimethylsilyl(cyclopentadienyl)(9-fluorenyl)zirconium $X_n$,
diphenylsilyl(cyclopentadienyl)(9-fluorenyl)zirconium $X_n$,
diphenylsilylbis(indenyl)zirconium $X_n$,
cyclotrimethylenesilyl(tetramethylcyclopentadienyl)(cyclopentadienyl) zirconium $X_n$,
cyclotetramethylenesilyl(tetramethylcyclopentadienyl)(cyclopentadienyl)zirconium $X_n$,
cyclotrimethylenesilyl(tetramethylcyclopentadienyl)(2-methylindenyl)zirconium $X_n$,
cyclotrimethylenesilyl(tetramethylcyclopentadienyl)(3-methylcyclopentadienyl)zirconium $X_n$,
cyclotrimethylenesilylbis(2-methylindenyl)zirconium $X_n$,
cyclotrimethylenesilyl(tetramethylcyclopentadienyl)(2,3,5-trimethylcyclopentadienyl)zirconium $X_n$,
cyclotrimethylenesilylbis(tetramethylcyclopentadienyl)zirconium $X_n$,
dimethylsilyl(tetramethylcyclopentadieneyl)(N-tert-butylamido)titanium bis(cyclopentadienyl)chromium $X_n$,
bis(cyclopentadienyl)zirconium $X_n$,
bis(n-butylcyclopentadienyl)zirconium $X_n$,
bis(n-dodecyclcyclopentadienyl)zirconium $X_n$,
bis(ethylcyclopentadienyl)zirconium $X_n$,
bis(iso-butylcyclopentadienyl)zirconium $X_n$,
bis(iso-propylcyclopentadienyl)zirconium $X_n$,
bis(methylcyclopentadienyl)zirconium $X_n$,
bis(n-oxtylcyclopentadienyl)zirconium $X_n$,
bis(n-pentylcyclopentadienyl)zirconium $X_n$,
bis(n-propylcyclopentadienyl)zirconium $X_n$, bis(trimethylsilylcyclopentadienyl)zirconium $X_n$,
bis(1,3-bis(trimethylsilyl)cyclopentadienyl)zirconium $X_n$,
bis(1-ethyl-2-methylcyclopentadienyl)zirconium $X_n$,
bis(1-ethyl-3-methylcyclopentadienyl)zirconium $X_n$,
bis(pentamethylcyclopentadienyl)zirconium $X_n$,
bis(pentamethylcyclopentadienyl)zirconium $X_n$,
bis(1-propyl-3-methylcyclopentadienyl)zirconium $X_n$,
bis(1-n-butyl-3-methylcyclopentadienyl)zirconium $X_n$,
bis(1-isobutyl-3-methylcyclopentadienyl)zirconium $X_n$,
bis(1-propyl-3-butylcyclopentadienyl)zirconium $X_n$,
bis(1,3-n-butylcyclopentadienyl)zirconium $X_n$,
bis(4,7-dimethylindenyl)zirconium $X_n$,
bis(indenyl)zirconium $X_n$,
bis(2-methylindenyl)zirconium $X_n$,
cyclopentadienylindenylzirconium $X_n$,
bis(n-propylcyclopentadienyl)hafnium $X_n$,
bis(n-butylcyclopentadienyl)hafnium $X_n$,
bis(n-pentylcyclopentadienyl)hafnium $X_n$,
(n-propyl cyclopentadienyl)(n-butyl cyclopentadienyl) hafnium $X_n$,
bis[(2-trimethylsilylethyl)cyclopentadienyl]hafnium $X_n$,
bis(trimethylsilyl cyclopentadienyl)hafnium $X_n$,
bis(2-n-propylindenyl)hafnium $X_n$,
bis(2-n-butylindenyl)hafnium $X_n$,
dimethylsilylbis(n-propylcyclopentadienyl)hafnium $X_n$,
dimethylsilylbis(n-butylcyclopentadienyl)hafnium $X_n$,
bis(9-n-propylfluorenyl)hafnium $X_n$,
bis(9-n-butylfluorenyl)hafnium $X_n$,
(9-n-propylfluorenyl)(2-n-propylindenyl)hafnium $X_n$,
bis(1-n-propyl-2-methylcyclopentadienyl)hafnium $X_n$,
(n-propylcyclopentadienyl)(1-n-propyl-3-n-butylcyclopentadienyl)hafnium $X_n$,
dimethylsilyl(tetramethylcyclopentadienyl)(cyclopropylamido)titanium $X_n$,
dimethylsilyl(tetramethyleyclopentadienyl)(cyclobutylamido)titanium $X_n$,
dimethylsilyl(tetramethyleyclopentadienyl)(cyclopentylamido)titanium $X_n$,
dimethylsilyl(tetramethylcyclopentadienyl)(cyclohexylamido)titanium $X_n$,
dimethylsilyl(tetramethylcyclopentadienyl)(cycloheptylamido)titanium $X_n$,
dimethylsilyl(tetramethylcyclopentadienyl)(cyclooctylamido)titanium $X_n$,
dimethylsilyl(tetramethylcyclopentadienyl)(cyclononylamido)titanium $X_n$,
dimethylsilyl(tetramethylcyclopentadienyl)(cyclodecylamido)titanium $X_n$,
dimethylsilyl(tetramethylcyclopentadienyl)(cycloundecylamido)titanium $X_n$,
dimethylsilyl(tetramethylcyclopentadienyl)(cyclododecylamido)titanium $X_n$,
dimethylsilyl(tetramethylcyclopentadienyl)(sec-butylamido)titanium $X_n$,
dimethylsilyl(tetramethylcyclopentadienyl)(n-octylamido) titanium $X_n$,
dimethylsilyl(tetramethylcyclopentadienyl)(n-decylamido) titanium $X_n$,
dimethylsilyl(tetramethylcyclopentadienyl)(n-octadecylamido)titanium $X_n$,
methylphenylsilyl(tetramethylcyclopentadienyl)(cyclopropylamido)titanium $X_n$,
methylphenylsilyl(tetramethylcyclopentadienyl)(cyclobutylamido)titanium $X_n$,
methylphenylsilyl(tetramethylcyclopentadienyl)(cyclopentylamido)titanium $X_n$,
methylphenylsilyl(tetramethylcyclopentadienyl)(cyclohexylamido)titanium $X_n$,
methylphenylsilyl(tetramethylcyclopentadienyl)(cycloheptylamido)titanium $X_n$,
methylphenylsilyl(tetramethylcyclopentadienyl)(cyclooctylamido)titanium $X_n$,
methylphenylsilyl(tetramethylcyclopentadienyl)(cyclononylamido)titanium, $X_n$,
methylphenylsilyl(tetramethylcyclopentadienyl)(cyclodecylamido)titanium, $X_n$,
methylphenylsilyl(tetramethylcyclopentadienyl)(cycloundecylamido)titanium $X_n$,
methylphenylsilyl(tetramethylcyclopentadienyl)(cyclododecylamido)titanium $X_n$,
methylphenylsilyl(tetramethylcyclopentadienyl)(sec-butylamido)titanium $X_n$,
methylphenylsilyl(tetramethylcyclopentadienyl)(n-octylamido)titanium methylphenylsilyl(tetramethylcyclopentadienyl)(n-decylamido)titanium $X_n$,
methylphenylsilyl(tetramethylcyclopentadienyl)(n-octadecylamido)titanium $X_n$,
diphenylsilyl(tetramethylcyclopentadienyl)(cyclopropylamido)titanium $X_n$,
diphenylsilyl(tetramethylcyclopentadienyl)(cyclobutylamido)titanium $X_n$,
diphenylsilyl(tetramethylcyclopentadienyl)(cyclopentylamido)titanium $X_n$,
diphenylsilyl(tetramethylcyclopentadienyl)(cyclohexylamido)titanium $X_n$,
diphenylsilyl(tetramethylcyclopentadienyl)(cycloheptylamido)titanium $X_n$,
diphenylsilyl(tetramethylcyclopentadienyl)(cyclooctylamido)titanium $X_n$,
diphenylsilyl(tetramethylcyclopentadienyl)(cyclononylamido)titanium $X_n$,
diphenylsilyl(tetramethylcyclopentadienyl)(cyclodecylamido)titanium $X_n$,
diphenylsilyl(tetramethylcyclopentadienyl)(cycloundecylamido)titanium $X_n$,
diphenylsilyl(tetramethylcyclopentadienyl)(cyclododecylamido)titanium $X_n$,
diphenylsilyl(tetramethylcyclopentadienyl)(sec-butylamido)titanium $X_n$,
diphenylsilyl(tetramethyleyclopentadienyl)(n-octylamido) titanium $X_n$,
diphenylsilyl(tetramethyleyclopentadienyl)(n-decylamido) titanium $X_n$,
diphenylsilyl(tetramethylcyclopentadienyl)(n-octadecylamido)titanium $X_n$,
and derivatives thereof.

In one non-limiting embodiment, the metallocene compound is selected from the group consisting of:
Pentamethylcyclopentadienyl)(Propyl cyclopentadienyl) $ZrX'_2$,
(Tetramethylcyclopentadienyl)(Propyl cyclopentadienyl) $ZrX'_2$,
(Pentamethylcyclopentadienyl)(Butyl cyclopentadienyl) $ZrX'_2$,
(Tetramethylcyclopentadienyl)(Butyl cyclopentadienyl) $ZrX'_2$,
Me2Si(Indenyl)$_2$ZrX$_2$, Me2Si(Tetrahydroindenyl)$_2$ZrX'$_2$,
(n-propyl cyclopentadienyl)$_2$ZrX'$_2$,
(n-propyl cyclopentadienyl)$_2$HfX'$_2$,
(n-butyl cyclopentadienyl)$_2$ZrX'$_2$,
(n-butyl cyclopentadienyl)$_2$HfX'$_2$,
(1-Methyl, 3-Butyl cyclopentadienyl)$_2$ZrX'$_2$, HN(CH2CH2N(2,4,6-Me3Phenyl))$_2$ZrX'$_2$,
HN(CH2CH2N(2,3,4,5,6-Me5-Phenyl))$_2$ZrX'$_2$,
(1-Me, 3-Bu-Cp)$_2$ZrCl$_2$,
(CpPr)(Me4 Cp)HfCl$_2$,
(CpBu)$_2$ZrCl$_2$,
(CpPr)$_2$ZrCl$_2$,
(CpBu)$_2$HfCl$_2$,
(CpPr)$_2$HfCl$_2$,
and combinations comprising at least one of the above metallocene compounds.

In an embodiment, the metallocene is represented by the formula:

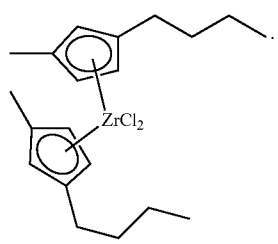

By "derivatives thereof", it is meant any substitution or ring formation as described above; and in particular, replacement of the metal "M" (Cr, Zr, Ti or Hf) with an atom selected from the group consisting of Cr, Zr, Hf and Ti; and replacement of the "X" group with any of $C_1$ to $C_5$ alkyls, $C_6$ aryls, $C_6$ to $C_{10}$ alkylaryls, fluorine or chlorine; n is 1, 2 or 3.

It is contemplated that the metallocene catalysts components described above include their structural or optical or enantiomeric isomers (racemic mixture), and may be a pure enantiomer in one embodiment.

As used herein, a single, bridged, asymmetrically substituted metallocene catalyst component having a racemic and/or meso isomer does not, itself, constitute at least two different bridged, metallocene catalyst components.

The "metallocene catalyst component" may comprise any combination of any "embodiment" described herein.

Metallocene compounds and catalysts are known in the art and any one or more may be utilized herein. Suitable metallocenes include but are not limited to all of the metallocenes disclosed and referenced in the U.S. patents cited above, as well as those disclosed and referenced in U.S. Pat. Nos. 7,179,876, 7,169,864, 7,157,531, 7,129,302, 6,995,109, 6,958,306, 6,884748, 6,689,847, U.S. Patent Application publication number 2007/0055028, and published PCT Application Nos. WO 97/22635, WO 00/699/22, WO 01/30860, WO 01/30861, WO 02/46246, WO 02/50088, WO 04/026921, and WO 06/019494, all fully incorporated herein by reference for the teachings directed to metallocene catalysts. Additional catalysts suitable for use herein include those referenced in U.S. Pat. Nos. 6,309,997, 6,265,338, U.S. Patent Application publication number 2006/019925, and the following articles: Chem Rev 2000, 100, 1253, Resconi; Chem Rev 2003, 103, 283; Chem Eur. J. 2006, 12, 7546 Mitsui; J Mol Catal A 2004, 213, 141; Macromol Chem Phys, 2005, 206, 1847; and J Am Chem Soc 2001, 123, 6847 all of which are fully incorporated herein by reference for the teachings directed to metallocene catalysts.

Phenoxide Transition Metal Catalysts

Phenoxide transition metal catalyst compositions are heteroatom substituted phenoxide ligated Group 3 to 10 transition metal or lanthanide metal compounds wherein the metal is bound to the oxygen of the phenoxide group. Phenoxide transition metal catalyst compounds may be represented by Formula XIV or XV:

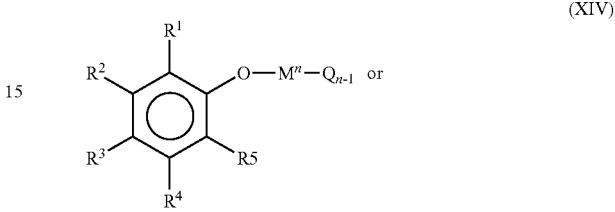

(XIV)

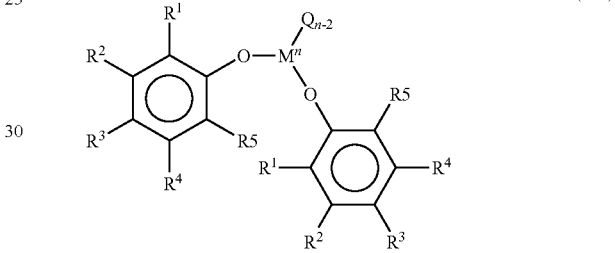

(XV)

wherein $R^1$ is hydrogen or a $C_4$ to $C_{100}$ group, preferably a tertiary alkyl group, preferably a $C_4$ to $C_{20}$ alkyl group, preferably a $C_4$ to $C_{20}$ tertiary alkyl group, preferably a neutral $C_4$ to $C_{100}$ group and may or may not also be bound to M;

at least one of $R^2$ to $R^5$ is a heteroatom containing group, the rest of $R^2$ to $R^5$ are independently hydrogen or a $C_1$ to $C_{100}$ group, preferably a $C_4$ to $C_{20}$ alkyl group, preferred examples of which include butyl, isobutyl, t-butyl, pentyl, hexyl, heptyl, isohexyl, octyl, isooctyl, decyl, nonyl, dodecyl, and any of $R^2$ to $R^5$ also may or may not be bound to M;

Each $R^1$ to $R^5$ group may be independently substituted or unsubstituted with other atoms, including heteroatoms or heteroatom containing group(s);

O is oxygen;

M is a Group 3 to Group 10 transition metal or lanthanide metal, preferably a Group 4 metal, preferably M is Ti, Zr or Hf;

n is the valence state of the metal M, preferably 2, 3, 4, or 5; and

Q is, and each Q may be independently be, an alkyl, halogen, benzyl, amide, carboxylate, carbamate, thiolate, hydride or alkoxide group, or a bond to an R group containing a heteroatom which may be any of $R^1$ to $R^5$.

A heteroatom containing group may be any heteroatom or a heteroatom bound to carbon, silicon or another heteroatom. Preferred heteroatoms include boron, aluminum, silicon, nitrogen, phosphorus, arsenic, tin, lead, antimony, oxygen, selenium, and tellurium. Particularly preferred heteroatoms include nitrogen, oxygen, phosphorus, and sulfur. Even more particularly preferred heteroatoms include nitrogen and oxygen. The heteroatom itself may be directly bound to the phenoxide ring or it may be bound to another atom or atoms that are bound to the phenoxide ring. The heteroatom containing group may contain one or more of the same or different heteroatoms. Preferred heteroatom containing groups include imines, amines, oxides, phosphines, ethers, ketones, oxoazolines heterocyclics, oxazolines, thioethers, and the like. Particularly preferred heteroatom containing groups include imines. Any two adjacent R groups may form a ring structure, preferably a 5 or 6 membered ring. Likewise the R groups may form multi-ring structures. In one embodiment any two or more R groups do not form a 5 membered ring.

In a preferred embodiment the heteroatom substituted phenoxide transition metal compound is an iminophenoxide Group 4 transition metal compound, and more preferably an iminophenoxidezirconium compound.

In an embodiment, the phenoxide transition metal catalyst is a biphenyl phenol catalyst as described herein. It is further contemplated by the invention that other catalysts can be combined with the compounds of the invention. For example, see Hlalky, G. G. *Chem. Rev.* (2000), 100, 1347; Alt, H.; Koppl, A. *Chem. Rev.* (2000), 100, 1205; Resconi, L. et al., *Chem. Rev.* (2000), 100, 1253; Bryntzinger, H. H. et. al., *Angew. Chem. Int. Ed. Engl.* (1995), 34, 1143; Ittel, S. D. et al., *Chem. Rev.* (2000), 100, 1169; Gibson, V. C. et al., *Chem. Rev.* (2003), 103, 283; Skupinska, J., *Chem. Rev.* (1991), 91, 613; Carter, A. et al., *Chem. Commun.* 2002, 858; McGuinness, D. S.; et al., *J. Am. Chem. Soc.* (2003), 125, 5272; McGuiness, D. S., *Chem. Commun.* (2003), 334; U.S. Pat. Nos. 4,937,299, 4,935,474, 5,281,679, 5,359,015, 5,470,811, and 5,719,241, all of which are herein fully incorporated herein by reference for teachings directed to phenoxide transition metal catalysts.

In another embodiment of the invention one or more catalyst compounds or catalyst systems may be used in combination with one or more conventional-type catalyst compounds or catalyst systems. Non-limiting examples of mixed catalysts and catalyst systems are described in U.S. Pat. Nos. 4,159,965, 4,325,837, 4,701,432, 5,124,418, 5,077,255, 5,183,867, 5,391,660, 5,395,810, 5,691,264, 5,723,399 and 5,767,031, and PCT Publication No. WO 96/23010 published Aug. 1, 1996, all of which are herein fully incorporated herein by reference for teachings directed to phenoxide transition metal catalysts.

High Molecular Weight Catalysts

With respect to the catalyst systems of the disclosure wherein the high molecular weight catalyst compound is a non-metallocene compound generally the compound is a phenoxide transition metal catalyst which is biphenyl phenol catalyst (BPP) compound. BPP catalyst compounds are known in the art and any are suitable for use herein such as, but not limited to those disclosed in U.S. Pat. Nos. 7,091,282, 7,030,256, 7,060,848, 7,126,031, 6,841,502, U.S. Patent Application publication numbers 2006/0025548, 2006/020588, 2006/00211892, and published PCT application numbers WO 2006/020624, WO 2005/108406, and WO 2003/091262, all incorporated herein by reference for teachings directed to biphenyl phenol transition metal catalysts.

In a preferred embodiment, the BPP compounds have the formula (XVI) shown below:

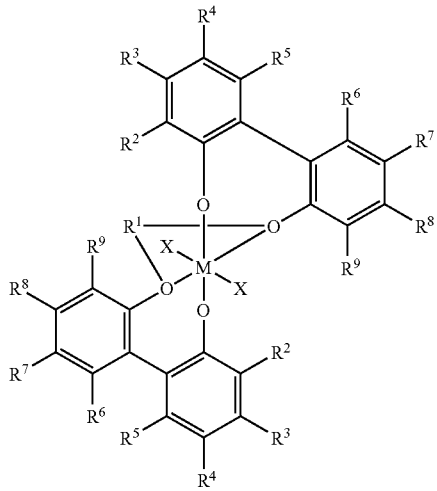

formula XVI wherein M may be Ti, Zr, or Hf. In one embodiment $R^1$ of formula 1 is hydride, hydrocarbyl, lower hydrocarbyl, substituted hydrocarbyl, heterohydrocarbyl, alkyl, lower alkyl, substituted alkyl, heteroalkyl, alkenyl, lower alkenyl, substituted alkenyl, heteroalkenyl, alkynyl, lower alkynyl, substituted alkynyl, heteroalkynyl, alkoxy, lower alkoxy, aryloxy, hydroxyl, alkylthio, lower alkyl thio, arylthio, thioxy, aryl, substituted aryl, heteroaryl, aralkyl, aralkylene, alkaryl, alkarylene, halide, haloalkyl, haloalkenyl, haloalkynyl, heteroalkyl, heterocycle, heteroaryl, heteroatom-containing group, silyl, boryl, phosphino, phosphine, amino, amine.

In some embodiments, the bridging group $R^1$ is selected from the group consisting of optionally substituted divalent hydrocarbyl and divalent heteroatom containing hydrocarbyl. In other embodiments, $R^1$ is selected from the group consisting of optionally substituted divalent alkyl, divalent lower alkyl, divalent substituted alkyl, divalent heteroalkyl, divalent alkenyl, divalent lower alkenyl, divalent substituted alkenyl, divalent heteroalkenyl, divalent alkynyl, divalent lower alkynyl, divalent substituted alkynyl, divalent heteroalkynyl, divalent alkoxy, divalent lower alkoxy, divalent aryloxy, divalent alkylthio, divalent lower alkyl thio, divalent arylthio, divalent aryl, divalent substituted aryl, divalent heteroaryl, divalent aralkyl, divalent aralkylene, divalent alkaryl, divalent alkarylene, divalent halide, divalent haloalkyl, divalent haloalkenyl, divalent haloalkynyl, divalent heteroalkyl, divalent heterocycle, divalent heteroaryl, divalent heteroatom-containing group, divalent hydrocarbyl, divalent lower hydrocarbyl, divalent substituted hydrocarbyl, divalent heterohydrocarbyl, divalent silyl, divalent boryl, divalent phosphino, divalent phosphine, divalent amino, divalent amine, divalent ether, divalent thioether. In still other embodiments, $R^1$ can be represented by the general formula -$(Q''R^{40}_{2-z''})_{z'}$— wherein each Q'' is either carbon or silicon and each $R^{40}$ may be the same or different from the others such that each $R^{40}$ is selected from the group consisting of hydride and optionally substituted hydrocarbyl, and optionally two or more $R^{40}$ groups may be joined into a ring structure having from 3 to 50 atoms in the ring structure (not counting hydrogen atoms); and z' is an integer from 1 to 10, more specifically from 15 and even more specifically from 25 and z'' is 0, 1 or 2. For example, when z'' is 2, there is no $R^{40}$ groups associated with Q'', which allows for those cases where one Q'' is multiply bonded to a second Q''. In more specific embodiments, $R^{40}$ is selected from the group consisting of hydride, halide, and optionally substituted alkyl, alkenyl, alkynyl, heteroalkyl, heteroalkenyl, heteroalkynyl, aryl, heteroaryl, alkoxyl, aryloxyl, silyl, boryl, phosphino, amino, thioxy, alkylthio, arylthio, and combinations thereof. Specific $R^1$ groups within these embodiments include —$(CH_2)_2$—, —$(CH_2)_3$—, —$(CH_2)_4$— and —$(CH_2)$—$(C_6H_4)$—$(CH_2)$—. Other specific bridging moieties are set forth in the example ligands and complexes herein.

In one embodiment $R^2$-$R^9$ of formula (XVI) are optionally hydrocarbyl, lower hydrocarbyl, substituted hydrocarbyl, heterohydrocarbyl, alkyl, lower alkyl, substituted alkyl, heteroalkyl, alkenyl, lower alkenyl, substituted alkenyl, heteroalkenyl, alkynyl, lower alkynyl, substituted alkynyl, heteroalkynyl, alkoxy, lower alkoxy, aryloxy, hydroxyl, alkylthio, lower alkyl thio, arylthio, thioxy, aryl, substituted aryl, heteroaryl, aralkyl, aralkylene, alkaryl, alkarylene, halide, haloalkyl, haloalkenyl, haloalkynyl, heteroalkyl, heterocycle, heteroaryl, heteroatom-containing group, silyl, boryl, phosphino, phosphine, amino, or amine.

Each X in formula (XVI) is independently selected from the group consisting of: any leaving group in one embodiment; halogen ions, hydrides, $C_1$ to $C_{12}$ alkyls, $C_2$ to $C_{12}$ alkenyls, $C_6$ to $C_{12}$ aryls, $C_7$ to $C_{20}$ alkylaryls, $C_1$ to $C_{12}$ alkoxys, $C_6$ to $C_{16}$ aryloxys, $C_7$ to $C_{18}$ alkylaryloxys, $C_1$ to $C_{12}$ fluoroalkyls, $C_6$ to $C_{12}$ fluoroaryls, and $C_1$ to $C_{12}$ heteroatom-containing hydrocarbons and substituted derivatives thereof in a more particular embodiment; hydride, halogen ions, $C_1$ to $C_6$ alkyls, $C_2$ to $C_6$ alkenyls, $C_7$ to $C_{18}$ alkylaryls, $C_1$ to $C_6$ alkoxys, $C_6$ to $C_{14}$ aryloxys, $C_7$ to $C_{16}$ alkylaryloxys, $C_1$ to $C_6$ alkylcarboxylates, $C_1$ to $C_6$ fluorinated alkylcarboxylates, $C_6$ to $C_{12}$ arylcarboxylates, $C_7$ to $C_{18}$ alkylarylcarboxylates, $C_1$ to $C_6$ fluoroalkyls, $C_2$ to $C_6$ fluoroalkenyls, and $C_7$ to $C_{18}$ fluoroalkylaryls in yet a more particular embodiment; hydride, chloride, fluoride, methyl, phenyl, phenoxy, benzoxy, tosyl, fluoromethyls and fluorophenyls in yet a more particular embodiment; $C_1$ to $C_{12}$ alkyls, $C_2$ to $C_{12}$ alkenyls, $C_6$ to $C_{12}$ aryls, $C_7$ to $C_{20}$ alkylaryls, substituted $C_1$ to $C_{12}$ alkyls, substituted $C_6$ to $C_{12}$ aryls, substituted $C_7$ to $C_{20}$ alkylaryls and $C_1$ to $C_{12}$ heteroatom-containing alkyls, $C_1$ to $C_{12}$ heteroatom-containing aryls and $C_1$ to $C_{12}$ heteroatom-containing alkylaryls in yet a more particular embodiment; chloride, fluoride, $C_1$ to $C_6$ alkyls, $C_2$ to $C_6$ alkenyls, $C_7$ to $C_{18}$ alkylaryls, halogenated $C_1$ to $C_6$ alkyls, halogenated $C_2$ to $C_6$ alkenyls, and halogenated $C_7$ to $C_{18}$ alkylaryls in yet a more particular embodiment; fluoride, methyl, ethyl, propyl, phenyl, methylphenyl, dimethylphenyl, trimethylphenyl, fluoromethyls (mono-, di- and trifluoromethyls) and fluorophenyls (mono-, di-, tri-, tetra- and pentafluorophenyls) in yet a more particular embodiment.

Other non-limiting examples of X groups in formula (XVI) include amines, phosphines, ethers, carboxylates, dienes, hydrocarbon radicals having from 1 to 20 carbon atoms, fluorinated hydrocarbon radicals (e.g., —$C_6F_5$ (pentafluorophenyl)), fluorinated alkylcarboxylates (e.g., $CF_3C(O)O^-$), hydrides and halogen ions and combinations thereof. Other examples of X ligands include alkyl groups such as cyclobutyl, cyclohexyl, methyl, heptyl, tolyl, trifluoromethyl, tetramethylene, pentamethylene, methylidene, methyoxy, ethyoxy, propoxy, phenoxy, bis(N-methylanilide), dimethylamide, dimethylphosphide radicals and the like. In one embodiment, two or more X's form a part of a fused ring or ring system.

In one embodiment of the compound represented by formula (XVI), M may be Ti, Zr, or Hf. $R^1$, $R^3$, $R^5$ through $R^9$ are H; each $R^2$ may be any of alkyl, aryl, or heteroaryl; each $R^4$ may be any of H, alkyl, aryl, or heteroaryl; and each X may be any of F, Cl, Br, I, Me, Bnz, $CH_2SiMe_3$, or $C_1$ to $C_5$ alkyls.

In another non-limiting embodiment of the compound represented by formula (XVI), M may be Ti, Zr, or Hf; $R^1$ may be any of $CH_2CH_2$, $(CH_2)_3$, $(CH_2)_4$, $CH_2CHMeCH_2$, $CH_2CMe_2CH_2$, $Me_2S_1$, $CH_2SiMe_2CH_2$, each $R^2$ may be any of an aryl group, defined here to bind through the 1-position to the BPP ring, with substituents in the 2-position or substituents in the 2 and 6 positions such as 2,4-$Me_2$Ph, 2,5-$Me_2$Ph, 2,6-$Me_2$Ph, 2,6-$Et_2$Ph, 2,6-$Pr_2$-Ph, 2,6-$Bu_2$Ph, 2-MeNapthyl, 2,4,6-$Me_3$Ph, 2,4,6-$Et_3$Ph, 2,4,6-$Pr_3$Ph, carbazole and substituted carbazoles; $R^3$ and $R^5$ through $R^9$ are H; each $R^4$ may be any of H, Methyl, Ethyl, Propyl, Butyl, Pentyl; and each X may be any of F, Cl, Br, I, Me, Bnz, $CH_2SiMe_3$, or $C_1$ to $C_5$ alkyls.

In one preferred embodiment, M may be either Zr or Hf, and X may be any of F, Cl, Br, I, Me, Bnz, or $CH_2SiMe_3$. In another preferred embodiment, M may be either Zr or Hf, $R^1$ may be either $(CH_2)_3$ or $(CH_2)_4$; each $R^2$ may be any of 2,6-Me2Ph, 2,6-Et2Ph, 2,6-Pr2-Ph, 2,6-Bu2Ph, 2-MeNapthyl, 2,4,6-Me3Ph, 2,4,6-Et3Ph, 2,4,6-Pr3Ph, and carbazole; each $R^4$ may be any of H, Methyl or Butyl; and X may be any of F, Cl, or Me. In even another preferred embodiment, the $R^1$ is $(CH_2)_3$; each $R^3$ is either 2,4,6-Me3Ph or 2-MeNapthyl; each $R^4$ is $CH_3$; X is Cl; and M is Zr.

In a preferred embodiment, the phenoxide transition metal catalyst is a biphenyl phenol catalyst represented by the formula:

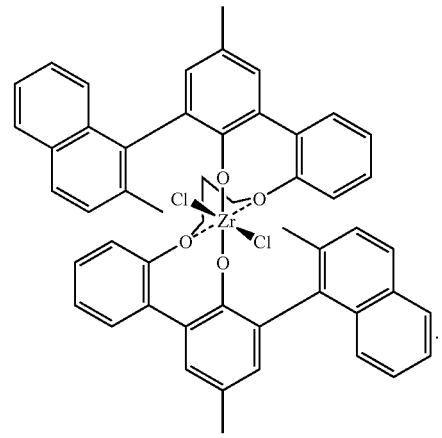

In another non-limiting embodiment, the high molecular weight catalyst component may be any catalyst that produces a polymer having a weight average molecular weight (Mw) of greater than about 1 million g/mol, preferably greater than about 1.5 million g/mol, even more preferably greater than about 2 million g/mol, and still more preferably greater than about 3 million g/mol. The low molecular weight catalyst may be any catalyst that produces a polymer having a weight average molecular weight (Mw) in the range of from about 40,000 to about 200,000 g/mol, preferably from about 50,000 to about 180,000 g/mol, more preferably from about 60,000 to about 175,000 g/mol, and even more preferably from about 70,000 to about 150,000 g/mol. In one preferred embodiment, the high molecular weight catalyst produces polymer having an Mw greater than about 5 million g/mol, and the low molecular weight catalyst produces polymer having an Mw of about 100,000 g/mol.

The amount of each catalyst component present in the catalyst systems of the disclosure may be varied within a range. The amount of each catalyst component present in the catalyst systems may be dependent on one or more reaction parameters including but not limited to reactor temperature, hydrogen concentration, and comonomer concentration. The low molecular weight catalyst is generally present in an amount greater than that of the high molecular weight catalyst. Generally, the high molecular weight catalyst component is present in a catalyst system in an amount in a range of from about 0.001 to about 5.0 mol % of said low molecular weight catalyst component, preferably in a range of from about 0.05 to about 2.5 mol % of said low molecular weight catalyst component, more preferably in a range of from about 0.1 to about 2.0 mol % of said low molecular weight catalyst component, more preferably the high molecular weight catalyst component is present in a catalyst system in an amount of greater than or equal to about 0.4 mol % to less than or equal to about 2.0 mol % of the low molecular weight catalyst component, more preferably the high molecular weight catalyst component is present in a catalyst system in an amount of greater than or equal to about 0.8 mol % to less than or equal to about 2.0 mol % of the low molecular weight catalyst component, more preferably the high molecular weight catalyst component is present in a catalyst system in an amount of greater than or equal to about 1.2 mol % to less than or equal to about 1.5 mol % of the low molecular weight catalyst component. For example, in the case of one high and one low molecular weight catalyst, the mol % of the high molecular weight catalyst may be calculated from the equation: 100 (moles of high molecular weight catalyst)/(moles of low molecular weight catalyst+moles of high molecular weight catalyst).

Activators and Activation Methods

The above described low and high molecular weight precatalyst compounds can be combined with an activator and optionally a support or carrier in a manner that will allow production of a polymer with low and high molecular weight components. The term "cocatalyst" or "cocatalysts" may be used interchangeably with one or more "activators". This activation yields catalyst compounds capable of polymerizing olefins.

For the purposes of this patent specification and appended claims, the term "activator" is defined to be any compound or component or method which can activate any of the precatalyst metal compounds of the invention as described above. Non-limiting activators, for example may include a Lewis acid or a non-coordinating ionic activator or ionizing activator or any other compound including Lewis bases, aluminum alkyls, conventional-type cocatalysts or an activator-support and combinations thereof that can convert a neutral precatalyst metal compound to a catalytically active cationic metal compound. It is within the scope of this invention to use alumoxane or modified alumoxane as an activator, and/or to also use ionizing activators, neutral or ionic, such as tri(n-butyl)ammonium tetrakis(pentafluorophenyl)boron or a trisperfluorophenyl boron metalloid precursor or a trisperfluoronaphtyl boron metalloid precursor that would ionize the neutral precatalyst metal compound.

The low and high molecular weight catalyst precursors according to this invention may be activated for polymerization catalysis in any manner sufficient to allow coordination or cationic polymerization. This can be achieved for coordination polymerization when one ligand can be abstracted and another will either allow insertion of the unsaturated monomers or will be similarly abstractable for replacement with a ligand that allows insertion of the unsaturated monomer (labile ligands), e.g. alkyl, silyl or hydride. The traditional activators of coordination polymerization art are suitable, those typically include Lewis acids such as alumoxane compounds, and ionizing, anion precursor compounds that abstract one so as to ionize the bridged metallocene metal center in to a cation and provide a counterbalancing noncoordinating ion. In one embodiment, an activation method using ionizing ionic compounds not containing an active proton but capable of producing both a cationic metal compound catalyst and a non-coordinating anion are also contemplated, and are described in EP-A-0 426 637, EP-A-0 573 403 and U.S. Pat. No. 5,387, 568, which are all herein incorporated by reference.

Alkylalumoxanes and modified alkylalumoxane are suitable as catalyst activators, particularly for the invention metal compounds where $R^1$=halide or other functional group. Alkylalumoxanes and modified alkylalumoxane are also suitable as catalyst for the invention metal compounds where $R^1$=hydrocarbyl or substituted hydrocarbyl. In one embodiment, one or more alumoxanes are utilized as an activator in the catalyst composition of the invention. Alumoxanes, sometimes called aluminoxanes in the art, are generally oligomeric compounds containing —Al(R)—O— subunits, where R is an alkyl group. Examples of alumoxanes include methylalumoxane (MAO), modified methylalumoxane (MMAO), ethylalumoxane and isobutylalumoxane. Alkylalumoxanes and modified alkylalumoxanes are suitable as catalyst activators, particularly when the abstractable ligand is a halide. Mixtures of different alumoxanes and modified alumoxanes may also be used. For further descriptions, see U.S. Pat. Nos. 4,665, 208, 4,952,540, 5,041,584, 5,091,352, 5,206,199, 5,204,419, 4,874,734, 4,924,018, 4,908,463, 4,968,827, 5,329,032, 5,248,801, 5,235,081, 5,157,137, 5,103,031 and EP 0 561 476 A1, EP 0279586 B1, EP 0516476 A, EP 0594218 A1 and WO 94/10180.

Alumoxanes may be produced by the hydrolysis of the respective trialkylaluminum compound. MMAO may be produced by the hydrolysis of trimethylaluminum and a higher trialkylaluminum such as triisobutylaluminum. MMAO's are generally more soluble in aliphatic solvents and more stable during storage. There are a variety of methods for preparing alumoxane and modified alumoxanes, non-limiting examples of which are described in U.S. Pat. Nos. 4,665,208, 4,952, 540, 5,091,352, 5,206,199, 5,204,419, 4,874,734, 4,924,018, 4,908,463, 4,968,827, 5,308,815, 5,329,032, 5,248,801, 5,235,081, 5,157,137, 5,103,031, 5,391,793, 5,391,529, 5,693,838, 5,731,253, 5,731,451, 5,744,656, 5,847,177, 5,854,166, 5,856,256 and 5,939,346 and European publications EP-A-0 561 476, EP-B1-0 279 586, EP-A-0 594-218 and EP-B1-0 586 665, and PCT publications WO 94/10180 and WO 99/15534, all of which are herein fully incorporated by reference. It may be preferable to use a visually clear methylalumoxane. A cloudy or gelled alumoxane can be filtered to produce a clear solution or clear alumoxane can be decanted from the cloudy solution. Another preferred alumoxane is a modified methyl alumoxane (MMAO) cocatalyst type 3A (commercially available from Akzo Chemicals, Inc. under the trade name Modified Methylalumoxane type 3A, covered under U.S. Pat. No. 5,041,584).

Aluminum alkyl or organoaluminum compounds which may be utilized as activators (or scavengers) include trimethylaluminum, triethylaluminum, triisobutylaluminum, tri-n-hexylaluminum, tri-n-octylaluminum and the like.

It is within the scope of this invention to use an ionizing or stoichiometric activator, neutral or ionic, such as tri(n-butyl) ammonium tetrakis (pentafluorophenyl) boron, a trisperfluorophenyl boron metalloid precursor or a trisperfluoronaphtyl boron metalloid precursor, polyhalogenated heteroborane anions (WO 98/43983), boric acid (U.S. Pat. No. 5,942,459) or combination thereof. It is also within the scope of this invention to use neutral or ionic activators alone or in combination with alumoxane or modified alumoxane activators.

Examples of neutral stoichiometric activators include trisubstituted boron, tellurium, aluminum, gallium and indium or mixtures thereof. The three substituent groups are each independently selected from alkyls, alkenyls, halogen, substituted alkyls, aryls, arylhalides, alkoxy and halides. Preferably, the three groups are independently selected from halogen, mono or multicyclic (including halosubstituted) aryls, alkyls, and alkenyl compounds and mixtures thereof, preferred are alkenyl groups having 1 to 20 carbon atoms, alkyl groups having 1 to 20 carbon atoms, alkoxy groups having 1 to 20 carbon atoms and aryl groups having 3 to 20 carbon atoms (including substituted aryls). More preferably, the three groups are alkyls having 1 to 4 carbon groups, phenyl, naphthyl or mixtures thereof. Even more preferably, the three groups are halogenated, preferably fluorinated, aryl groups. Most preferably, the neutral stoichiometric activator is trisperfluorophenyl boron or trisperfluoronaphthyl boron.

Ionic stoichiometric activator compounds may contain an active proton, or some other cation associated with, but not coordinated to, or only loosely coordinated to, the remaining ion of the ionizing compound. Such compounds and the like are described in European publications EP-A-0 570 982, EP-A-0 520 732, EP-A-0 495 375, EP-B1-0 500 944, EP-A-0 277 003 and EP-A-0 277 004, and U.S. Pat. Nos. 5,153,157, 5,198,401, 5,066,741, 5,206,197, 5,241,025, 5,384,299 and 5,502,124 and U.S. patent application Ser. No. 08/285,380, filed Aug. 3, 1994, all of which are herein fully incorporated by reference.

Preferred activators include a cation and an anion component, and may be represented by the following formula:

$$(S'^+)_u(NCA^{v-})$$

$S'^+$ is a cation component having the charge $t+$
$NCA^{v-}$ is a non-coordinating anion having the charge $v-$
  t is an integer from 1 to 3.
  v is an integer from 1 to 3.
  u and v are constrained by the relationship: $(u)\times(t)=(v)\times(w)$.

The cation component, $(S'^+)$ may include Bronsted acids such as protons or protonated Lewis bases or reducible Lewis acids capable of protonating or abstracting a moiety, such as an alkyl or aryl, from an analogous metallocene or Group 15 containing transition metal catalyst precursor, resulting in a cationic transition metal species.

In a preferred embodiment, the activators include a cation and an anion component, and may be represented by the following formula:

$$(LB-H'^+)_u(NCA^{v-})_w$$

wherein LB is a neutral Lewis base;
H is hydrogen;
$NCA^{v-}$ is a non-coordinating anion having the charge $v-$
  t is an integer from 1 to 3,
  v is an integer from 1 to 3,
  u and v are constrained by the relationship: $(u)\times(t)=(v)\times(w)$.

The activating cation $(S'^+)$ may be a Bronsted acid, $(LB-H'^+)$, capable of donating a proton to the transition metal catalytic precursor resulting in a transition metal cation, including ammoniums, oxoniums, phosphoniums, silyliums and mixtures thereof, preferably ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxoniums from ethers such as dimethyl ether diethyl ether, tetrahydrofuran and dioxane, sulfoniums from thioethers, such as diethyl thioethers and tetrahydrothiophene and mixtures thereof.

Ionizing compounds may contain an active proton, or some other cation associated with but not coordinated to or only loosely coordinated to the remaining ion of the ionizing compound. Such compounds and the like are described in European Publication Nos. EP-A-0 570 982, EP-A-0 520 732, EP-A-0 495 375, EP-A-500 944, EP-A-0 277 003 and EP-A-0 277 004, U.S. Pat. Nos. 5,153,157, 5,198,401, 5,066,741, 5,206,197, 5,241,025, 5,384,299 and 5,502,124, and U.S. patent application Ser. No. 08/285,380, filed Aug. 3, 1994, all of which are herein fully incorporated by reference.

The activating cation $(S'^+)$ may also be an abstracting moiety such as silver, carbeniums, carbyliums, tropylium, ferroceniums and mixtures, preferably carbeniums. (Carbeniums are defined as carbon based cations with one less substituent than the corresponding neutral atom, sometimes referred to a carbonium ions, while carbyliums are defined as carbon based cations with one more substituent, generally H, than the corresponding neutral atom.)

Most preferably $(S'^+)$ is triphenyl carbenium or N,N-dimethylanilinium.

The anion component $(NCA^{v-})$ includes those having the formula $[T^{x+}Q_y]^{v-}$ wherein x is an integer from 1 to 3; y is an integer from 2 to 6; $y-x=v$; T is an element selected from Group 13 or 15 of the Periodic Table of the Elements, preferably boron or aluminum, and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than 1 occurrence is Q a halide. Preferably, each Q is a fluorinated hydrocarbyl group having 1 to 20 carbon atoms, more preferably each Q is a fluorinated aryl group, and most preferably each Q is a pentafluoryl aryl group.

Examples of suitable $(NCA^{v-})$ also include diboron compounds as disclosed in U.S. Pat. No. 5,447,895, which is fully incorporated herein by reference. Another example of a suitable anion is a borate with three ortho-substituted fluoroaryl ligands and one alkyne ligand. Another example of a suitable anion is a borate containing fluoroaryl groups with polar substituents such as amines, ethers, silyl groups and derivatives thereof.

The term non-coordinating anion may be used interchangeably with the term weakly coordinating anion.

Additional suitable anions are known in the art and will be suitable for use with the catalysts of the invention. See in particular, U.S. Pat. No. 5,278,119, WO2002102857, WO2002051884, WO200218452, WO2000037513, WO2000029454, WO2000004058, WO9964476, WO2003049856, WO2003051892, WO2003040070, WO2003000740, WO2002036639, WO2002000738, WO2002000666, WO2001081435, WO2001042249, WO2000004059. Also see the review articles by S. H. Strauss, "The Search for Larger and More Weakly Coordinating Anions", *Chem. Rev.*, 93, 927-942 (1993) and C. A. Reed, "Carboranes: A New Class of Weakly Coordinating Anions for Strong Electrophiles, Oxidants and Superacids", *Acc. Chem. Res.*, 31, 133-139 (1998).

Illustrative, but not limiting examples of boron compounds which may be used as an activating cocatalyst in the preparation of the improved catalysts of this invention are tri-substituted ammonium salts such as: trimethylammonium tetraphenylborate, triethylammonium tetraphenylborate, tripropylammonium tetraphenylborate, tri(n-butyl)ammonium tetraphenylborate, tri(t-butyl)ammonium tetraphenylborate, N,N-dimethylanilinium tetraphenylborate, N,N-diethylanilinium tetraphenylborate, N,N-dimethyl-(2,4,6-trimethylanilinium) tetraphenylborate, trimethylammonium tetrakis(pentafluorophenyl)borate, triethylammonium tetrakis(pentafluorophenyl)borate, tripropylammonium tetrakis (pentafluorophenyl)borate, tri(n-butyl)ammonium tetrakis (pentafluorophenyl)borate, tri(sec-butyl)ammonium tetrakis (pentafluorophenyl)borate, N,N-dimethylanilinium tetrakis (pentafluorophenyl)borate, N,N-diethylanilinium tetrakis (pentafluorophenyl)borate, N,N-dimethyl-(2,4,6-trimethylanilinium) tetrakis(pentafluorophenyl)borate, trimethylammonium tetrakis(heptafluoronaphthyl)borate, triethylammonium tetrakis(heptafluoronaphthyl)borate, tripropylammonium tetrakis(heptafluoronaphthyl)borate, tri (n-butyl)ammonium tetrakis(heptafluoronaphthyl)borate, tri (sec-butyl)ammonium tetrakis(heptafluoronaphthyl)borate, N,N-dimethylanilinium tetrakis(heptafluoronaphthyl)borate, N,N-diethylanilinium tetrakis(heptafluoronaphthyl)borate, trimethylammonium (2-perfluorobiphenyl)$_3$(perfluorophenylalkynyl)borate, triethylammonium (2-perfluorobiphenyl)$_3$(perfluorophenylalkynyl)borate, tripropylammonium (2-perfluorobiphenyl)$_3$(perfluorophenylalkynyl)borate, tri(n-butyl)ammonium (2-perfluorobiphenyl)$_3$(perfluorophenylalkynyl)borate, tri(sec-butyl)ammonium (2-perfluorobiphenyl)$_3$(perfluorophenylalkynyl)borate, N,N-dimethylanilinium (2-perfluorobiphenyl)$_3$(perfluorophenylalkynyl)borate, N,N-diethylanilinium (2-perfluorobiphenyl)$_3$(perfluorophenylalkynyl)borate, trimethylammonium tetrakis-(2,3,4,6-tetrafluorophenylborate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluoro-phenyl)borate, dimethyl(t-butyl)ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluoro-phenyl)borate, and N,N-dimethyl-(2,4,6-trimethylanilinium)tetrakis-(2,3,4,6-tetrafluorophenyl)borate; dialkyl ammonium salts such as: di-(i-propyl)ammonium tetrakis(pentafluorophenyl)borate, and dicyclohexylammonium tetrakis(pentafluorophenyl)borate; and tri-substituted phosphonium salts such as: triphenylphosphonium tetrakis(pentafluorophenyl)borate, tri(o-tolyl)phosphonium tetrakis(pentafluorophenyl)borate, and tri(2,6-dimethylphenyl)phosphonium tetrakis(pentafluorophenyl)borate; non-Bronsted acids such as triphenylcarbenium tetrakis(pentafluorophenyl)borate, triphenylcarbenium tetrakis(heptafluoronaphthyl)borate, triphenylcarbenium (2-perfluorobiphenyl)$_3$(perfluorophenylalkynyl)borate, trisperfluorophenyl borane, and triperfluoronaphthyl borane.

Most preferably, the ionic stoichiometric activator is N,N-dimethylanilinium tetrakis(perfluorophenyl)borate and/or triphenylcarbenium tetrakis(perfluorophenyl)borate.

In one embodiment, activation methods using ionizing ionic compounds not containing an active proton but capable of producing an analogous metallocene catalyst cation and their non-coordinating anion are also contemplated and are described in EP-A-0 426 637, EP-A-0 573 403 and U.S. Pat. No. 5,387,568, which are all herein incorporated by reference.

The term "non-coordinating anion" (NCA) means an anion which either does not coordinate to said cation or which is only weakly coordinated to said cation thereby remaining sufficiently labile to be displaced by a neutral Lewis base. "Compatible" non-coordinating anions are those which are not degraded to neutrality when the initially formed complex decomposes. Non-coordinating anions useful in accordance with this invention are those that are compatible, stabilize the metal cation in the sense of balancing its ionic charge, yet retain sufficient lability to permit displacement by an ethylenically or acetylenically unsaturated monomer during polymerization. These types of cocatalysts sometimes use tri-isobutyl aluminum or tri-octyl aluminum as a scavenger.

Invention process also can employ cocatalyst compounds or activator compounds that are initially neutral Lewis acids but form a cationic metal complex and a noncoordinating anion, or a zwitterionic complex upon reaction with the invention compounds. For example, tris(pentafluorophenyl) boron or aluminum act to abstract a hydrocarbyl or hydride ligand to yield an invention cationic metal complex and stabilizing noncoordinating anion, see EP-A-0 427 697 and EP-A-0 520 732 for illustrations of analogous Group-4 metallocene compounds. Also, see the methods and compounds of EP-A-0 495 375. For formation of zwitterionic complexes using analogous Group 4 compounds, see U.S. Pat. Nos. 5,624,878; 5,486,632; and 5,527,929.

Additional neutral Lewis-acids are known in the art and are suitable for abstracting anionic ligands. See in particular the review article by E. Y.-X. Chen and T. J. Marks, "Cocatalysts for Metal-Catalyzed Olefin Polymerization: Activators, Activation Processes, and Structure-Activity Relationships", *Chem. Rev.*, 100, 1391-1434 (2000).

When X is a ligand, such as chloride, amido or alkoxy ligands, not capable of discrete ionizing abstraction with the ionizing, anion pre-cursor compounds, these functional group ligands can be converted via known alkylation reactions with organometallic compounds such as lithium or aluminum hydrides or alkyls, alkylalumoxanes, Grignard reagents, etc. See EP-A-0 500 944, EP-A1-0 570 982 and EP-A1-0 612 768 for analogous processes describing the reaction of alkyl aluminum compounds with analogous dihalide substituted metallocene compounds prior to or with the addition of activating noncoordinating anion precursor compounds.

When the cations of noncoordinating anion precursors are Bronsted acids such as protons or protonated Lewis bases (excluding water), or reducible Lewis acids such as ferrocenium or silver cations, or alkali or alkaline earth metal cations such as those of sodium, magnesium or lithium, the catalyst-precursor-to-activator molar ratio may be any ratio. Combinations of the described activator compounds may also be used for activation. For example, tris(perfluorophenyl)boron can be used with methylalumoxane.

Other useful ion forming Lewis acids include those having two or more Lewis acidic sites, such as those described in WO 99/06413 or Piers, et al. "New Bifunctional Perfluoroaryl Boranes: Synthesis and Reactivity of the ortho-Phenylene-Bridged Diboranes 1,2-(B($C_6F_5$)$_2$)$_2C_6X_4$(X=H, F)", J. Am. Chem. Soc., 1999, 121, 3244 3245, both of which are incorporated herein by reference. Other useful Lewis acids will be evident to those of skill in the art. Combinations of ion forming activators may be used.

Other activators include those described in PCT Publication No. WO 98/07515 such as tris(2,2',2"-nonafluorobiphenyl)fluoroaluminate, which publication is fully incorporated herein by reference. Combinations of activators are also contemplated by the invention, for example, alumoxanes and ionizing activators in combinations, see for example, PCT Publication Nos. WO 94/07928 and WO 95/14044, and U.S. Pat. Nos. 5,153,157 and 5,453,410, all of which are herein fully incorporated by reference. WO 98/09996 incorporated herein by reference describes activating precatalyst metal compounds with perchlorates, periodates and iodates including their hydrates. PCT Publication Nos. WO 98/30602 and WO 98/30603, which are incorporated by reference herein, describe the use of lithium (2,2'-bisphenyl-ditrimethylsilicate). 4THF as an activator for a precatalyst metal compound. Also, methods of activation such as using radiation (see EP-B1-0 615 981 herein incorporated by reference), electrochemical oxidation, and the like are also contemplated as activating methods for the purposes of rendering the neutral precatalyst metal compound or precursor to a cationic catalyst metal compound capable of polymerizing olefins.

In one non-limiting embodiment, one or more alumoxanes may be used to activate the low and high molecular weight catalyst components. In another non-limiting embodiment, one or more alumoxanes may be used to activate the low molecular weight precatalyst component while one or more ionizing activators are used to activate the high molecular weight precatalyst component. In another non-limiting embodiment, one or more alumoxanes may be used to activate the high molecular weight precatalyst component while one or more ionizing activators are used to activate the low molecular weight precatalyst component. In another embodiment one or more ionizing activator are used to activate the low and high molecular weight catalyst components. In another non-limiting example, one or more alumoxanes and one or more ionizing activators may be used to activate the low and high molecular weight precatalyst components.

In general the combined activator and metal compounds are combined in ratios of about 1000:1 to about 0.5:1.

When the activator is an alumoxane (modified or unmodified), any quantity of alumoxane that activates a precatalyst metal compound may be used. Preferably, the ratio of Aluminum to the total molar amount of precatalyst or catalyst metal is between 1000:1 and 1:1. More preferably, the ratio is from 500:1 to 25:1. Even more preferably, the ratio is from 250:1 to 50:1. Even more preferably, the ratio is between 200:1 and 75:1.

When the activator is an ionizing activator, any quantity of ionizing activator that activates a precatalyst metal compound may be used. Preferably, the ratio of ionizing activator to the total molar amount of precatalyst or catalyst metal is between 10:1 and 1:10. More preferably, the ratio is from 5:1 to 1:5. Even more preferably, the ratio is from 4:1 to 1:4. Even more preferably, the ratio is between 2:1 and 1:2.

When a combination of activators is employed, any quantity of activators that activates precatalyst metal compounds may be used.

Supports and Methods of Supporting

In a preferred embodiment, the catalysts of the invention comprise high and low molecular weight catalyst precursors, an activator and a support material. Methods for preparing supported catalysts are well known in the art and are easily extendible to the preparation of catalysts with high and low molecular weight catalyst metal compounds.

The above described precatalyst metal compounds and activators may be combined with one or more support materials or carriers using one of the support methods well known in the art or as described below. In the preferred embodiment, the method of the invention uses a polymerization catalyst in a supported form. For example, in a most preferred embodiment, a catalyst system is in a supported form, for example deposited on, bonded to, contacted with, or incorporated within, adsorbed or absorbed in, or on, a support or carrier.

The terms "support" or "carrier" are used interchangeably and are any support material, preferably a porous support material, for example, talc, inorganic oxides and inorganic chlorides. Other carriers include resinous support materials such as polystyrene, functionalized or crosslinked organic supports, such as polystyrene divinyl benzene polyolefins or polymeric compounds, zeolites, clays, or any other organic or inorganic support material and the like, or mixtures thereof.

The preferred carriers are inorganic oxides that include those Group 2, 3, 4, 5, 13 or 14 metal oxides. The preferred supports include silica, alumina, silica-alumina, magnesium chloride, and mixtures thereof. Other useful supports include magnesia, titania, zirconia, montmorillonite (EP-B1 0 511 665) and the like. Also, combinations of these support materials may be used, for example, silica-chromium, silica-alumina, silica-titania and the like.

It is preferred that the carrier, most preferably an inorganic oxide, has a surface area in the range of from about 10 to about 700 $m^2/g$, pore volume in the range of from about 0.1 to about 4.0 mL/g and average particle size in the range of from about 5 to about 500 μm. More preferably, the surface area of the carrier is in the range of from about 50 to about 500 $m^2/g$, pore volume of from about 0.5 to about 3.5 mL/g and average particle size of from about 10 to about 200 μm. Most preferably the surface area of the carrier is in the range is from about 100 to about 400 $m^2/g$, pore volume from about 0.8 to about 3.0 mL/g and average particle size is from about 5 to about 100 μm. The average pore size of the carrier of the invention typically has pore size in the range of from 10 to 1000 Å, preferably 50 to about 500 Å, and most preferably 75 to about 350 Å.

Examples of supporting catalyst systems are described in Hlalky, Chem. Rev. (2000), 100, 1347 1376 and Fink et al., Chem. Rev. (2000), 100, 1377 1390, U.S. Pat. Nos. 4,701,432, 4,808,561, 4,912,075, 4,925,821, 4,937,217, 5,008,228, 5,238,892, 5,240,894, 5,332,706, 5,346,925, 5,422,325, 5,466,649, 5,466,766, 5,468,702, 5,529,965, 5,554,704, 5,629,253, 5,639,835, 5,625,015, 5,643,847, 5,665,665, 5,698,487, 5,714,424, 5,723,400, 5,723,402, 5,731,261, 5,759,940, 5,767,032 and 5,770,664, U.S. Application Serial No. 271,598 filed Jul. 7, 1994 and Serial No. 788,736 filed Jan. 23, 1997, and PCT Publication Nos. WO 95/32995, WO 95/14044, WO 96/06187 and WO 97/02297, all of which are herein fully incorporated by reference.

In one embodiment, the catalyst compounds of the invention may be deposited on the same or separate supports together with an activator, or the activator may be used in an unsupported form, or may be deposited on a support different from the supported catalyst metal compounds of the invention, or any combination thereof.

In another embodiment, active catalysts may be prepared by supporting the ligands of the catalysts of the invention on support then treatment with a labile organometallic agent, such as $Zr(CH_2Ph)_4$, and an activator.

There are various other methods in the art for supporting a polymerization catalyst compound or catalyst system of the invention. For example, the catalyst compounds of the invention may contain a polymer bound ligand as described in U.S. Pat. Nos. 5,473,202 and 5,770,755, which are herein fully incorporated by reference; the system of the invention may be spray dried as described in U.S. Pat. No. 5,648,310, which is herein fully incorporated by reference; the support used with the catalyst system of the invention is functionalized as described in European Publication No. EP-A-0 802 203, which is herein fully incorporated by reference, or at least one substituent or leaving group is selected as described in U.S. Pat. No. 5,688,880, which is herein fully incorporated by reference.

In a preferred embodiment, the invention provides for a supported catalyst system that includes an antistatic agent or surface modifier that is used in the preparation of the supported catalyst system as described in PCT Publication No. WO 96/11960, which is herein fully incorporated by reference. The catalyst systems of the invention can be prepared in the presence of an olefin, for example hexene-1.

A preferred method for producing the supported catalyst system of the invention is described below and is described in U.S. application Ser. No. 265,533, filed Jun. 24, 1994 and Ser. No. 265,532, filed Jun. 24, 1994, and PCT Publication Nos. WO 96/00245 and WO 96/00243 both published Jan. 4, 1996, all of which are herein fully incorporated by reference. In this preferred method, precatalyst compounds are slurried in a liquid to form a solution and a separate solution is formed containing an activator and a liquid. The liquid may be any compatible solvent or other liquid capable of forming a solution or the like with the catalyst compounds and/or activator of the invention. In the most preferred embodiment the liquid is an aliphatic or aromatic hydrocarbon, most preferably toluene. The catalyst compound and activator solutions are mixed together and added to a porous support or the porous support is added to the solutions such that the total volume of the catalyst metal compound solution and the activator solution or the catalyst compound and activator solution is less than four times the pore volume of the porous support, more preferably less than three times, even more preferably less than two times; preferred ranges being from 1.1 times to 3.5 times range and most preferably in the 1.2 to 3 times range.

In another preferred embodiment, the catalyst system comprises a precatalyst as described herein activated by methylaluminoxane (MAO) and supported by silica. In a preferred embodiment, the MAO is first contacted with the silica and dried then treated with a solution of the high and low molecular weight precatalyst compounds then dried.

The precatalysts, activator and support may be combined in any order and under any process conditions (temperatures, pressures, concentrations) that produces a viable catalyst system. The combination may take place in the presence of a solvent. Preferred solvents are those that do not contain functional groups that would adversely effect the subsequent olefin polymerization. Non-limiting examples of preferred solvents include aliphatic and aromatic hydrocarbons such as pentane, hexane, heptane, octane, benzene and toluene.

In one non-limiting embodiment of the invention, a supported catalyst is prepared by combining high and low molecular weight precatalysts, solvent and activator then addition of a support material; afterwards, solvent may optionally be removed. In another non-limiting embodiment of the invention, a supported catalyst is prepared by combination of an activator with the support material, optionally in the presence of solvent, then a mixture or mixtures of high and low molecular weight precatalysts and solvent; afterwards, solvent may optionally be removed. In another non-limiting embodiment of the invention, a supported catalyst is prepared by combination of a low molecular weight precatalyst, an activator and support and optionally solvent followed by the addition of a high molecular weight precatalyst; afterwards, solvent may optionally be removed. In another non-limiting embodiment of the invention, a supported catalyst is prepared by combination of a high molecular weight precatalyst, an activator and support and optionally solvent followed by the addition of a low molecular weight precatalyst; afterwards, solvent may optionally be removed.

The catalyst systems of the disclosure may be produced by any one or more techniques known in the art useful for making catalyst compounds and any such methods suitable for use herein for example, but not limited to, the method disclosed in U.S. Pat. No. 6,608,153, incorporated herein by reference. Generally, for supported catalysts, a support is combined with a diluent to form a support slurry, which may be stirred and optionally heated during mixing. The first precatalyst compound, second precatalyst compound, and any one or more cocatalyst components may be added to the slurry in one or more steps and may be added individually or in any combination. The resulting slurry is mixed to achieve the desired contact between the components. Any one or more recovery technique may then be employed to recover the catalyst system. Examples of suitable recovery techniques include filtration, evaporation, vacuum distillation, simple decanting, and combinations thereof. The retrieved catalyst component may be washed any number of times with a suitable diluent, especially one or more aliphatic or cycloaliphatic hydrocarbons, or a mixture thereof. The resulting recovered catalyst composition may be dried using conventional techniques, such as passing an inert gas, especially nitrogen, over the solid to form a solid, granular powdery catalyst composition or it may be combined with an inert liquid, especially a hydrocarbon such as a mineral oil, for storage and use. The catalyst composition is preferably stored under an inert atmosphere.

The slurry comprising diluent and any one or more of the catalyst components and support particles may be heated during and/or after addition and/or mixing of each component. When the catalyst compounds are added to the slurry, either singly or in combination, the temperature of the slurry is generally sufficiently low so that the catalyst components are not inadvertently deactivated. Generally the temperature of the slurry is maintained at a temperature below 120° C. to avoid deactivation of the catalyst components.

In one embodiment of the invention, olefin(s), preferably $C_2$ to $C_{30}$ olefin(s) or alpha-olefin(s), preferably ethylene or propylene or combinations thereof are prepolymerized in the presence of the catalyst metal compound system of the invention prior to the main polymerization. The prepolymerization can be carried out batchwise or continuously in gas, solution or slurry phase including at elevated pressures. The prepolymerization can take place with any olefin monomer or combination and/or in the presence of any molecular weight controlling agent such as hydrogen. For examples of prepolymerization procedures, see U.S. Pat. Nos. 4,748,221, 4,789,359, 4,923,833, 4,921,825, 5,283,278 and 5,705,578, European Publication No. EP-B-0279 863, and PCT Publication No. WO 97/44371, all of which are herein fully incorporated by reference.

In one embodiment the polymerization catalyst is used in an unsupported form, preferably in a liquid form such as described in U.S. Pat. Nos. 5,317,036 and 5,693,727, and European Publication No. EP-A-0 593 083, all of which are herein incorporated by reference. The polymerization catalyst in liquid form can be fed to a reactor as described in PCT Publication No. WO 97/46599, which is fully incorporated herein by reference.

In one embodiment, the catalysts of the invention can be combined with a carboxylic acid salt of a metal ester, for example aluminum carboxylates such as aluminum mono, di- and tri-stearates, aluminum octoates, oleates and cyclohexylbutyrates, as described in U.S. Pat. No. 6,300,436.

Polymerization Processes

The catalyst systems and polymerization processes of the present disclosure are directed to polymerization of one or more olefin monomers having from 2 to 30 carbon atoms. The catalysts and polymerization processes are particularly well suited to the polymerization of two or more olefin monomers of ethylene, propylene, 1-butene, 1-pentene, 1-hexene, 1-heptene, 1-octene, 1-nonene, 4-methyl-1-pentene, 1-isobutene, 1-isobutene and 1-decene. Other monomers useful in the processes of the disclosure include ethylenically unsaturated monomers, diolefins having 4 to 18 carbon atoms, conjugated or nonconjugated dienes, polyenes, vinyl monomers and cyclic olefins. Non-limiting monomers useful in the disclosure may include norbornene, norbornadiene, isobutylene, isoprene, vinylbenzocyclobutane, styrenes, alkyl substituted styrene, ethylidene norbornene, dicyclopentadiene and cyclopentene.

The present disclosure encompasses homopolymerization processes comprising a single olefin species such as ethylene or propylene, as well as copolymerization reactions between one olefin species (referred to herein as the "monomer" and "monomer compound") and at least a second olefin species (referred to herein as "comonomer" and "comonomer compound") different from the first species. Generally a copolymer will comprise a major amount of the monomer compound (i.e., greater than about 50 mole percent) and a minor amount of the comonomer (i.e., less than about 50 mole percent). The comonomers generally have from three to about 20 carbon atoms in their molecular chain and examples include, but are not limited to, propylene, 1-butene, 2-butene, 3-methyl-1-butene, isobutylene, 1-pentene, 2-pentene, 3-methyl-1-pentene, 4-methyl-1-pentene, 1-hexene, 2-hexene, 3-hexene, 3-ethyl-1-hexene, 1-heptene, 2-heptene, 3-heptene, the four normal octenes, the four normal nonenes, or the five normal decenes. In one non-limiting embodiment, a copolymer may comprise ethylene copolymerized with a comonomer selected from 1-butene, 1-pentene, 1-hexene, 1-octene, 1-decene, or styrene.

In another embodiment of the process of the invention, ethylene or propylene is polymerized with at least two different comonomers, optionally one of which may be a diene, to form a terpolymer. In one embodiment, two of the three monomers of the terpolymer are butene and ethylene. In one embodiment, the comonomer content is 1.0 to 20.0 wt %, or 2.0 to 15.0 wt %, preferably about 1.0 to about 5.0 wt %, more preferably about 1.5 to about 3.0 wt %.

The polymerization processes of the present disclosure may be utilized for production of any polyolefin though preference is given to homopolymers and copolymers of polyethylene. In one non-limiting embodiment, the polyolefins are copolymers of ethylene and at least one comonomer selected from the group consisting of propylene, 1-butene, 1-pentene, 1-hexene, 1-heptene, 1-octene, and combinations thereof. In another non-limiting embodiment, the polyolefins are bimodal copolymers of ethylene and at least one comonomer selected from the group consisting of propylene, 1-butene, 1-pentene, 1-hexene, 1-heptene, 1-octene, and combinations thereof. In a preferred embodiment, the polymer comprises about 1.5 to about 3.0 wt % hexene.

Polymerization reactors suitable for the present disclosure may be any type of reactor known in the art and may comprise at least one raw material feed system, at least one feed system for catalyst or catalyst components, at least one reactor system, at least one polymer recovery system or any suitable combination thereof. Suitable reactors for the present disclosure may further comprise any one or more of any of a catalyst storage system, an extrusion system, a cooling system, a diluent recycling system, or a control system. Such reactors may comprise continuous take-off and direct recycling of catalyst, diluent, and polymer. Generally, continuous processes may comprise the continuous introduction of a monomer, a catalyst, and optionally a diluent into a polymerization reactor and the continuous removal from this reactor of polymer and recycling of diluent and unreacted monomers and comonomers.

The comonomer, if present in the polymerization reactor, is present at any level that will achieve the desired weight percent incorporation of the comonomer into the finished polyethylene. This is expressed as a mole ratio of comonomer to ethylene as described herein, which is the ratio of the gas concentration of comonomer moles in the cycle gas to the gas concentration of ethylene moles in the cycle gas. In one embodiment, the comonomer is present with ethylene in the cycle gas in a mole ratio range of from 0 or 0.0001 (comonomer:ethylene) to 0.20 or 0.10, and from 0.001 to 0.080 in another embodiment, and from 0.001 to 0.050 in even another embodiment, and from 0.002 to 0.20 in still another embodiment. In yet another embodiment, the comonomer is present with ethylene in the cycle gas in a mole ratio range comprising any combination of any upper limit with any lower limit as described herein.

The processes of the present disclosure may be characterized in that the desired composition of high molecular weight to low molecular weight moiety can be achieved at any of the above comonomer to ethylene ratios.

Hydrogen, if present in the polymerization reactor, is present at any level that will achieve the desired melt index (MI, or I2) and molecular weights of the high and the low molecular weight component. Using the catalyst systems of the present disclosure increasing the concentration of hydrogen may increase the melt index of the polyolefin generated. MI can thus be influenced by the hydrogen concentration. The amount of hydrogen in the polymerization can be expressed as a mole ratio relative to the total polymerizable monomer, for example, ethylene, or a blend of ethylene and another alpha olefin. The amount of hydrogen used in the polymerization processes of the present disclosure is an amount necessary to achieve the desired MI of the final polyolefin resin.

In one embodiment, the ratio of hydrogen to total ethylene monomer (mol ppm H2: mol % ethylene) in the circulating gas stream is in a range of from 0 to 100, in a range of from 0.05 to 50 in another embodiment, in a range of from 0.10 to 40 in even another embodiment, and in a range of from 0.15 to 35 in still another embodiment. In yet another embodiment, the ratio of hydrogen to total ethylene monomer (mol ppm H2: mol % ethylene) in the circulating gas stream may be in a range comprising any combination of any upper mole ratio limit with any lower mole ratio limit described above.

The processes of the disclosure may be characterized in that the desired composition of high molecular weight to low molecular weight moiety can be achieved at any of the above hydrogen to ethylene ratios.

The process may also include "condensing agents" as is known in the art and disclosed in, for example, U.S. Pat. Nos. 4,543,399, 5,405,922 and 462,999. The condensing agent, if present in the reactor can be at any level that will achieve the desired increase in the dew point in order to improve cooling and ultimately space time yields. Suitable condensing agents include but are not limited to saturated hydrocarbons such as propane, n-butane, isobutane, n-pentane, isopentane, neopentane, n-hexane, isohexane, n-heptane, n-octane or mixtures thereof.

The catalysts and catalyst systems of the invention described above are suitable for use in any polymerization process over a wide range of temperatures and pressures. The temperatures may be in the range of from −60° C. to about 280° C., preferably from 50° C. to about 200° C., and the pressures employed may be in the range from 1 atmosphere to about 500 atmospheres or higher.

The polymerization processes of the disclosure may be carried out in solution, in bulk, in suspension, in gas-phase, in slurry-phase, as a high-pressure process, or any combinations thereof. Generally solution, gas-phase and slurry-phase processes are preferred. The processes may be carried out in any one or more stages and/or in any one or more reactor having any one or more reaction zone and are conducted substantially in the absence of catalyst poisons. As known by one of skill in the art, organometallic compounds may be employed as scavenging agents for poisons to increase the catalyst activity. The polymerization processes may be carried out batchwise, continuously run, or any combinations thereof. In one non-limiting embodiment, the polymerization processes of the present disclosure are carried out in a continuous gas-phase reactor. In another non-limiting embodiment, polymerization processes of the disclosure are carried out in a single gas-phase reactor.

Preferred processes for the invention are high-pressure, solution, slurry and gas-phase processes.

A gas-phase process of the present disclosure may comprise contacting the catalyst system with monomers in a reactor vessel of desirable configuration to form a polyolefin. In one non-limiting embodiment, the contacting may take place in a first reactor vessel, followed by transfer of the formed polymer into another reactor vessel to allow further polymerization, optionally by adding the same or different monomers and optionally by adding the same or different catalyst components, activators, etc. In another non-limiting embodiment, the catalyst system is contacted with monomers in a single reactor vessel, followed by isolation of a finished polyolefin resin.

For example, a gas phase polymerization process of the disclosure may comprise use of a continuous cycle in which a cycling gas stream (i.e., a recycle stream or fluidizing medium) is heated in the reactor by the heat of polymerization. This heat may be removed from the recycle stream in another part of the cycle by a cooling system that is external to the reactor. In a gas fluidized bed process for producing polymers, a gaseous stream containing one or more monomers may be continuously cycled through a fluidized bed in the presence of a catalyst under reactive conditions. The gaseous stream is preferably withdrawn from the fluidized bed and then recycled back into the reactor. Polymer product may be withdrawn from the reactor and fresh monomer added to replace the polymerized monomer. (See for example U.S. Pat. Nos. 4,543,399, 4,588,790, 5,028,670, 5,317,036, 5,352, 749, 5,405,922, 5,436,304, 5,453,471, 5,462,999, 5,616,661, 5,627,242, 5,665,818, 5,677,375, and 5,668,228, incorporated herein by reference).

Other gas phase processes contemplated by the process of the invention include those described in U.S. Pat. Nos. 5,627, 242, 5,665,818 and 5,677,375, and European Publication Nos. EP-A-0 794 200, EP-A-0 802 202 and EP-B-634 421, all of which are herein fully incorporated by reference.

In a preferred embodiment, the gas-phase reactor utilized in the present invention is capable and the process of the invention is producing greater than 500 lbs of polymer per hour (227 Kg/hr) to about 200,000 lbs/hr (90,900 Kg/hr) or higher of polymer, preferably greater than 1000 lbs/hr (455 Kg/hr), more preferably greater than 10,000 lbs/hr (4540 Kg/hr), even more preferably greater than 25,000 lbs/hr (11, 300 Kg/hr), still more preferably greater than 35,000 lbs/hr (15,900 Kg/hr), still even more preferably greater than 50,000 lbs/hr (22,700 Kg/hr) and most preferably greater than 65,000 lbs/hr (29,000 Kg/hr) to greater than 100,000 lbs/hr (45,500 Kg/hr).

The reactor temperature in a gas phase process may vary from about 30° C. to about 120° C., preferably from about 60° C. to about 115° C., more preferably in the range of from about 70° C. to 110° C., and most preferably in the range of from about 70° C. to about 95° C.

The reactor pressure in a gas phase process of the disclosure may be in the range of from about 100 psig to about 500 psig (about 690 kPa to about 3448 kPa), preferably from about 200 psig to about 400 psig (about 1379 kPa to about 2759 kPa), and more preferably from about 250 psig to about 350 psig (about 1724 kPa to about 2414 kPa).

The catalyst system may be supplied to the polymerization system as a solid, a paste or in the form of a suspension in a hydrocarbon, and/or may be treated with inert components, such as paraffins, oils, or waxes, to achieve better metering. If the catalyst system is to be metered into the reactor together with the monomer to be polymerized or the monomer mixture to be polymerized, the mixing unit and the metering line are preferably cooled.

Any one or more additives such as an antistatic or an alcohol may be used in the polymerization processes of the present disclosure, for example to improve the particle morphology of the olefin polymer. In general it is possible to use any one or more of the numerous additives suitable in olefin polymerization processes to improve any one or more parameter such as but not limited to reactor operability, particle morphology, catalyst activity, catalyst performance, and polymerization efficiency. The one or more additives may be fed directly into the polymerization system, either together with or separately from the catalyst system.

Another preferred polymerization process is a slurry polymerization process. A slurry polymerization process generally uses pressures in the range of from about 1 to about 50 atmospheres and even greater and temperatures in the range of 0° C. to about 120° C. In a slurry polymerization, a suspension of solid, particulate polymer is formed in a liquid polymerization diluent medium to which ethylene and comonomers and often hydrogen along with catalyst are added. The suspension including diluent is intermittently or continuously removed from the reactor where the volatile components are separated from the polymer and recycled, optionally after a distillation, to the reactor. The liquid diluent employed in the polymerization medium is typically an alkane having from 3 to 7 carbon atoms, preferably a branched alkane. The medium employed should be liquid under the conditions of polymerization and relatively inert. When a propane medium is used the process must be operated above the reaction diluent critical temperature and pressure. Preferably, a hexane or an isobutane medium is employed.

A preferred polymerization technique of the invention is referred to as a particle form polymerization, or a slurry process where the temperature is kept below the temperature at which the polymer goes into solution. Such technique is well known in the art, and described in for instance U.S. Pat. No. 3,248,179, which is fully incorporated herein by reference. Other slurry processes include those employing a loop reactor and those utilizing a plurality of stirred reactors in series, parallel, or combinations thereof. Non-limiting examples of slurry processes include continuous loop or stirred tank processes. Also, other examples of slurry processes are described in U.S. Pat. No. 4,613,484, which is herein fully incorporated by reference.

In an embodiment the reactor used in the slurry process of the invention is capable of and the process of the invention is producing greater than 2000 lbs of polymer per hour (907 Kg/hr), more preferably greater than 5000 lbs/hr (2268 Kg/hr), and most preferably greater than 10,000 lbs/hr (4540 Kg/hr). In another embodiment the slurry reactor used in the process of the invention is producing greater than 15,000 lbs of polymer per hour (6804 Kg/hr), preferably greater than 25,000 lbs/hr (11,340 Kg/hr) to about 100,000 lbs/hr (45,500 Kg/hr).

Examples of solution processes are described in U.S. Pat. Nos. 4,271,060, 5,001,205, 5,236,998 and 5,589,555, which are fully incorporated herein by reference.

A preferred process of the invention is where the process, preferably a slurry or gas phase process is operated in the presence of a catalyst metal compound system of the invention and in the absence of or essentially free of any scavengers, such as triethylaluminum, trimethylaluminum, triisobutylaluminum and tri-n-hexylaluminum and diethyl aluminum chloride, dibutyl zinc and the like. This preferred process is described in PCT Publication No. WO 96/08520 and U.S. Pat. Nos. 5,712,352 and 5,763,543, which are herein fully incorporated by reference.

Preferred processes for the invention are high-pressure, solution, slurry and gas-phase processes. More preferred processes are slurry and gas-phase processes.

The polymers of the present disclosure are preferably produced in a single reactor utilizing the catalyst system disclosed herein. However, it is to be understood that polymers produced according to the instant invention may be further compounded to introduce various ancillary components to the polymer as is readily known to one of skill in the art.

The polymers of the disclosure may comprise a unimodal, bimodal or multimodal molecular weight distribution (MWD). A bimodal polymer/resin is defined herein as a polymer/resin comprising two peaks in it's molecular weight distribution, one of the two peaks having a higher average molecular weight (defined herein as the high molecular weight component) than the other component (defined as the low molecular weight component). A multimodal polymer/resin is defined as a polymer/resin comprising more than two peaks in the molecular weight distribution.

Generally, the polymers of the disclosure comprise a high molecular weight component and a low molecular weight component. The polymers of the disclosure generally comprise from about 0.01 to about 25% of the high molecular weight component, preferably from about 0.05 to about 20%, more preferably from about 0.075 to about 15% of a very high molecular weight component, even more preferably from about 0.1 to about 12.5% of a very high molecular weight component, wherein the fraction of the high molecular weight component is determined by integrating the area under the molecular weight vs. dwt %/d Log M curve from molecular weight=1,000,000 to molecular weight=10,000,000.

As described previously, "high molecular weight" is defined herein as being greater than about 1,000,000 g/mol, preferably greater than about 1,500,000 g/mol, more preferably greater than about 2,000,000 g/mol, and even more preferably greater than about 3,000,000 g/mol. In one non-limiting embodiment, high molecular weight is greater than 5,000,000 g/mol. As described previously, "low molecular weight" is defined herein as being in the range of from about 40,000 to about 200,000 g/mol, preferably from about 50,000 to about 180,000 g/mol, more preferably from about 60,000 to about 175,000 g/mol, and even more preferably from about 70,000 to about 150,000 g/mol. In one non-limiting embodiment, low molecular weight is about 100,000 g/mol.

Generally the high molecular weight component comprises a molecular weight at least 10 times greater than the low molecular weight component, preferably at least 20 times greater than that of the low molecular weight component, more preferably at least 30 times greater than that of the low molecular weight component, and even more preferably at least 40 times greater than that of the low molecular weight component.

Polymer Properties

The instant polymers are produced in a single reactor utilizing a catalyst comprising a first catalytic component which is a metallocene, and second catalytic component with is a phenoxide transition metal catalyst, preferably a biphenyl phenol catalyst (BPP) compound. All properties of the instant polymer may be expressed relative to a comparative polymer. As used herein, a comparative polymer comprises essentially the same components in essentially the same relative ratios as the inventive polymer. The comparative polymer is produced under essentially identical conditions including temperature, pressures, and residence time as the inventive polymer. The comparative polymer is also produced using the same metallocene catalyst as is used to produce the inventive polymer. The difference between the comparative polymer and the inventive polymer is that the comparative polymer is produced in the absence of the second catalytic component, such that the very high molecular weight material is not present in the polymer. This same holds true for various forms of the instant polymer.

Accordingly, the properties of a film of the instant polymer are determined relative to a comparative film produced in essentially the same way from a comparative resin, the comparative resin produced in essentially the same way using essentially the same components except that the comparative resin is produced in the absence of the second catalyst compound.

It has been found that a film of the polymer of the instant disclosure represents an improvement over the prior art, as determined relative to a film of a comparative polymer produced without the second catalyst component. Generally the inventive polymers of the disclosure may have a density in the range of from about 0.86 g/cm$^3$ to about 0.93 g/cm$^3$ as measured according to ASTM 1505-03, preferably about 0.90 g/cm$^3$ to about 0.925 g/cm$^3$, with about 0.91 g/cm$^3$ to about 0.921 g/cm$^3$ being more preferred.

Films of the inventive polymers (also referred to herein as films of the inventive resins) of the instant disclosure generally exhibit excellent Elmendorf Tear strength (Elmendorf Tear (g/mil): ASTM D-1922) as well as a balance of MD and TD tear strength, an improvement of melt strength, dart drop impact strength 9 Dart Drop Impact F50 (g/mil): ASTM D-1709 A), and optical properties including a reduction in haze, an improvement in clarity, and an improvement in gloss relative to a comparative film.

As used herein, "melt strength" is defined as the force required to draw a molten polymer extrudate at a rate of 12 mm/s$^2$ and at an extrusion temperature (190° C. and 250° C. were used herein) until breakage of the extrudate whereby the force is applied by take up rollers. The polymer is extruded at a velocity of 0.33 mm/s through an annular die of 2 mm diameter and 30 mm length. Melt strength values reported herein are determined using a Gottfert Rheotens tester and are reported in centi-Newtons (cN). Additional experimental parameters for determining the melt strength are listed in Table 9. For the measurements of melt strength, the resins were stabilized with 500 ppm of Irganox 1076 and 1500 ppm of Irgafos 168.

Melt strength is the property of the polymer which indicates its ability to withstand drawing without breaking. Melt strength is typically improved by the presence of high molecular weight tail or long chain branches. However, the inventive polymers do not possess long chain branching or a g' below 0.85, and yet have improved melt strength over a comparative polymer.

In one non-limiting embodiment, the polymers of the present disclosure may have a melt index ("MI" or "$I_2$") as measured by ASTM-D-1238-E (190° C., 2.16 kg weight) in the range of from about 0.001 dg/min to 25 dg/min. In other non-limiting embodiments, the polymers of the present disclosure may have a MI in a range of from about 0.001 dg/min to about 5 dg/min; in even other non-limiting embodiments a MI in a range of from about 0.01 dg/min to about 5 dg/min in other embodiments; and in still other non-limiting embodiments a MI in a range of from about 0.01 dg/min to about 1 dg/min.

In one non-limiting embodiment, the polymers of the present disclosure may have a melt flow ratio (MFR) in the range of from about 10 to 300. MFR is defined as $I_{21}/I_2$, wherein $I_{21}$ is measured by ASTM-D-1238-F, at 190° C., 21.6 kg weight. In other non-limiting embodiments, the polymers of the present disclosure may have a MFR in a range of from about 15 to 250; in even other non-limiting embodiments, a MFR in a range of from about 15 to 200; and in still other non-limiting embodiments a MFR in a range of from about 20 to 150.

As known by one of skill in the art, when subjected to uniaxial extension at a given strain rate, the extensional viscosity of a polymer increases with time. As also known by one of skill in the art, the transient uniaxial extensional viscosity of a linear polymer can be predicted. Strain hardening occurs when a polymer is subjected to uniaxial extension and the transient extensional viscosity increases more than what is predicted from linear viscoelastic theory. As defined herein, the strain hardening index is the ratio of the observed transient uniaxial extensional viscosity to the theoretically predicted transient uniaxial extensional viscosity. Strain hardening index is expressed herein as the following ratio:

$\eta_E^+$observed/$\eta_E^+$predicted.

At conditions characteristic of film blowing, for example strain rate of 1 sec$^{-1}$, temperature of 190° C., and time of 4 seconds (i.e., a strain ($\epsilon$) of 4), generally the strain hardening index of the polymers of the present disclosure is a ratio/value greater than 3 in some embodiments, a value greater than 5 in other embodiments, a value greater than 8 in even other embodiments, and a value greater than 10 in still other embodiments.

The resins of the disclosure are suitable for use in a variety of products and end-use applications including, but not limited to film, sheets, laminating, jacketing, insulating, and a variety of articles produced by injection molding, blow molding, extrusion coating, profile extrusion, and combinations thereof.

Films of the instant disclosure may have a haze determined according to ASTM D2103-08, of less than or equal to about 35%, more preferably less than or equal to about 30%, more preferably less than or equal to about 30%, more preferably less than or equal to about 25%, more preferably less than or equal to about 20%, more preferably less than or equal to about 15%, more preferably less than or equal to about 10%, more preferably less than or equal to about 9%, more preferably less than or equal to about 8%, more preferably less than or equal to about 7%, more preferably less than or equal to about 6%, more preferably less than or equal to about 5%, more preferably less than or equal to about 4%, more preferably less than or equal to about 3%, more preferably less than or equal to about 2%, more preferably less than or equal to about 1%, according to ASTM D2103-08, or an equivalent thereof.

Films of the instant disclosure may have a haze with is at least 100% less than a comparative film produced in the absence of the high molecular weight catalyst, more preferably at least 200% less, with at least 300% less haze with respect to a comparative film being preferred.

Films of the instant disclosure may have a dart drop impact strength determined according to ASTM D-1709 A of greater than or equal to about 250 g/mil, preferably greater than or equal to about 300, more preferably greater than or equal to about 350, more preferably greater than or equal to about 400, more preferably greater than or equal to about 350, more preferably greater than or equal to about 400, more preferably greater than or equal to about 450, more preferably greater than or equal to about 500, more preferably greater than or equal to about 550, more preferably greater than or equal to about 600, more preferably greater than or equal to about 650, more preferably greater than or equal to about 700, more preferably greater than or equal to about 750, more preferably greater than or equal to about 800, more preferably greater than or equal to about 850, more preferably greater than or equal to about 900, more preferably greater than or equal to about 950, more preferably greater than or equal to about 1000, more preferably greater than or equal to about 1100, more preferably greater than or equal to about 1200, more preferably greater than or equal to about 1300, more preferably greater than or equal to about 1369 g/mil.

Films of the instant disclosure may have a dart drop impact strength determined according to ASTM D-1709 A which is at least 10% greater than a comparative film produced in the absence of the high molecular weight catalyst, more preferably at least 20% greater, with at least 30% greater being more preferred, with at least 40% greater being still more preferred, with at least 50% being still more preferred.

Films of the instant disclosure may have a gloss as determined according to ASTM D2457-08 of greater than or equal to about 30%, more preferably greater than or equal to about 35%, more preferably greater than or equal to about 40%, more preferably greater than or equal to about 45%, more preferably greater than or equal to about 50%, more preferably greater than or equal to about 55%, more preferably greater than or equal to about 60%, more preferably greater than or equal to about 65%, more preferably greater than or equal to about 70%, more preferably greater than or equal to about 75%, more preferably greater than or equal to about 80%, more preferably greater than or equal to about 85%, more preferably greater than or equal to about 90%.

Films of the instant disclosure may have a gloss as determined according to ASTM D2457-08 which is at least 10% greater than a comparative film produced in the absence of the high molecular weight catalyst, more preferably at least 20% greater, with at least 30% greater being more preferred, with at least 40% greater being still more preferred, with at least 50% being still more preferred.

Films of the instant disclosure may have an Elmendorf Tear in the machine direction (MD) as determined by ASTM D1922 of greater than or equal to about 40 g/mil, preferably greater than or equal to about 50 g/mil, preferably greater than or equal to about 60 g/mil, preferably greater than or equal to about 70 g/mil, preferably greater than or equal to about 80 g/mil, preferably greater than or equal to about 90 g/mil, preferably greater than or equal to about 100 g/mil, preferably greater than or equal to about 150 g/mil, preferably greater than or equal to about 200 g/mil, preferably greater than or equal to about 250 g/mil, preferably greater than or equal to about 300 g/mil, preferably greater than or equal to about 350 g/mil, preferably greater than or equal to about 400 g/mil, preferably greater than or equal to about 450 g/mil, preferably greater than or equal to about 500 g/mil, preferably greater than or equal to about 600 g/mil, preferably greater than or equal to about 700 g/mil.

Films of the instant disclosure may have an Elmendorf Tear in the machine direction (MD) as determined by ASTM D1922 which is at least 10% greater than a comparative film produced in the absence of the high molecular weight catalyst, more preferably at least 20% greater, with at least 30% greater being more preferred, with at least 40% greater being still more preferred, with at least 50% being still more preferred.

Films of the instant disclosure may have an Elmendorf Tear in the transverse direction (TD) as determined by ASTM D1922 of greater than or equal to about 40 g/mil, preferably greater than or equal to about 50 g/mil, preferably greater than or equal to about 60 g/mil, preferably greater than or equal to about 70 g/mil, preferably greater than or equal to about 80 g/mil, preferably greater than or equal to about 90 g/mil, preferably greater than or equal to about 100 g/mil, preferably greater than or equal to about 150 g/mil, preferably greater than or equal to about 200 g/mil, preferably greater than or equal to about 250 g/mil, preferably greater than or equal to about 300 g/mil, preferably greater than or equal to about 350 g/mil, preferably greater than or equal to about 400 g/mil, preferably greater than or equal to about 450 g/mil, preferably greater than or equal to about 500 g/mil, preferably greater than or equal to about 600 g/mil, preferably greater than or equal to about 700 g/mil.

Films of the instant disclosure may have an Elmendorf Tear in the transverse direction (TD) as determined by ASTM D1922 which is at least 10% greater than a comparative film produced in the absence of the high molecular weight catalyst, more preferably at least 20% greater, with at least 30% greater being more preferred, with at least 40% greater being still more preferred, with at least 50% being still more preferred.

Films of the instant disclosure may have an Elmendorf Tear Ratio, MD/TD of greater than or equal to about 10%, preferably greater than or equal to about 15%, preferably greater than or equal to about 20%, preferably greater than or equal to about 25%, preferably greater than or equal to about 30%, preferably greater than or equal to about 35%, preferably greater than or equal to about 40%, preferably greater than or equal to about 45%, preferably greater than or equal to about 50%, preferably greater than or equal to about 55%, preferably greater than or equal to about 60%, preferably greater than or equal to about 65%, preferably greater than or equal to about 70%, preferably greater than or equal to about 75%, preferably greater than or equal to about 80%, preferably greater than or equal to about 85%, preferably greater than or equal to about 90%, preferably greater than or equal to about 92%, preferably greater than or equal to about 96%.

Films of the instant disclosure may have any combination of an improved a haze determined according to ASTM D2103-08, an improved dart drop impact strength determined according to ASTM D-1709 A, an improved gloss as determined according to ASTM D2457-08, an improved Elmendorf Tear in the machine direction (MD) as determined by ASTM D1922, an improved Elmendorf Tear in the transverse direction (TD) as determined by ASTM D1922, an improved an Elmendorf Tear Ratio, MD/TD or the like, relative to a comparative polymer which does not include the high molecular weight component of the instant invention.

EXAMPLES

It is to be understood that while the invention has been described in conjunction with the specific embodiments thereof, the foregoing description is intended to illustrate and not limit the scope of the invention. Other aspects, advantages and modifications will be apparent to those skilled in the art to which the invention pertains.

Therefore, the following examples are put forth so as to provide those skilled in the art with a complete disclosure and description of how to make and use the compounds of the invention, and are not intended to limit the scope of that which the inventors regard as their invention. Because of the high molecular weights of the polyethylene resins described herein, it is necessary to measure size exclusion chromatography at elevated temperatures to ensure adequate solubility of the polymer molecules. Molecular weights and molecular weight distributions of the resins described herein were determined using high temperature size exclusion chromatography.

The following ASTM methods were utilized herein:
Melt Index (MI) (g/10 min): ASTM D-1238, condition 190° C.;
Density (g/cc): ASTM-D-4703-03 and ASTM-D-1505;
Dart Drop Impact F50 (g/mil): ASTM D-1709 A;
Elmendorf Tear (g/mil): ASTM D-1922;
Secant Modulus (1%) (psi): ASTM D-882;
Tensile @ Yield (psi): ASTM D-882;
Ultimate Tensile (psi): ASTM D-882; and
Ultimate Elongation (%): ASTM D-882.

Measurements of Molecular Weights and Molecular Weight Distributions

The molecular weights and molecular weight distributions of the resins described in the present disclosure were characterized using a High Temperature Size Exclusion Chromatograph (PL 220, Polymer Laboratories), equipped with a differential refractive index detector (DRI). Three Polymer Laboratories PLgel 10 mm Mixed-B columns were used. The nominal flow rate was 1.0 cm$^3$/min, and the nominal injection volume was 300 μL. The various transfer lines, columns and differential refractometer (the DRI detector) were contained in an oven maintained at 160 C.

Polymer solutions were prepared in filtered 1,2,4-Trichlorobenzene (TCB) containing 1000 ppm of butylated hydroxy toluene (BHT). The same solvent was used as the SEC eluent. Polymer solutions were prepared by dissolving the desired amount of dry polymer in the appropriate volume of SEC eluent to yield concentrations ranging from 0.5 to 1.5 mg/mL. The sample mixtures were heated at 160° C. with continuous agitation for about 2 to 2.5 hours. Sample solution will be filtered off-line before injecting to GPC with 2 μm filter using the Polymer Labs SP260 Sample Prep Station.

The separation efficiency of the column set was calibrated using a series of narrow MWD polystyrene standards, which reflects the expected MW range for samples and the exclusion limits of the column set. Eighteen individual polystyrene standards, ranging from Mp ~580 to 10,000,000, were used to generate the calibration curve. The polystyrene standards are obtained from Polymer Laboratories (Amherst, Mass.). To assure internal consistency, the flow rate is corrected for each calibrant run to give a common peak position for the flow rate marker (taken to be the positive inject peak) before determining the retention volume for each polystyrene standard. The flow marker peak position thus assigned was also used to correct the flow rate when analyzing samples; therefore, it is an essential part of the calibration procedure. A calibration curve (log Mp vs. retention volume) is generated by recording the retention volume at the peak in the DRI signal for each PS standard, and fitting this data set to a 2$^{nd}$-order polynomial. The equivalent polyethylene molecular weights are determined by using the following Mark-Houwink coefficients:

|    | k (dL/g)           | A     |
| -- | ------------------ | ----- |
| PS | $1.75 \times 10^{-4}$ | 0.67  |
| PE | $5.79 \times 10^{-4}$ | 0.695 |

Dynamic Rheology

For dynamic oscillatory shear measurements, the resins were stabilized with 500 ppm of Irganox 1076 and 1500 ppm of Irgafos 168. The measurements were carried out on an oscillatory rheometer (Rheometrics RDS-2, ARES) with 25 mm diameter parallel plates in a dynamic mode under nitrogen atmosphere. For all experiments, the rheometer was thermally stable at 190° C. for at least 30 minutes before inserting compression-molded sample of resin onto the parallel plates. To determine the samples viscoelastic behavior, frequency sweeps in the range from 0.01 to 100 rad/s were carried out at 190° C. under constant strain. To determine the activation energy, the sweeps were carried out at 5 different temperatures as described herein.

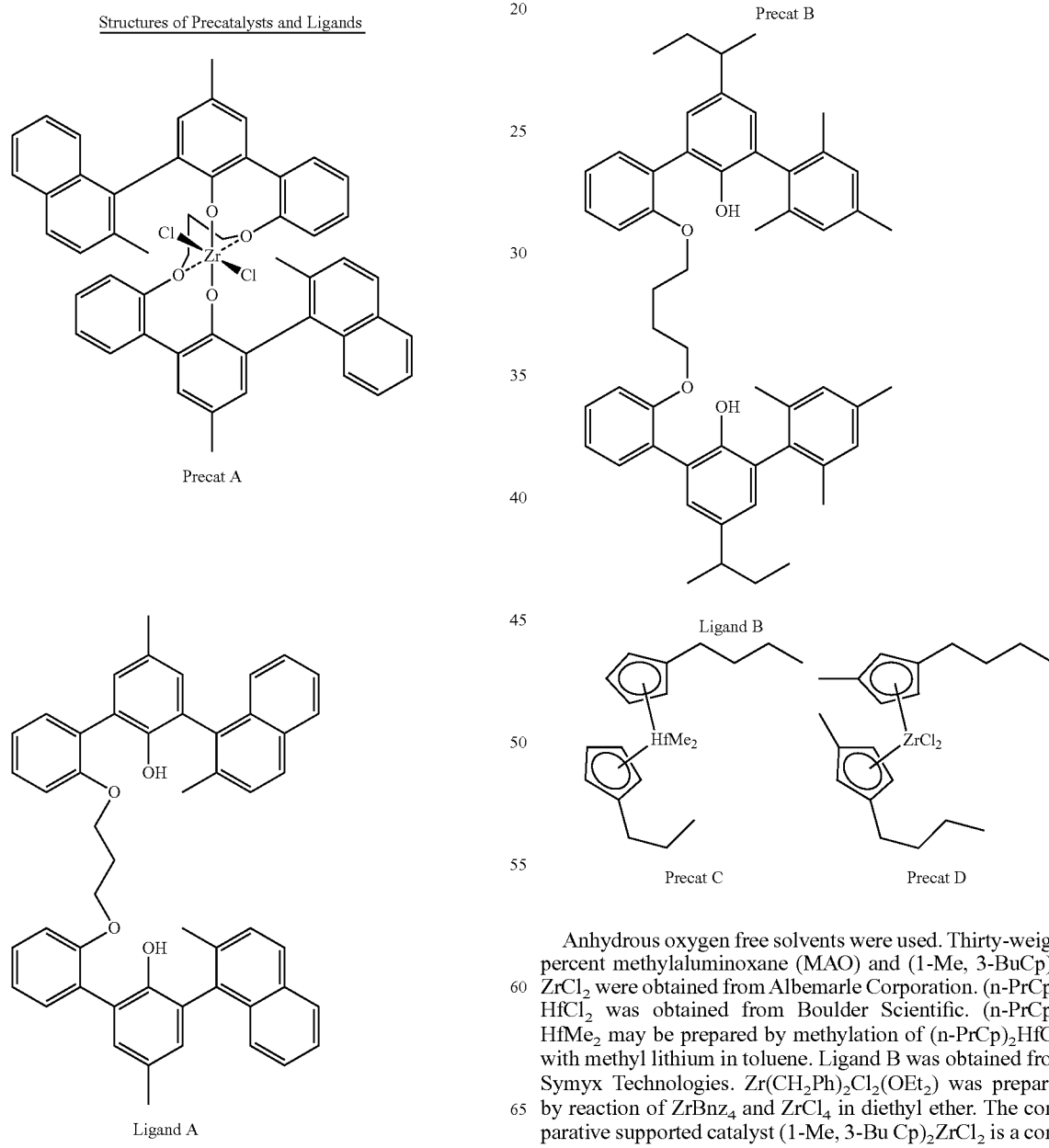

Anhydrous oxygen free solvents were used. Thirty-weight percent methylaluminoxane (MAO) and (1-Me, 3-BuCp)$_2$ ZrCl$_2$ were obtained from Albemarle Corporation. (n-PrCp)$_2$HfCl$_2$ was obtained from Boulder Scientific. (n-PrCp)$_2$HfMe$_2$ may be prepared by methylation of (n-PrCp)$_2$HfCl$_2$ with methyl lithium in toluene. Ligand B was obtained from Symyx Technologies. Zr(CH$_2$Ph)$_2$Cl$_2$(OEt$_2$) was prepared by reaction of ZrBnz$_4$ and ZrCl$_4$ in diethyl ether. The comparative supported catalyst (1-Me, 3-Bu Cp)$_2$ZrCl$_2$ is a commercial catalyst (HP100) obtained from Univation Technologies. The preparation of Ligand A is disclosed in the parent application of the instant disclosure.

Preparation of Precatalyst A

To a solution consisting of Ligand A (2.750 grams, 3.814 mmol) in approximately 80 milliliters of toluene was added a solution of $Zr(CH_2Ph)_2Cl_2(Et_2O)$ (1.603 grams) in 20 milliliters of toluene. An additional 20 milliliters of solvent were added to the mixture. After stirring the mixture at room temperature for 1 hour, the reaction was heated to 80° C. for 2 hours. Approximately 70% of the solvent was removed, and pentane added to induce further precipitation of the product. The mixture was chilled. The solids collected by filtration and washed with minimum pentane.

Preparation of Methyl Aluminoxane Supported on Silica (SMAO)

In a typical procedure, Crosfield ES757 silica (741 g), dehydrated at 600° C., was added to a stirred (overhead mechanical conical stirrer) mixture of toluene (2 L) and 30 wt % solution of methyl aluminoxane in toluene (874 g, 4.52 mol). The silica was chased with toluene (200 mL) then the mixture was heated to 90° C. for 3 h. Afterwards, volatiles were removed by application of vacuum and mild heat (40° C.) overnight then the solid was allowed to cool to room temperature.

Supported Catalyst Preparations

A solution of precatalysts (PC) and toluene was added at a rate of ca. 3 mL/min to a slurry SMAO and pentane (amounts provided in Table below), stirred with an overhead stirrer. After stirring for ≧1 h, the mixture was filtered and dried in-vacuo.

TABLE

Supported Catalyst preparations

| Example # | Catalyst Batch | PC 1 | Mass of PC 1 (mg) | PC 2 | Mass of PC 2 (g) | SMAO (g) | Toluene (mL) | Pentane (mL) | mol % PC 1 |
|---|---|---|---|---|---|---|---|---|---|
| | 307-39 | A | 108 | D | 6.494 | 402.9 | 300 | 2000 | 0.81 |
| | 307-40 | A | 53 | D | 6.622 | 408 | 300 | 2000 | 0.4 |
| | 307-42 | A | 160 | D | 6.569 | 40.01 | 500 | 2000 | 1.2 |

Polymerization Testing in a Continuous Fluidized Bed Reactor

The test catalysts were evaluated in a continuous run gas phase reactor R124 (LGPR). The reactor was lined out with standard HP100 catalyst at conditions used to make 1.2 MI, 0.917 density (LGPR condition 51-2006). Product was collected and the reactor was transitioned to each of the other catalysts.

Ethylene/1-hexene copolymers were produced according to the following procedure. The catalyst composition was injected dry into a fluidized bed gas phase polymerization reactor. More particularly, polymerization was conducted in a 152.4 mm diameter gas-phase fluidized bed reactor operating at approximately 2068 kPa total pressure. The reactor bed weight was approximately 2 kg. Fluidizing gas was passed through the bed at a velocity of approximately 0.6 m per second. The fluidizing gas exiting the bed entered a resin disengaging zone located at the upper portion of the reactor. The fluidizing gas then entered a recycle loop and passed through a cycle gas compressor and water-cooled heat exchanger. The shell side water temperature was adjusted to maintain the reactor temperature as specified in Tables 4-8. Ethylene, hydrogen, 1-hexene and nitrogen were fed to the cycle gas loop just upstream of the compressor at quantities sufficient to maintain the desired gas concentrations as specified in Tables 4-8. Gas concentrations were measured by an on-line vapor fraction analyzer. Product (polyethylene particles) was continuously withdrawn from the reactor in batch mode into a purging vessel before it was transferred into a product bin. Residual catalyst and activator in the resin was deactivated in the product drum with a wet nitrogen purge. The catalyst was fed to the reactor bed through a stainless steel injection tube at a rate sufficient to maintain the desired polymer production rate. "$C_6/C_2$ flow ratio ("FR")" is the ratio of the lbs of 1-hexene comonomer feed to the pounds of ethylene feed to the reactor, whereas the $C_6/C_2$ ratio is the ratio of the gas concentration of 1-hexene moles in the cycle gas to the gas concentration of ethylene moles in the cycle gas. The $C_6/C_2$ ratio is obtained from a cycle gas vapor fraction analyzer, whereas the $C_6/C_2$ Flow Ratio comes from some measure of the mass flow. The cycle gas is the gas in the reactor, and is measured from a tap off the recirculating loop around the reactor. The ratios reported in the following tables are from the gas concentrations in the reactor. Samples are taken every 9 min, and thus reported $C_6/C_2$ ratios are running averages. Tables 4-8 provide summaries of run conditions and product properties of non-limiting examples of the present disclosure for resins with densities of 0.91-0.95 as indicated in the tables.

The MI and HLMI values reported in Tables 3 as "QC, reactor granules" were obtained from the polymer granules that were isolated from the polymerization reactor. Each granular resin was dry-blended with 1500 ppm BHT (2,6-bis(1,1-dimethylethyl)-4-methylphenol). MI and HLMI were then measured according to ASTM-D-1238-E and ASTM D-1238-F, respectively.

The MI and HLMI values reported in Table 3 as "ASTM, pellets" were obtained from compounded resins. To compound the resins, 500 ppm Irganox 1076 and 1500 ppm Igrafos 168 (both available from Ciba Chemicals) were added to the reactor granules and the admixture extruded using a ¾" Haake twin screw extruder. The melt temperature was 210° C. The output rate was about 3.5 lbs/hr. The MI and HLMI of the pellets were then measured according to ASTM-D-1238-E and ASTM D-1238-F, respectively.

The density values reported in Table 3 as "QC, reactor granules" were obtained from the polymer granules that were isolated from the polymerization reactor. Each granular resin was dry-blended with 1500 ppm BHT and compression molded plaques were produced by heating the polymers in a mold to 179° C. and subsequently cooling them to 23° C. at a rate of 15° C. The molding pressure was chosen such that air pockets are removed and a uniform samples result. The density was then determined by immersing solid specimens of the compression molded plaques in a column filled with liquid of uniformly gradient density. The gradient density was in accordance with ASTM 1505.

The density values reported in Tables 3 as "ASTM, pellets" were obtained from compounded resins. To compound the resins, 500 ppm Irganox 1076 and 1500 ppm Igrafos 168 were added to the reactor granules and the admixture extruded using a ¾" Haake twin screw extruder. The melt temperature was 210° C. The output rate was about 3.5 lbs/hr. The density of the pellets was then measured according to ASTM 1505-03.

These catalysts were tested in a continuous fluidized-bed gas-phase reactor with a nominal 14" reactor diameter, an average bed weight of about 1900 g, gas-velocity of about 1.6 ft/s, production rate of about 500 g/h. The reactor was operated at a temperature of 79.4° C., and a pressure of 300 psig. The composition of ethylene, hydrogen, and 1-hexene is indicated in Table 3 below; the balance being nitrogen.

TABLE 3

Summary of Polymerization conditions

| Description | Comparative Catalyst | HP-100 + 0.4% UNIV08 | HP-100 + 0.8% UNIV08 | HP-100 + 1.2% UNIV08 |
|---|---|---|---|---|
| Catalyst Type | HP-100 Std | ECI2 + 0.4% UHMW cat | ECI2 + 0.8% UHMW cat | ECI2 + 1.2% UHMW cat |
| Catalyst Batch | B-1518 | 307-40 | 307-39 | 307-42 |
| External Continuity Type | None | None | None | None |
| Cat Density gm/cc | 0.36 | 0.36 | 0.36 | 0.36 |
| Total Product Produced | 5498 | 3463 | 1908 | 3440 |
| Bed Turnovers (whole part) | 8.5 | 5.0 | 2.8 | 5.0 |
| Residence Time | 4.54 | 4.67 | 4.55 | 4.79 |
| C2 Concentration (mole %) | 70.0 | 70.0 | 70.0 | 70.1 |
| C2 Partial Pressure (psia) | 219.7 | 219.4 | 219.5 | 219.7 |
| H2 Concentration (ppm) | 169.8 | 169.9 | 169.8 | 170.0 |
| H2/C2 Analyzer Ratio (ppm/mole %) | 2.43 | 2.43 | 2.43 | 2.43 |
| Hexene conc (mole %) | 1.26 | 1.60 | 1.62 | 1.67 |
| C6/C2 Analyzer Ratio | 0.02 | 0.02 | 0.02 | 0.02 |
| C2 Feed (lb/hr) | 168.7 | 169.8 | 182.1 | 170.5 |
| H2/C2 Flow Ratio (Mlb/lb) | 0.0271 | 0.0247 | 0.0298 | 0.0267 |
| C6/C2 Flow Ratio | 0.072 | 0.072 | 0.072 | 0.072 |
| IC5 (mole %) | 0.00 | 0.01 | −0.01 | 0.00 |
| N2 Conc (mole %) | 28.72 | 28.38 | 28.41 | 28.25 |
| Reactor Vent Rate (lb/hr) | 7.6 | 7.9 | 8.0 | 8.4 |
| Reactor Pressure (psia) | 313.8 | 313.5 | 313.8 | 313.7 |
| Bed Temperature (deg F.) | 185.34 | 185.82 | 185.64 | 186.29 |
| Exchanger dp (psi) | 0.38 | 0.37 | 0.38 | 0.38 |
| Plate dp ("H2O) | 75 | 100 | 142 | 106 |
| Gas Velocity (ft/sec) | 2.25 | 2.25 | 2.25 | 2.25 |
| Bed Weight (lbs) | 644 | 686 | 678 | 685 |
| Bed Level (ft) | 13.8 | 13.8 | 12.9 | 13.5 |
| Fluidized Bed Density (lb/ft3) | 17.0 | 18.0 | 19.1 | 18.5 |
| Exp sect diff press (inch H20) | 6.7 | 6.0 | 3.8 | 5.3 |
| Cat feed rate (g/hr) | 10.99 | 6.85 | 9.16 | 10.36 |
| Cat feed rate (sec) | 15 | 23 | 24 | 23 |
| Number of Cat Cylinders | 1 | 1 | 1 | 1 |
| Cat Feeder Efficiency (%) | 0.90 | 0.86 | 1.20 | 1.30 |
| IC5 Flush with Continuity Additive lb/hr | 0.00 | 0.00 | 0.00 | 0.00 |
| N2 flow to annulus with cat lb/hr | 3.62 | 3.49 | 3.60 | 3.49 |
| N2 flow with Cat lb/hr | 2.98 | 2.98 | 2.91 | 2.96 |
| Production Rate (lb/hr) Drops | 142 | 147 | 149 | 143 |
| Cat Activity matl balance (gm/gm) Drops | 5864 | 9741 | 7383 | 6268 |
| Cat Activity ICPES Zr | | | | |
| Cat Activity ICPES Al | | | | |
| Zr (ppm) in Poly | | | | |
| Al (ppm) in Poly | | | | |
| Melt Index (I2) | 0.95 | 0.62 | 0.59 | 0.42 |
| HLMI (I21) | 16.27 | 10.92 | | 8.83 |
| MFR (I21/I2) | 17.13 | 17.61 | | 21.02 |
| Density (gm/cc) | 0.9209 | 0.9201 | 0.9201 | 0.9206 |
| Bulk Density (gm/cc) | 0.4000 | 0.4268 | | 0.4338 |
| PFT | 8.43 | 6.94 | | 6.84 |

The present inventors have found that the polymers produced by a catalyst system of the disclosure comprising a metallocene catalyst component and a non-metallocene catalyst component possess advantageous properties in comparison to polymer produced using the metallocene catalyst alone, and in comparison to conventional polymers.

As used herein, "melt strength" is defined as the force required to draw a molten polymer extrudate at a rate of 12 mm/s$^2$ and at an extrusion temperature (190° C. and 250° C. were used herein) until breakage of the extrudate whereby the force is applied by take up rollers. The polymer is extruded at a velocity of 0.33 mm/s through an annular die of 2 mm diameter and 30 mm length. Melt strength values reported herein are determined using a Gottfert Rheotens tester and are reported in centi-Newtons (cN). Additional experimental parameters for determining the melt strength are listed in Table 9. For the measurements of melt strength, the resins were stabilized with 500 ppm of Irganox 1076 and 1500 ppm of Irgafos 168.

TABLE 9

| Melt Strength test parameters | |
| --- | --- |
| Acceleration | 12 mm/s$^2$ |
| Temperature | 190.0° C. |
| Piston diameter | 12 mm |
| Piston speed | 0.4862 mm/s |
| Die diameter | 2 mm |
| Die length | 30 mm |
| Shear rate at the die | 70.0 s$^{-1}$ |
| Strand length | 125.0 mm |
| Vo | 17.5 mm/s |
| Vs | 70.8 mm/s |

Figure 2:
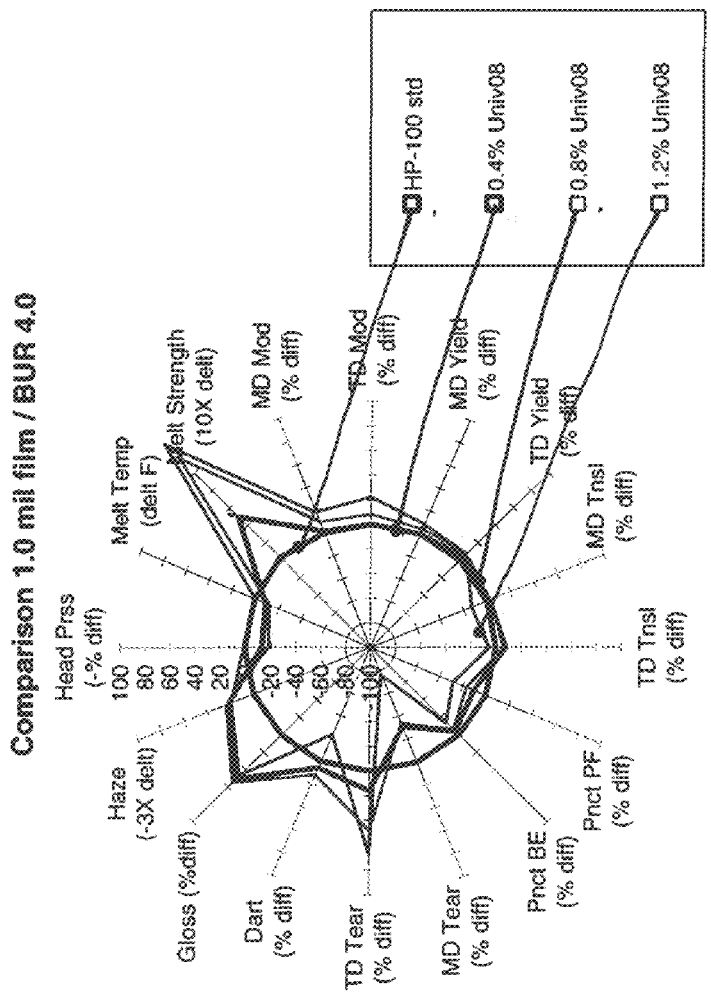
FIG. 2 provides a comparison of various properties of inventive 1.0 mil films of the instant disclosure produced with a Blow Up Ratio of 4, compared to a comparative film produced in the absence of the second catalyst of the instant disclosure.
Figure 3:
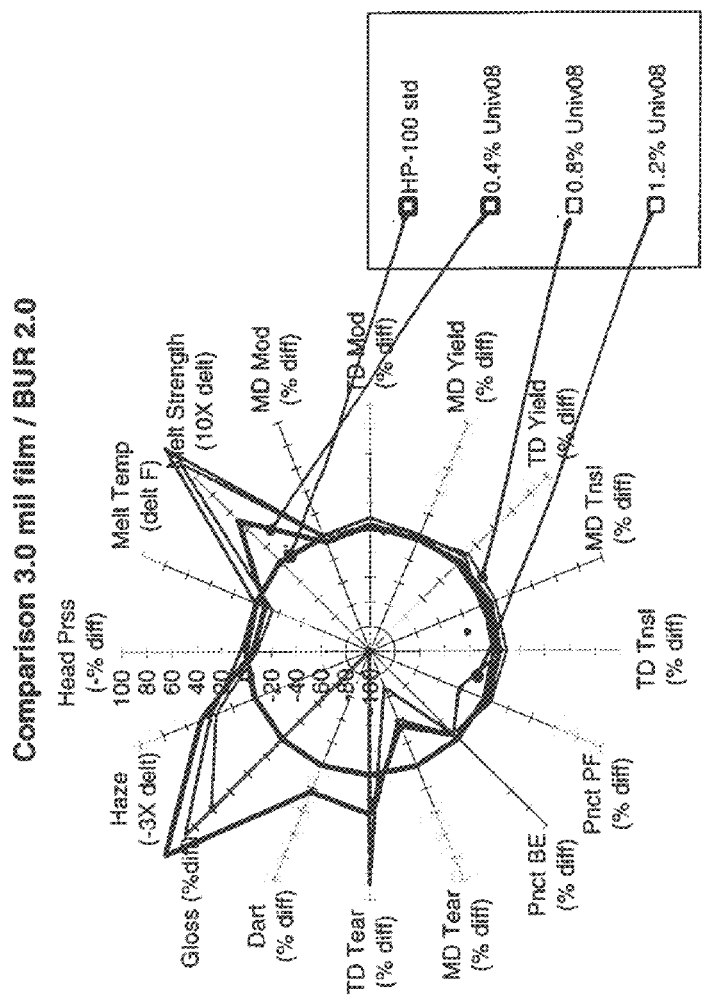
FIG. 3 provides a comparison of various properties of inventive 3.0 mil films of the instant disclosure produced with a Blow Up Ratio of 2, compared to a comparative film produced in the absence of the second catalyst of the instant disclosure.
Figure 4:
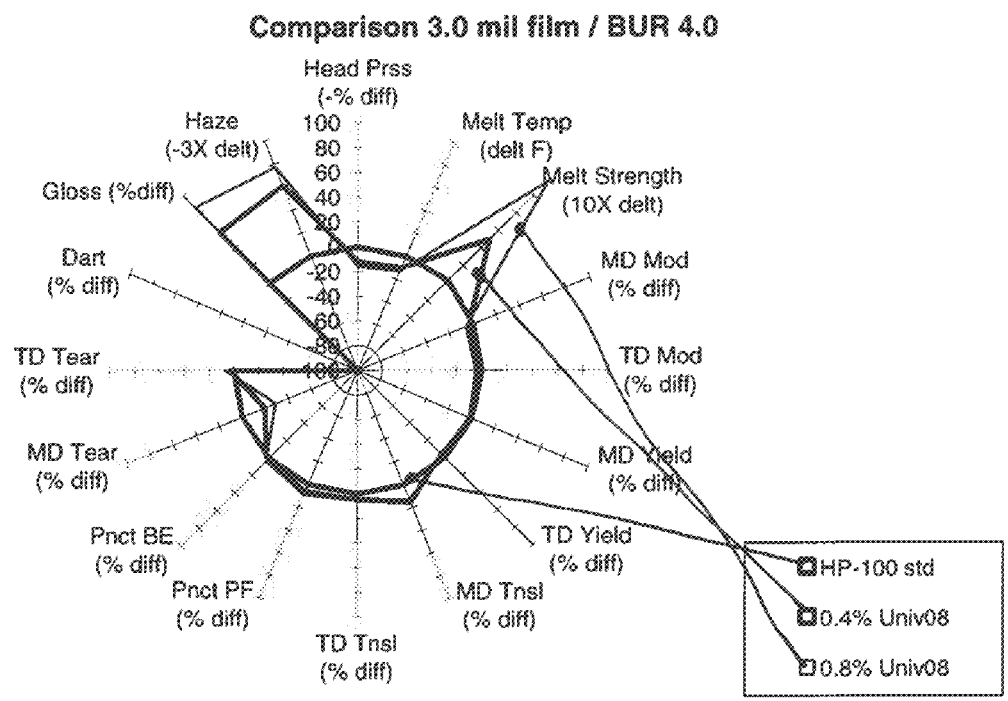
FIG. 4 provides a comparison of various properties of inventive 3.0 mil films of the instant disclosure produced with a Blow Up Ratio of 4, compared to a comparative film produced in the absence of the second catalyst of the instant disclosure.

FIG. 2 shows the melt strength of non-limiting inventive resins 1, 2, and 3 compared with several conventional resins having low MI (BMC-100 untailored, BMC-100 tailored, Borouge FB2230, and EZP 1804). As seen in FIG. 2, the melt strength of inventive resin 3 is an order of magnitude higher than that of linear or long chain branched polyethylenes of similar MI.

Film Blowing Process

Each granular resin was dry-blended with 500 ppm Irganox 1076, 2000 ppm Weston 399 (both available from Ciba Chemicals) and 800 ppm FX5920A (processing aid available from Dynamar) using a double-cone blender. Pelletizing of the resins was carried out on a Werner & Pfleiderer ZSK 57 mm twin screw extruder. Output rate was 68.1 kg/h (150 lb/h) and the melt temperature was about 210° C.

To produce film, the resins were extruded into film using a 63.5 mm (2.5 inch) Battenfield Gloucester blown film line (30:1 L:D) equipped with a 15.24 mm (6 inch) oscillating die and a Future Design air ring. Output rate was 3.36 kg/mm (188 lb/in) (or 7 g/mm/mm (10 lb/in/in) die circumference). The die temperature was 210° C. (410 F). The blow-up ratio was varied from 2.0 to 4.0 as indicated in the table. Film were produced at 1.0 and 3.0 gauge (see table).

Examples 00363-020-21 through 43A in the Table show film properties of the resins produced with embodiments of the invention described herein. Comparative examples 00363-020-011 through 014 show corresponding film properties of a resin produced without the high molecular weight component. Comparative examples 00363-020-51 through 054 show corresponding film properties of a comparable commercially available metallocene resin, (EXCEED™ 1018 available from ExxonMobil Chemical Co.). Comparative examples 00363-020-51 through 054 show corresponding film properties of a comparable commercially available metallocene resin, (EXCEED™ 1018 available from Exxon-Mobil Chemical Co.).

The following tables provide some properties of non-limiting example films produced from resins of the disclosure.

| | NOTEBOOK ID# | | | |
| --- | --- | --- | --- | --- |
| | Comparative 00363-020-011 | Comparative 00363-020-012 | Comparative 00363-020-013 | Comparative 00363-020-014 |
| | Catalyst Comparative HP-100 757 silica | | | |
| Run# | 757 silica | | | |
| Comments | | | | |
| Film Line | 2.5" BGE | | | |
| BUR | 2.00 | 2.00 | 4.00 | 4.00 |
| Gauge (Target) | 1.00 | 3.00 | 1.00 | 3.00 |
| Die Gap (mil) | 60 | | | |
| PROCESS DATA Temperature Profile (° F.) | | | | |
| Feedthroat | 87 | 87 | 87 | 86 |
| BZ1 | 300 | 301 | 298 | 299 |
| BZ2 | 390 | 390 | 390 | 390 |
| BZ3 | 375 | 375 | 375 | 375 |
| BZ4 | 350 | 350 | 350 | 350 |
| BZ5 | 350 | 350 | 350 | 350 |
| Screen Changer | 390 | 390 | 390 | 390 |
| Adapter | 390 | 390 | 390 | 390 |
| Rotator | 390 | 390 | 390 | 390 |
| Lower Die | 390 | 390 | 390 | 390 |
| Upper Die | 389 | 389 | 390 | 390 |
| Inside Die | 406 | 406 | 407 | 407 |
| Melt Temperature (° F.) | 405 | 406 | 406 | 406 |
| Output (lb/h) | 9.9 | 10.2 | 10.0 | 10.0 |
| Head Pressure (psi) | 3840 | 4080 | 3800 | 3910 |
| Die Pressure (psi) | 2520 | 2570 | 2510 | 2530 |
| Motor Load (amps) | 56.0 | 57.0 | 55.6 | 56.9 |
| Screw Speed (rpm) | 57.4 | 58.5 | 57.4 | 57.4 |
| Line Speed (fpm) | 194 | 69 | 99 | 35 |
| Gauge (mils) | 0.97 | 3.05 | 0.99 | 3.02 |
| FLH (in) | 25 | 26 | 20 | 20 |
| Air (%) | 73.4 | 62.5 | 69.3 | 60.5 |
| Air temp | 50 | 50 | 50 | 50 |

| | NOTEBOOK ID# | | | |
| --- | --- | --- | --- | --- |
| | 00363-020-031 | 00363-020-032 | 00363-020-033 | 00363-020-034 |
| | Catalyst HP-100 + 0.4% Univ08 | | | |
| Run# | | | | |
| Comments | BGE Screw | BGE Screw | BGE Screw | BGE Screw |
| Film Line | 2.5" BGE | 2.5" BGE | 2.5" BGE | 2.5" BGE |
| BUR | 2.00 | 2.00 | 4.00 | 4.00 |
| Gauge (Target) | 1.00 | 3.00 | 1.00 | 3.00 |
| Die Gap (mil) | 60 | 60 | 60 | 60 |
| PROCESS DATA Temperature Profile (° F.) | | | | |
| Feedthroat | 86 | 87 | 86 | 86 |
| BZ1 | 301 | 301 | 301 | 298 |
| BZ2 | 388 | 387 | 388 | 395 |

| NOTEBOOK ID# | | | | |
|---|---|---|---|---|
| | 00363-020-031 | 00363-020-032 | 00363-020-033 | 00363-020-034 |
| | Catalyst | | | |
| | HP-100 + 0.4% Univ08 | | | |
| BZ3 | 375 | 374 | 375 | 376 |
| BZ4 | 350 | 350 | 350 | 350 |
| BZ5 | 350 | 350 | 350 | 350 |
| Screen Changer | 390 | 390 | 390 | 390 |
| Adapter | 390 | 390 | 390 | 390 |
| Rotator | 390 | 390 | 390 | 390 |
| Lower Die | 390 | 390 | 390 | 390 |
| Upper Die | 390 | 391 | 389 | 391 |
| Inside Die | 416 | 416 | 414 | 415 |
| Melt Temperature (° F.) | 415 | 414 | 415 | 416 |
| Output (lb/h) | 9.80 | 9.74 | 9.98 | 9.91 |
| Head Pressure (psi) | 4270 | 4310 | 4300 | 4390 |
| Die Pressure (psi) | 2890 | 2840 | 2880 | 2870 |
| Motor Load (amps) | 51.5 | 48.5 | 51.5 | 50.4 |
| Screw Speed (rpm) | 63.9 | 64.0 | 63.9 | 64.0 |
| Line Speed (fpm) | 197 | 69 | 99 | 35 |
| Gauge (mils) | 0.96 | 2.90 | 1.10 | 3.06 |
| FLH (in) | 18 | 20 | 18 | 17 |
| Air (%) | 91.5 | 83.1 | 72.8 | 63.0 |
| Air temp | | 50 | 50 | 50 |

| NOTEBOOK ID# | | | | |
|---|---|---|---|---|
| | 00363-020-021 | 00363-020-022 | 00363-020-023 | 00363-020-024 |
| | Catalyst | | | |
| | HP-100 + 0.8% Univ08 | | | |
| Run# | 757 silica | | | |
| Comments | BGE Screw | BGE Screw | BGE Screw | BGE Screw |
| Film Line | 2.5" BGE | 2.5" BGE | 2.5" BGE | 2.5" BGE |
| BUR | 2.00 | 2.00 | 4.00 | 4.00 |
| Gauge (Target) | 1.00 | 3.00 | 1.00 | 3.00 |
| Die Gap (mil) | 60 | 60 | 60 | 60 |
| PROCESS DATA | | | | |
| Temperature Profile (° F.) | | | | |
| Feedthroat | 90 | 89 | 90 | 90 |
| BZ1 | 300 | 299 | 301 | 300 |
| BZ2 | 394 | 394 | 389 | 389 |
| BZ3 | 377 | 377 | 375 | 374 |
| BZ4 | 350 | 351 | 350 | 350 |
| BZ5 | 350 | 351 | 350 | 350 |
| Screen Changer | 390 | 390 | 390 | 390 |
| Adapter | 390 | 390 | 390 | 390 |
| Rotator | 390 | 390 | 390 | 390 |
| Lower Die | 390 | 390 | 390 | 390 |
| Upper Die | 389 | 389 | 389 | 389 |
| Inside Die | 419 | 420 | 420 | 420 |
| Melt Temperature (° F.) | 419 | 420 | 418 | 419 |
| Output (lb/h) | 10 | 10 | 10 | 10 |
| Head Pressure (psi) | 4420 | 4430 | 4490 | 4550 |
| Die Pressure (psi) | 2980 | 2990 | 2980 | 2940 |
| Motor Load (amps) | 48.2 | 50.5 | 47.6 | 46.1 |
| Screw Speed (rpm) | 69.5 | 68.5 | 68.4 | 68.4 |
| Line Speed (fpm) | 197.2 | 68.8 | 99.0 | 35.0 |
| Gauge (mils) | 1.07 | 2.96 | 1.01 | 2.94 |
| FLH (in) | 26 | 27 | 16 | 12 |
| Air (%) | 100.0 | 85.5 | 76.2 | 76.2 |
| Air temp | 50 | 50 | 50 | 50 |

| NOTEBOOK ID# | | | | |
|---|---|---|---|---|
| | 00363-020-041 | 00363-020-042 | 00363-020-042A | 00363-020-043A |
| | Catalyst | | | |
| | HP-100 + 1.2% Univ08 | | | |
| Run# | | | | |
| Comments | BGE Screw | | | |
| Film Line | 2.5" BGE | | | |
| BUR | 2.00 | | 2.00 | 4.00 |
| Gauge (Target) | 1.00 | | 3.00 | 3.00 |
| Die Gap (mil) | 60 | 60 | 60 | 60 |
| PROCESS DATA | | | | |
| Temperature Profile (° F.) | | | | |
| Feedthroat | 101 | | 90 | 89 |
| BZ1 | 32 | | 300 | 300 |
| BZ2 | 391 | | 390 | 390 |
| BZ3 | 375 | | 375 | 375 |
| BZ4 | 350 | | 350 | 350 |
| BZ5 | 350 | | 350 | 350 |
| Screen Changer | 390 | | 390 | 390 |
| Adapter | 390 | | 390 | 390 |
| Rotator | 390 | | 390 | 390 |
| Lower Die | 390 | | 390 | 390 |
| Upper Die | 391 | | 391 | 390 |
| Inside Die | 410 | | 418 | 417 |
| Melt Temperature (° F.) | 416 | | 418 | 418 |
| Output (lb/h) | 9.71 | | 8.74 | 8.70 |
| Head Pressure (psi) | 4530 | | 4290 | 4480 |
| Die Pressure (psi) | 3010 | | 2850 | 2880 |
| Motor Load (amps) | 55.2 | | 50.4 | 55.5 |
| Screw Speed (rpm) | 64.5 | | 64.0 | 66.6 |
| Line Speed (fpm) | 197 | | 62 | 85 |
| Gauge (mils) | 1.04 | | 2.93 | 3.00 |
| FLH (in) | 28 | | 20 | 15 |
| Air (%) | 100.0 | | 100.0 | 61.30 |
| Air temp | 50 | | 50 | 50 |

Table Film Properties Comparative Film

| NOTEBOOK ID# | | | | |
|---|---|---|---|---|
| | Comparative 00363-020-051 | Comparative 00363-020-052 | Comparative 00363-020-053 | Comparative 00363-020-054 |
| | Catalyst | | | |
| | Comparative Exceed1018 | | | |
| Run# | | | | |
| Comments | BGE Screw | BGE Screw | BGE Screw | BGE Screw |
| Film Line | 2.5" BGE | 2.5" BGE | 2.5" BGE | 2.5" BGE |
| BUR | 2.00 | 2.00 | 4.00 | 4.00 |
| Gauge (Target) | 1.00 | 3.00 | 1.00 | 3.00 |
| Die Gap (mil) | 60 | 60 | 60 | 60 |
| PROCESS DATA | | | | |
| Temperature Profile (° F.) | | | | |
| Feedthroat | 92 | 92 | 93 | 93 |
| BZ1 | 292 | 300 | 299 | 306 |
| BZ2 | 402 | 387 | 393 | 385 |
| BZ3 | 378 | 375 | 376 | 375 |
| BZ4 | 350 | 350 | 350 | 350 |
| BZ5 | 351 | 350 | 350 | 350 |
| Screen Changer | 390 | 390 | 390 | 390 |
| Adapter | 390 | 390 | 390 | 390 |
| Rotator | 390 | 390 | 390 | 390 |
| Lower Die | 390 | 390 | 390 | 390 |
| Upper Die | 391 | 390 | 391 | 390 |
| Inside Die | 409 | 411 | 409 | 409 |

Table Film Properties Comparative Film

NOTEBOOK ID#

| | Comparative 00363-020-051 | Comparative 00363-020-052 | Comparative 00363-020-053 | Comparative 00363-020-054 |
|---|---|---|---|---|
| Catalyst | Comparative Exceed1018 | | | |
| Melt Temperature (° F.) | 410 | 409 | 409 | 408 |
| Output (lb/h) | 9.98 | 10.16 | 10.13 | 10.04 |
| Head Pressure (psi) | 4000 | 3920 | 3940 | 4000 |
| Die Pressure (psi) | 2560 | 2570 | 2550 | 2540 |
| Motor Load (amps) | 55.6 | 56.8 | 58.3 | 53.7 |
| Screw Speed (rpm) | 61.9 | 69.0 | 60.9 | 60.9 |
| Line Speed (fpm) | 197 | 69 | 99 | 35 |
| Gauge (mils) | 1.02 | 3.02 | 1.00 | 2.92 |
| FLH (in) | 24 | 24 | 20 | 20 |
| Air (%) | 75.1 | 73.8 | 66.9 | 62.6 |
| Air temp | 50 | 50 | 50 | 50 |

Sample ID

| | Comparative 00363-020-011 | Comparative 00363-020-012 | Comparative 00363-020-013 | Comparative 00363-020-014 |
|---|---|---|---|---|
| Catalyst | HP-100 | HP-100 | HP-100 | HP-100 |
| BUR | 2.0 | 2.0 | 4.0 | 4.0 |
| Target gauge | 1.0 | 3.0 | 1.0 | 3.0 |
| Gauge Mic (mils) | | | | |
| Average | 1.08 | 3.09 | 1.08 | 3.03 |
| Low | 1.03 | 2.98 | 1.00 | 2.90 |
| High | 1.13 | 3.19 | 1.17 | 3.17 |
| 1% Secant (psi) | | | | |
| MD | 27,982 | 30,827 | 25,446 | 30,557 |
| TD | 33,452 | 34,600 | 27,485 | 31,546 |
| Tensile Yield Strength (psi) | | | | |
| MD | 1,397 | 1,382 | 1,349 | 1,378 |
| TD | 1,462 | 1,477 | 1,389 | 1,447 |
| Elong @ Yield (%) | | | | |
| MD | 5.8 | 5.8 | 6.3 | 5.8 |
| TD | 5.0 | 5.5 | 5.9 | 6.3 |
| Tensile Strength (psi) | | | | |
| MD | 10,051 | 8,278 | 9,665 | 7,647 |
| TD | 8,112 | 7,646 | 9,256 | 8,079 |
| Elongation @ Break (%) | | | | |
| MD | 523 | 713 | 610 | 721 |
| TD | 706 | 764 | 658 | 752 |
| Elmendorf Tear | | | | |
| MD (gms) | 248 | 970 | 318 | 1,083 |
| TD (gms) | 571 | 1,259 | 410 | 1,174 |
| MD (gms/mil) | 226 | 312 | 295 | 357 |
| TD (gms/mil) | 524 | 406 | 372 | 386 |
| MD/TD | 43% | 77% | 79% | 92% |
| Puncture (Method B) | | | | |
| Pk Load (lbs) | 11.1 | 22.5 | 10.3 | 21.1 |
| Peak/mil (lbs/mil) | 10.3 | 7.3 | 9.6 | 7.0 |
| Bk Energy (in-lb) | 36.2 | 63.8 | 32.4 | 58.0 |
| Bk Eng/mil (in-lb/mil) | 33.5 | 20.6 | 30.0 | 19.1 |
| Gauge Mic (mils) | | | | |
| Average | 1.08 | 3.09 | 1.08 | 3.03 |
| Low | 1.03 | 2.98 | 1.00 | 2.90 |
| High | 1.13 | 3.19 | 1.17 | 3.17 |
| Dart Drop | | | | |
| (gms) | 334 | 1017 | 744 | >1369 |
| (g/mil) | 309 | 329 | 689 | >452 |
| Internal Haze (%) | 3.45 | 14.40 | 2.99 | 16.20 |
| Haze (%) | 12.5 | 26.7 | 18.0 | 36.5 |
| Clarity | 98.7 | 95.2 | 96.7 | 88.6 |
| Gloss | | | | |
| MD | 47.8 | 25.1 | 36.1 | 32.1 |
| TD | 50.0 | 30.0 | 35.6 | 31.8 |
| Shrink (%) | | | | |
| MD | 60 | 41 | 41 | 32 |
| TD | −19 | −8 | 10 | 5 |
| COF | | | | |
| Static | 1.198 | 0.798 | 1.643* | 0.948 |
| Kinetic | 1.01 | 0.709 | 1.433* | 0.824 |

Inventive Film Properties

Sample ID

| | Inventive 00363-020-031 | Inventive 00363-020-032 | Inventive 00363-020-033 | Inventive 00363-020-034 |
|---|---|---|---|---|
| Catalyst | HP-100 + 0.4% UNIV08 | HP-100 + 0.4% UNIV08 | HP-100 + 0.4% UNIV08 | HP-100 + 0.4% UNIV08 |
| BUR | 2.0 | 2.0 | 4.0 | 4.0 |
| Target gauge | 1.0 | 3.0 | 1.0 | 3.0 |

-continued

| | Inventive Film Properties ||||
|---|---|---|---|---|
| | Sample ID ||||
| | Inventive 00363-020-031 | Inventive 00363-020-032 | Inventive 00363-020-033 | Inventive 00363-020-034 |
| | Catalyst ||||
| | HP-100 + 0.4% UNIV08 | HP-100 + 0.4% UNIV08 | HP-100 + 0.4% UNIV08 | HP-100 + 0.4% UNIV08 |
| Gauge Mic (mils) | | | | |
| Average | 1.05 | 3.00 | 1.09 | 3.03 |
| Low | 0.99 | 2.86 | 1.02 | 2.79 |
| High | 1.10 | 3.14 | 1.18 | 3.19 |
| 1% Secant (psi) | | | | |
| MD | 31,310 | 29,360 | 25,835 | 29,265 |
| TD | 40,433 | 35,209 | 27,494 | 30,174 |
| Tensile Yield Strength (psi) | | | | |
| MD | 1,523 | 1,359 | 1,346 | 1,371 |
| TD | 1,686 | 1,508 | 1,440 | 1,395 |
| Elong @ Yield (%) | | | | |
| MD | 6.1 | 5.8 | 5.9 | 6.0 |
| TD | 5.6 | 5.4 | 6.9 | 5.8 |
| Tensile Strength (psi) | | | | |
| MD | 9,791 | 8,646 | 9,880 | 8,716 |
| TD | 8,725 | 7,956 | 9,962 | 8,447 |
| Elongation @ Break (%) | | | | |
| MD | 404 | 637 | 546 | 711 |
| TD | 734 | 752 | 629 | 728 |
| Elmendorf Tear | | | | |
| MD (gms) | 105 | 601 | 222 | 856 |
| TD (gms) | 773 | 1,599 | 448 | 1,199 |
| MD (gms/mil) | 99 | 202 | 203 | 287 |
| TD (gms/mil) | 744 | 534 | 431 | 398 |
| MD/TD | 13% | 38% | 47% | 72% |
| Puncture (Method B) | | | | |
| Pk Load (lbs) | 12.3 | 22.4 | 12.1 | 22.4 |
| Peak/mil (lbs/mil) | 11.7 | 7.5 | 11.1 | 7.4 |
| Bk Energy (in-lb) | 38.2 | 59.5 | 36.8 | 59.3 |
| Bk Eng/mil (in-lb/mil) | 36.3 | 19.8 | 33.7 | 19.6 |
| Gauge Mic (mils) | | | | |
| Average | 1.05 | 3.00 | 1.09 | 3.03 |
| Low | 0.99 | 2.86 | 1.02 | 2.79 |
| High | 1.10 | 3.14 | 1.18 | 3.19 |
| Dart Drop | | | | |
| (gms) | 271 | 1214 | 793 | >1369 |
| (g/mil) | 258 | 405 | 728 | >452 |
| Internal Haze (%) | 1.44 | 5.57 | 1.66 | 5.64 |
| Haze (%) | 4.89 | 11.2 | 10.8 | 16.1 |
| Clarity | 99.2 | 99.0 | 98.4 | 98.5 |
| Gloss | | | | |
| MD | 76.2 | 63.1 | 53.9 | 50.2 |
| TD | 78.0 | 65.2 | 54.3 | 50.5 |
| Shrink (%) | | | | |
| MD | 78 | 72 | 70 | 65 |
| TD | −43 | −36 | 2 | −1 |
| COF | | | | |
| Static | >1** | 0.644 | 1.290 | 1.051 |
| Kinetic | >1** | 0.485 | 1.114 | 0.893 |

|  | Sample ID | | | |
|---|---|---|---|---|
|  | Inventive 00363-020-021 | Inventive 00363-020-022 | Inventive 00363-020-023 | Inventive 00363-020-024 |
|  | Catalyst | | | |
|  | HP-100 + 0.8% UNIV08 | HP-100 + 0.8% UNIV08 | HP-100 + 0.8% UNIV08 | HP-100 + 0.8% UNIV08 |
| BUR | 2.0 | 2.0 | 4.0 | 4.0 |
| Target gauge | 1.0 | 3.0 | 1.0 | 3.0 |
| Gauge Mic (mils) | | | | |
| Average | 1.09 | 3.17 | 1.08 | 3.04 |
| Low | 0.98 | 2.94 | 0.97 | 2.87 |
| High | 1.16 | 3.42 | 1.15 | 3.22 |
| 1% Secant (psi) | | | | |
| MD | 33,872 | 30,588 | 28,005 | 28,615 |
| TD | 41,043 | 35,703 | 29,729 | 29,904 |
| Tensile Yield Strength (psi) | | | | |
| MD | 1,511 | 1,395 | 1,406 | 1,341 |
| TD | 1,707 | 1,641 | 1,488 | 1,391 |
| Elong @ Yield (%) | | | | |
| MD | 5.7 | 5.9 | 6.4 | 5.7 |
| TD | 5.9 | 7.3 | 6.3 | 5.9 |
| Tensile Strength (psi) | | | | |
| MD | 10,124 | 9,000 | 9,893 | 8,915 |
| TD | 9,243 | 8,360 | 9,829 | 8,541 |
| Elongation @ Break (%) | | | | |
| MD | 421 | 665 | 505 | 697 |
| TD | 693 | 754 | 617 | 704 |
| Elmendorf Tear | | | | |
| MD (gms) | 103 | 565 | 213 | 759 |
| TD (gms) | 791 | 1,827 | 584 | 1,237 |
| MD (gms/mil) | 95 | 186 | 194 | 253 |
| TD (gms/mil) | 736 | 596 | 552 | 414 |
| MD/TD | 13% | 31% | 35% | 61% |
| Puncture (Method B) | | | | |
| Pk Load (lbs) | 12.7 | 24.4 | 12.3 | 23.2 |
| Peak/mil (lbs/mil) | 11.7 | 7.7 | 11.4 | 7.6 |
| Bk Energy (in-lb) | 35.0 | 62.8 | 35.2 | 60.4 |
| Bk Eng/mil (in-lb/mil) | 32.1 | 19.8 | 32.6 | 19.9 |
| Gauge Mic (mils) | | | | |
| Average | 1.09 | 3.17 | 1.08 | 3.04 |
| Low | 0.98 | 2.94 | 0.97 | 2.87 |
| High | 1.16 | 3.42 | 1.15 | 3.22 |
| Dart Drop | | | | |
| (gms) | 480 | >1369 | 834 | >1369 |
| (g/mil) | 440 | >432 | 772 | >450 |
| Internal Haze (%) | 2.34 | 6.65 | 2.53 | 5.53 |
| Haze (%) | 8.3 | 15.4 | 10.1 | 10.8 |
| Clarity | 96.7 | 97.5 | 97.5 | 98.3 |
| Gloss | | | | |
| MD | 59.4 | 49.3 | 55.6 | 58.9 |
| TD | 58.3 | 50.3 | 55.5 | 60.1 |
| Shrink (%) | | | | |
| MD | 86 | 82 | 78 | 76 |
| TD | −41 | −43 | 2 | 9 |
| COF | | | | |
| Static | 1.065 | 0.723 | 0.984 | 0.984 |
| Kinetic | 0.903 | 0.613 | 0.855 | 0.834 |

|  | Sample ID | | | |
|---|---|---|---|---|
|  | Inventive 00363-020-041 | Inventive 00363-020-041A | Inventive 00363-020-042A | Inventive 00363-020-043A |
|  | Catalyst | | | |
|  | HP-100 + 1.2% UNIV08 | HP-100 + 1.2% UNIV08 | HP-100 + 1.2% UNIV08 | HP-100 + 1.2% UNIV08 |
| BUR | 2.0 | 2.0 | 2.0 | 4.0 |
| Target gauge | 1.0 | 1.0 | 1.0 | 3.0 |
| Gauge Mic (mils) | | | | |
| Average | 1.02 | 1.04 | 3.00 | 1.09 |
| Low | 0.89 | 0.93 | 2.86 | 1.02 |
| High | 1.11 | 1.14 | 3.13 | 1.14 |
| 1% Secant (psi) | | | | |
| MD | 36,123 | 39,245 | 31,219 | 30,147 |
| TD | 47,217 | 52,757 | 37,464 | 33,636 |
| Tensile Yield Strength (psi) | | | | |
| MD | 1,551 | 1,698 | 1,420 | 1,467 |
| TD | 1,851 | 1,867 | 1,598 | 1,492 |
| Elong @ Yield (%) | | | | |
| MD | 5.6 | 6.0 | 5.9 | 5.9 |
| TD | 8.1 | 5.4 | 5.8 | 5.6 |
| Tensile Strength (psi) | | | | |
| MD | 9,552 | 8,307 | 7,988 | 8,419 |
| TD | 9,168 | 8,748 | 8,148 | 8,772 |
| Elongation @ Break (%) | | | | |
| MD | 386 | 323 | 553 | 437 |
| TD | 693 | 669 | 728 | 566 |
| Elmendorf Tear | | | | |
| MD (gms) | 88 | 48 | 293 | 76 |
| TD (gms) | 807 | 803 | 2,301 | 689 |
| MD (gms/mil) | 84 | 45 | 97 | 69 |
| TD (gms/mil) | 765 | 746 | 767 | 623 |
| MD/TD | 11% | 6% | 13% | 11% |
| Puncture (Method B) | | | | |
| Pk Load (lbs) | 13.4 | 12.4 | 24.2 | 13.4 |
| Peak/mil (lbs/mil) | 13.1 | 11.9 | 8.1 | 12.3 |
| Bk Energy (in-lb) | 36.4 | 24.2 | 54.1 | 34.9 |
| Bk Eng/mil (in-lb/mil) | 35.7 | 23.3 | 18.0 | 32.0 |
| Gauge Mic (mils) | | | | |
| Average | 1.02 | 1.04 | 3.00 | 1.09 |
| Low | 0.89 | 0.93 | 2.86 | 1.02 |
| High | 1.11 | 1.14 | 3.13 | 1.14 |
| Dart Drop | | | | |
| (gms) | 514 | 464 | >1369 | 575 |
| (g/mil) | 504 | 446 | >456 | 528 |
| Internal Haze (%) | 0.93 | 0.94 | 3.91 | 1.50 |
| Haze (%) | 8.9 | 9.75 | 14.0 | 11.6 |
| Clarity | 95.9 | 91.1 | 92.7 | 92.4 |
| Gloss | | | | |
| MD | 65.4 | 60.6 | 57.2 | 52.8 |
| TD | 64.1 | 59.8 | 58.6 | 52.3 |
| Shrink (%) | | | | |
| MD | 87 | 86 | 85 | 84 |
| TD | −43 | −51 | −38 | 3 |
| COF | | | | |
| Static | 1.034 | 1.027 | 0.856 | 0.949 |
| Kinetic | 0.935 | 0.884 | 0.737 | 0.795 |

|  | Sample ID | | | |
|---|---|---|---|---|
|  | Comparative 00363-020-051 | Comparative 00363-020-052 | Comparative 00363-020-053 | Comparative 00363-020-054 |
|  | Catalyst | | | |
|  | Exceed1018 | Exceed1018 | Exceed1018 | Exceed1018 |
| BUR | 2.0 | 2.0 | 4.0 | 4.0 |
| Target gauge | 1.0 | 3.0 | 1.0 | 3.0 |
| Gauge Mic (mils) | | | | |
| Average | 1.07 | 3.06 | 1.07 | 3.01 |
| Low | 1.03 | 2.95 | 1.01 | 2.90 |
| High | 1.11 | 3.17 | 1.14 | 3.16 |
| 1% Secant (psi) | | | | |
| MD | 22,356 | 24,780 | 21,557 | 24,903 |
| TD | 26,015 | 27,374 | 22,012 | 25,356 |
| Tensile Yield Strength (psi) | | | | |
| MD | 1,274 | 1,259 | 1,197 | 1,213 |
| TD | 1,316 | 1,264 | 1,252 | 1,232 |
| Elong @ Yield (%) | | | | |
| MD | 6.8 | 6.8 | 6.6 | 6.0 |
| TD | 6.5 | 5.9 | 7.1 | 6.1 |
| Tensile Strength (psi) | | | | |
| MD | 9,721 | 8,455 | 10,109 | 8,001 |
| TD | 8,312 | 7,482 | 9,215 | 8,228 |
| Elongation @ Break (%) | | | | |
| MD | 486 | 688 | 588 | 700 |
| TD | 694 | 732 | 634 | 725 |
| Elmendorf Tear | | | | |
| MD (gms) | 250 | 889 | 279 | 994 |
| TD (gms) | 461 | 1,135 | 338 | 1,045 |
| MD (gms/mil) | 243 | 291 | 258 | 330 |
| TD (gms/mil) | 447 | 375 | 309 | 343 |
| MD/TD | 54% | 78% | 83% | 96% |
| Puncture (Method B) | | | | |
| Pk Load (lbs) | 10.8 | 21.9 | 10.4 | 21.4 |
| Peak/mil (lbs/mil) | 10.1 | 7.2 | 9.7 | 7.1 |
| Bk Energy (in-lb) | 35.9 | 62.6 | 33.4 | 60.8 |
| Bk Eng/mil (in-lb/mil) | 33.6 | 20.5 | 31.2 | 20.2 |
| Gauge Mic (mils) | | | | |
| Average | 1.07 | 3.06 | 1.07 | 3.01 |
| Low | 1.03 | 2.95 | 1.01 | 2.90 |
| High | 1.11 | 3.17 | 1.14 | 3.16 |
| Dart Drop | | | | |
| (gms) | 513 | >1369 | 973 | >1369 |
| (g/mil) | 479 | >447 | 909 | >455 |
| Internal Haze (%) | 1.98 | 12.30 | 1.63 | 12.10 |
| Haze (%) | 9.26 | 26.8 | 29.8 | 31.8 |
| Clarity | 98.6 | 94.5 | 89.5 | 90.0 |
| Gloss | | | | |
| MD | 67.5 | 48.7 | 23.8 | 34.4 |
| TD | 65.1 | 50.1 | 23.8 | 33.7 |
| Shrink (%) | | | | |
| MD | 55 | 36 | 41 | 23 |
| TD | −9 | −6 | 12 | 10 |
| COF | | | | |
| Static | 1.436* | >1** | >1* | 1.223 |
| Kinetic | 1.187* | >1** | >1* | 0.995 |

The phrases, unless otherwise specified, "consists essentially of" and "consisting essentially of" do not exclude the presence of other steps, elements, or materials, whether or not, specifically mentioned in this specification, as along as such steps, elements, or materials, do not affect the basic and novel characteristics of the invention, additionally, they do not exclude impurities normally associated with the elements and materials used.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, within a range includes every point or individual value between its end points even though not explicitly recited. Thus, every point or individual value may serve as its own lower or upper limit combined with any other point or individual value or any other lower or upper limit, to recite a range not explicitly recited.

All priority documents are herein fully incorporated by reference for all jurisdictions in which such incorporation is permitted and to the extent such disclosure is consistent with the description of the present invention. Further, all documents and references cited herein, including testing procedures, publications, patents, journal articles, etc. are herein fully incorporated by reference for all jurisdictions in which such incorporation is permitted and to the extent such disclosure is consistent with the description of the present invention.

While the invention has been described with respect to a number of embodiments and examples, those skilled in the art, having benefit of this disclosure, will appreciate that other embodiments can be devised which do not depart from the scope and spirit of the invention as disclosed herein.

What is claimed is:

1. A film of an ethylene polymer comprising:
    an ethylene polymer produced in a gas phase process comprising a catalyst system comprising a first catalyst compound and a second catalyst compound disposed on a support, wherein the first catalyst compound is a metallocene catalyst compound; and
    wherein the second catalyst compound has the following formula I:

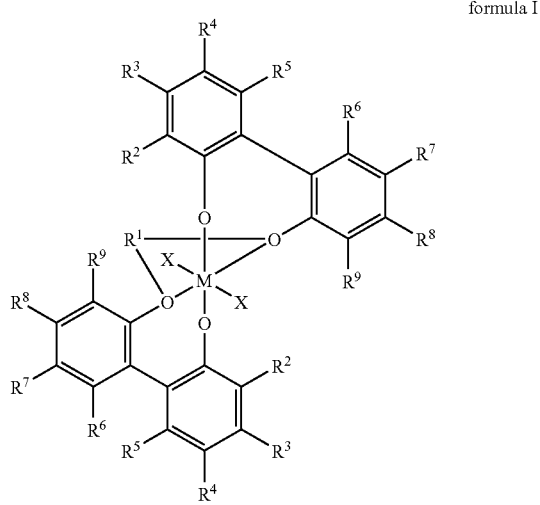

formula I wherein M is selected from the group consisting of Ti, Zr, and Hf; each $R^1$ through $R^9$ may be independently selected from the group consisting of hydride, hydrocarbyl, lower hydrocarbyl, substituted hydrocarbyl, heterohydrocarbyl, alkyl, lower alkyl, substituted alkyl, heteroalkyl, alkenyl, lower alkenyl, substituted alkenyl, heteroalkenyl, alkynyl, lower alkynyl, substituted alkynyl, heteroalkynyl, alkoxy, lower alkoxy, aryloxy, hydroxyl, alkylthio, lower alkyl thio, arylthio, thioxy, aryl, substituted aryl, heteroaryl, aralkyl, aralkylene, alkaryl, alkarylene, halide, haloalkyl, haloalkenyl, haloalkynyl, heteroalkyl, heterocycle, heteroaryl, heteroatom-containing group, silyl, boryl, phosphino, phosphine, amino, and amine; wherein X is least one leaving group; and optionally, a cocatalyst;

wherein the ethylene polymer comprises a bimodal polymer that comprises a high molecular weight component and a low molecular weight component, and wherein the ethylene polymer comprises from about 0.01 to about 25% of the high molecular weight component where the fraction of the high molecular weight component is determined by integrating the area under the molecular weight vs. dwt %/d Log M curve from molecular weight =1,000,000 to molecular weight =10,000,000;

wherein the film of the ethylene polymer has a gauge of 1 mil to 3 mils, a dart drop impact strength as determined by ASTM D1709A greater than or equal to 400 g/mil, an Elmendorf Tear in the machine direction as determined by ASTM 1922 greater than or equal to about 150 g/mil, an Elmendorf Tear in the transverse direction as determined by ASTM 1922 greater than or equal to 450 g/mil; a haze as determined by ASTM D2103-08 less than or equal to about 15%; and a gloss as determined by ASTM D2457-08 greater than or equal to about 45%; and wherein the film of the ethylene polymer has at least one of an improved gloss as determined by ASTM D2457-08 such that the gloss is at least 10% greater than that of a comparative film, a reduced haze as determined by ASTM D2103-08 such that the haze is at least 100% less than that of a comparative film, an improved dart drop impact strength as determined by ASTM D1709A such that the dart drop impact strength is at least 10% greater than that of a comparative film, and improved Elmendorf Tear in the machine direction as determined by ASTM 1922 such that the Elmendorf Tear in the machine direction is at least 10% greater than that of a comparative film, an improved Elmendorf Tear in the Transverse direction as determined by ASTM 1922 such that the Elmendorf Tear in the transverse direction is at least 10% greater than that of a comparative film, or a combination thereof, when compared to a comparative film produced in essentially the same way from a comparative resin, the comparative resin produced in essentially the same way using essentially the same components except that the comparative resin is produced in the absence of the second catalyst compound.

2. The film of claim 1, wherein the dart drop impact strength is greater than or equal to about 450 g/mil.

3. The film of claim 1, wherein the gloss is greater than or equal to about 55%.

4. The film of claim 1, wherein the haze is less than or equal to about 10%.

5. The film of claim 1, wherein the Elmendorf Tear in the machine direction (MD) is greater than or equal to about 250 g/mil.

6. The film of claim 1, wherein the Elmendorf Tear in the transverse direction (TD) is greater than or equal to about 600 g/mil.

7. The film of claim 1, wherein the Elmendorf Tear Ratio, MD/TD is greater than or equal to about 55%.

8. The film of claim 1, wherein the ethylene polymer comprises at least one comonomer species selected from the group consisting of propylene, 1-butene, t-pentene, 1-hexene, 1-heptene, 1-octene, and combinations thereof.

9. The film of claim 1, wherein the ethylene polymer has a density measured in accordance with ASTM 1505-03 in the range of 0.89 g/cm$^3$ to 0.93 g/cm$^3$.

* * * * *